(12) United States Patent
Almeida-Porada et al.

(10) Patent No.: US 10,913,933 B2
(45) Date of Patent: Feb. 9, 2021

(54) BIOENGINEERED LIVER CONSTRUCTS AND METHODS RELATING THERETO

(71) Applicant: Wake Forest University Health Sciences, Winston-Salem, NC (US)

(72) Inventors: Maria Graca Almeida-Porada, Winston-Salem, NC (US); Pedro Miguel A. M. Baptista, Winston-Salem, NC (US); Shay Soker, Greensboro, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 112 days.

(21) Appl. No.: 14/767,335

(22) PCT Filed: Feb. 13, 2014

(86) PCT No.: PCT/US2014/016331
§ 371 (c)(1),
(2) Date: Aug. 12, 2015

(87) PCT Pub. No.: WO2014/127170
PCT Pub. Date: Aug. 21, 2014

(65) Prior Publication Data
US 2016/0002602 A1 Jan. 7, 2016

Related U.S. Application Data

(60) Provisional application No. 61/764,174, filed on Feb. 13, 2013.

(51) Int. Cl.
*C12N 5/071* (2010.01)
*C12N 5/0789* (2010.01)
*C12N 5/00* (2006.01)

(52) U.S. Cl.
CPC ......... *C12N 5/0671* (2013.01); *C12N 5/0068* (2013.01); *C12N 5/067* (2013.01); *C12N 5/0647* (2013.01); *C12N 2501/01* (2013.01); *C12N 2501/04* (2013.01); *C12N 2501/11* (2013.01); *C12N 2501/115* (2013.01); *C12N 2501/12* (2013.01); *C12N 2501/125* (2013.01); *C12N 2501/235* (2013.01); *C12N 2501/26* (2013.01); *C12N 2501/30* (2013.01); *C12N 2501/305* (2013.01); *C12N 2501/315* (2013.01); *C12N 2501/727* (2013.01); *C12N 2501/998* (2013.01); *C12N 2501/999* (2013.01); *C12N 2533/90* (2013.01)

(58) Field of Classification Search
CPC ... C12N 5/0671; C12N 5/0068; C12N 5/0647
See application file for complete search history.

(56) References Cited

U.S. PATENT DOCUMENTS

| 5,613,982 A | 3/1997 | Goldstein |
| 2013/0288375 A1 | 10/2013 | Zhang et al. |
| 2014/0016331 A1 | 1/2014 | Ting |

FOREIGN PATENT DOCUMENTS

| WO | 2005118780 | 12/2005 |
| WO | 2005118780 A1 | 12/2005 |
| WO | 2008137641 | 11/2008 |
| WO | 2008137641 A2 | 11/2008 |
| WO | 2012005760 A1 | 1/2012 |
| WO | 2012094255 | 7/2012 |
| WO | 2012094255 A2 | 7/2012 |
| WO | 2014127170 A1 | 8/2014 |

OTHER PUBLICATIONS

Schmelzer "Human hepatic stem cells from fetal and postnatal donors" JEM, The Rockefeller University Press vol. 204, No. 8, Aug. 6, 2007 1973-1987.*
Soker et al. "Regenerative medicine as applied to solid organ transplantation: current status and future challenges" Transplant International 2010 European Society for Organ Transplantation 24 (2011) 223-232.*
Almeida-Porada, et al., "Evaluation of Serum-Free Culture Conditions Able to Support the Ex Vivo Expansion and Engraftment of Human Hematopoietic Stem Cells in the Human-to-Sheep Xenograft Model", J. Hematother. Stem Cell Res., 2000, 9(5):683-693.
Almeida-Porada, et al., "Tissue of Origin Influences In Vivo Differentiative Potential of Mesenchymal Stem Cells", Blood, 2003, 102(11):abstract #1304(45th Annual Meeting of the American Society of Hematology, Dec. 6-9, 2003).
Andrade, et al., "Systematic delineation of optimal cytokine concentrations to expand hematopoietic stem/progenitor cells in co-culture with mesenchymal stem cells", Mol. Biosyst., 2010, 6(7):1207-1215.
Andrade, et al., "Initial CD34+ Cell-Enrichment of Cord Blood Determines Hematopoietic Stem/Progenitor Cell Yield Upon Ex Vivo Expansion", Journal of Cellular Biochemistry, 2011, 112(7):1822-1831.
Azuma, et al., "Robust expansion of human hepatocytes in Fah-1-/Rag2-1-/Il2rg-1- mice", Nature Biotechnology, 2007, 25(8):903-910.
Ballen and Spitzer, "The great debate: haploidentical or cord blood transplant", Bone Marrow Transplantation, 2011, 46(3):323-329.
Ballen, et al., "Selection of optimal alternative graft source: mismatched unrelated donor, umbilical cord blood, or haploidentical transplant", Blood, Mar. 1, 2012, 119(9):1972-1980.
Baptista, et al., "The Use of Whole Organ Decellularization for the Generation of a Vascularized Liver Organoid", Hepatology, 2011, 53(2):604-617.
Baptista, et al., "Whole Organ Decellularization—A Tool for Bioscaffold Fabrication and Organ Bioengineering", Conference Proceedings: Annual International Conference of the IEEE Engineering in Medicine and Biology Society, 2009, 6526-6529.

(Continued)

*Primary Examiner* — Blaine Lankford
(74) *Attorney, Agent, or Firm* — Kilpatrick Townsend & Stockton LLP

(57) ABSTRACT

An in vitro liver organoid is provided along with methods of making and using the organoid. A cell culture system that includes the liver organoid is also provided. The liver organoid has fetal liver characteristics and supports expansion and differentiation of hematopoietic stem cells.

20 Claims, 15 Drawing Sheets

(56) References Cited

OTHER PUBLICATIONS

Baptista, et al., "Human Liver Bioengineering Using a Whole Liver Decellularized Bioscaffold", *Organ Regeneration: Methods and Protocols, Methods in Molecular Biology*, Ed. Joydeep Basu and John W. Ludlow. New York: Springer Science+Business Media, 2013, 1001:289-298.
Boxall, et al., "Haematopoietic repopulating activity in human cord blood CD133+ quiescent cells", Bone Marrow Transplantation, 2009, 43(8):627-635.
Broxmeyer, "Insights into the biology of cord blood stem/progenitor cells", Cell Prolif., 2011, 44(Suppl. 1):55-59.
Brummendorf, et al., "Asymmetric Cell Divisions Sustain Long-Term Hematopoiesis from Single-sorted Human Fetal Liver Cells", J. Exp. Med., 1998, 188(6):1117-1124.
Campbell, et al, "Inhibition of CD26 in Human Cord Blood CD34+ Cells Enhances Their Engraftment of Nonobese Diabetic/Severe Combined Immunodeficiency Mice", Stem Cells and Development, 2007, 16(3):347-353.
Carson, "Extracellular matrix: Forum introduction", Reproductive Biology and Endocrinology, 2004, 2:1-2.
Chamberlain, et al., "Stro-1 Indentifies a Putative Mesenchymal Stem Cell Population in Human Brain", Experimental Hematology, 2003, 31:168.
Chamberlain, et al., "Neural Generation In Vivo Differs With Route of Administration and Source of Mesenchymal Stem Cells", Experimental Hematology, 2005, 33(7):49.
Chen, et al., "Humanized mice with ectopic artificial liver tissues", PNAS, 2011, 108(29):11842-11847.
Choi, et al., "Effects of mixed feeder cells on the expansion of CD34+ cells", Journal of Bioscience and Bioengineering, 2012, 113(3):389-394.
Chou and Lodish, "Fetal liver hepatic progenitors are supportive stromal cells for hematopoietic stem cells", PNAS, 2010, 107(17):7799-7804.
Ciriza, et al., "The migration of hematopoietic progenitors from the fetal liver to the fetal bone marrow: Lessons learned and possible clinical applications", Experimental Hematology, 2013, 41(5):411-423.
Csaszar, et al., "Rapid Expansion of Human Hematopoietic Stem Cells by Automated Control of Inhibitory Feedback Signaling", Cell Stem Cell, 2012, 10(2):218-229.
Dahlberg, et al., "Ex vivo expansion of human hematopoietic stem and progenitor cells", Blood, 2011, 117(23):6083-6090.
Da Silva, et al., "Modelling of ex vivo expansion/maintenance of hematopoietic stem cells", Bioprocess Biosyst. Eng., 2003, 25(6):365-369.
Da Silva, et al., "A human stromal-based serum-free culture system supports the ex vivo expansion/maintenance of bone marrow and cord blood hematopoietic stem/progenitor cells", Experimental Hematology, 2005, 33(7):828-835.
Da Silva, et al., "Differences Amid Bone Marrow and Cord Blood Hematopoietic Stem/Progenitor Cell Division Kinetics", J. Cell. Physiol., 2009, 220(1):102-111.
Da Silva, et al., "Dynamic cell-cell interactions between cord blood haematopoietic progenitors and the cellular niche are essential for expansion of $CD_{34}+$, $CD_{34}+CD_{38}-$ and early lymphoid $CD_7+$ cells", J Tissue Eng Regen Med, 2010, 4(2):149-158.
Denning-Kendall, et al., "Cobblestone Area-Forming Cells in Human Cord Blood Are Heterogeneous and Differ from Long-Term Culture-Initiating Cells", Stem Cells, 2003, 21:694-701.
De Wynter, et al., "CD34+AC133+ Cells Isolated from Cord Blood are Highly Enriched in Long-Term Culture-Initiating Cells, NOD/SCID-Repopulating Cells and Dendritic Cell Progenitors", Stem Cells, 1998, 16:387-396.
Drewitz, et al., "Towards automated production and drug sensitivity testing using scaffold-free spherical tumor microtissues", Biotechnol. J., 2011, 6:1488-1496.

Duchez, et al., "Definitive Setup of Clinical Scale Procedure for Ex Vivo Expansion of Cord Blood Hematopoietic Cells for Transplantation", Cell Transplantation, 2012, 21:2517-2521.
Frias, et al., "Generation of functional natural killer and dendritic cells in a human stromal-based serum-free culture system designed for cord blood expansion", Experimental Hematology, 2008, 36:61-68.
Giebel, et al., "Segregation of lipid raft markers including CD133 in polarized human hematopoietic stem and progenitor cells", Blood, 2004, 104(8):2332-2338.
Giebel, et al., "Primitive human hematopoietic cells give rise to differentially specified daughter cells upon their initial cell division", Blood, 2006, 107(5):2146-2152.
Giebel and Beckmann, "Asymmetric Cell Divisions of Human Hematopoietic Stem and Progenitor Cells Meet Endosomes", Cell Cycle, 2007, 6(18):2201-2204.
Giebel, et al., "Cell Polarity and Asymmetric Cell Division within Human Hematopoietic Stem and Progenitor Cells", Cells Tissues Organs, 2008, 188:116-126.
Gluckman, et al., "Hematopoietic Reconstitution in a Patient With Fanconi's Anemia by Means of Umbilical-Cord Blood From an HLA-Identical Sibling", The New England Journal of Medicine, 1989, 321(17):1174-1178.
Goncalves, et al., "Kinetic analysis of the ex vivo expansion of human hematopoietic stem/progenitor cells", Biotechnology Letters, 2006, 28:335-340.
Goncalves, et al., "A Stro-1+ human universal stromal feeder layer to expand/maintain human bone marrow hematopoietic stem/progenitor cells in a serum-free culture system", Experimental Hematology, 2006, 34:1353-1359.
Gorgens, et al., "Lipid raft redistribution and morphological cell polarization are separable processes providing a basis for hematopoietic stem and progenitor cell migration", Int. J. Biochem. Cell Biol., 2012, 44:1121-1132.
Gunn, "Hereditary Acholuric Jaundice in the Rat", Canadian Medical Association Journal, 1944, 50:230-237.
Harrison, et al., "Relative to adult marrow, fetal liver repopulates nearly five times more effectively long-term than short-term", Experimental Hematology, 1997, 25:293-297.
Hofmann, et al., "A Fiber-Optic-Based Imaging System for Nondestructive Assessment of Cell-Seeded Tissue-Engineered Scaffolds", Tissue Engineering: Part C, 2012, 18(9):677-687.
Hoggatt, et al., "Prostaglandin $E_2$ enhances hematopoietic stem cell homing, survival, and proliferation", Blood, 2009, 113:5444-5455.
Katsuda, et al., "Biliary Epithelial Cells Play an Essential Role in the Reconstruction of Hepatic Tissue with a Functional Bile Ductular Network", Tissue Engineering: Part A, 2013, 19:2402-2411.
Khetani and Bhatia, "Microscale culture of human liver cells for drug development", Nature Biotechnology, 2008, 26(1):120-126.
Koh and Chao, "Haploidentical hematopoietic cell transplantation", Bone Marrow Transplantation, 2008, 42:S60-S63.
Kubota and Reid, "Clonogenic hepatoblasts, common precursors for hepatocytic and biliary lineages, are lacking classical major histocompatibility complex class I antigen", PNAS, 2000, 97(22):12132-12137.
Lang, et al., "Three-dimensional culture of hepatocytes on porcine liver tissue-derived extracellular matrix", Biomaterials, 2011, 32:7042-7052.
Lathia, et al., "Distribution of CD133 reveals glioma stem cells self-renew through symmetric and asymmetric cell divisions", Cell Death and Disease, 2011, 2:1-11.
Li, et al., "Human umbilical vein endothelial cells increase ex vivo expansion of human CD34+ PBPC through IL-6 secretion", Cytotherapy, 2006, 8(4):335-342.
Liu, et al., "Initial division behavior of cord blood hematopoietic stem cells depends on microenvironment", Chin J Hematol., 2002, 23(10):534-537.
Macdonald, et al., "Liver Cell Culture and Lineage Biology", Methods of Tissue Engineering, 2002, 11:151-201.
Magin, et al., "Primary Cells as Feeder Cells for Coculture Expansion of Human Hematopoietic Stem Cells from Umbilical Cord Blood—A Comparative Study", Stem Cells and Development, 2009, 18(1):173-186.

(56) References Cited

OTHER PUBLICATIONS

Martin and Bhatia, "Analysis of the Human Fetal Liver Hematopoietic Microenvironment", Stem Cells and Development, 2005, 14:493-504.
Matsumoto, et al., "In Vitro Proliferation Potential of AC133 Positive Cells in Peripheral Blood", Stem Cells, 2000, 18:196-203.
Mazziotti, et al., "Anomalous Development of the Hepatobiliary System in the Inv Mouse", Hepatology, 1999, 30(2):372-378.
Mcniece, et al., "Ex vivo expansion of cord blood mononuclear cells on mesenchymal stem cells", Cytotherapy, 2004, 6(4):311-317.
Mikkola and Orkin, "The journey of developing hematopoietic stem cells", Development, 2006, 133:3733-3744.
Minguet, et al., "A population of c-Kitlow(CD45/TER119)-hepatic cell progenitors of 11-day postcoitus mouse embryo liver reconstitutes cell-depleted liver organoids", Journal of Clinical Investigation, vol. 112, No. 8, Oct. 15, 2003, pp. 1152-1163.
Morrison, et al., "The purification and characterization of fetal liver hematopoietic stem cells", PNAS, 1995, 92:10302-10306.
Mortera-Blanco, et al., "Long-term cytokine-free expansion of cord blood mononuclear cells in three-dimensional scaffolds", Biomaterials, 2011, 32:9263-9270.
Norkin, et al., "Umbilical cord blood graft enhancement strategies: has the time come to move these into the clinic?", Bone Marrow Transplantation, 2013, 48:884-889.
Porada and Almeida-Porada, "Mesenchymal stem cells as therapeutics and vehicles for gene and drug delivery", Advanced Drug Delivery Reviews, 2010, 62:1156-1166.
Porada, et al., "Development and Validation of a Novel, High-Throughput Colony-Forming Assay That Allows Simultaneous Detection and Quantitation of Seven Primitive Sheep Hematopoietic Populations", Blood, 2007, 110(11).
Porada et al., "Adult Mesenchymal Stem Cells: A Pluripotent Population with Multiple Applications", Current Stem Cell Research & Therapy, 2006, 1:231-238.
Punzel, et al., "The symmetry of initial divisions of human hematopoietic progenitors is altered only by the cellular microenvironment", Experimental Hematology, 2003, 31:339-347.
Qiu, et al., "Ex Vivo Expansion of CD34+ Umbilical Cord Blood Cells in a Defined Serum-Free Medium (QBSF-60) with Early Effect Cytokines", Journal of Hematotherapy & Stem Cell Research, 1999, 8:609-618.
Schmeichel, et al., "Structural Cues from the Tissue Microenvironment Are Essential Determinants of the Human Mammary Epithelial Cell Phenotype", Journal of Mammary Gland Biology and Neoplasia, 1998, 3(2):201-213.
Schuster, et al., "Expansion of hematopoietic stem cells for transplantation: current perspectives", Experimental Hematology & Oncology, 2012, 1(12):1-6.
Seok, et al., "Genomic responses in mouse models poorly mimic human inflammatory diseases", PNAS, 2013, 110(9):3507-3512.
Suzuki, et al., "Role for growth factors and extracellular matrix in controlling differentiation of prospectively isolated hepatic stem cells", Development, 2003, 130:2513-2524.
Szabo, et al., "Direct conversion of human fibroblasts to multilineage blood progenitors", Nature, 2010, 468:521-528.
Takebe, et al., "Vascularized and functional human liver from an iPSC-derived organ bud transplant", Nature, 2013, 499:481-485.
Tateno, et al., "Near Completely Humanized Liver in Mice Shows Human-Type Metabolic Responses to Drugs", Am J Pathol, 2004, 165(3):901-912.
Tiwari, et al., "Ex vivo expansion of haematopoietic stem/progenitor cells from human umbilical cord blood on acellular scaffolds prepared from MS-5 stromal cell line", J Tissue Eng Regen Med, 2013, 7:871-883.
Tung, et al., "Ex vivo expansion of umbilical cord blood for transplantation", Best Practice & Research Clinical Haematology, 2010, 23(2):245-257.
Verfaillie, et al., "Kinetics of engraftment of CD34− and CD34+ cells from mobilized blood differs from that of CD34− and CD34+ cells from bone marrow", Experimental Hematology, 2000, 28:1071-1079.
Walasek, et al., "Hematopoietic stem cell expansion: challenges and opportunities", Ann. N.Y. Acad. Sci., 2012, 1266:138-150.
Wu, et al., "Imaging Hematopoietic Precursor Division in Real Time", Cell Stem Cell, 2007, 1:541-554.
Yin, et al., "AC133, a Novel Marker for Human Hematopoietic Stem and Progenitor Cells", Blood, 1997, 90(12):5002-5012.
Zschenker, et al., "Genome-Wide Gene Expression Analysis in Cancer Cells Reveals 3D Growth to Affect ECM and Processes Associated with Cell Adhesion but Not DNA Repair", PLOS ONE, 7(4):1-9.
Chou, "Fetal liver hepatic progenitors are supportive stromal cells for hematopoietic stem cells", Proc Natl Acad Sci USA, vol. 107, Issue 17, 2010, pp. 7799-7804.
EP Application No. EP14706251.7, "Notice of Decision to Grant", dated Oct. 18, 2018, 2 pages.
EP Application No. EP14706251.7, "Office Action", dated Sep. 26, 2016, 4 pages.
EP Application No. EP14706251.7, "Office Action", dated Sep. 29, 2017, 4 pages.
EP Application No. EP14706251.7, "Office Action", dated Feb. 20, 2017, 6 pages.
Minguet et al., "A Population of C-Kit Low (CD45/TER119)-Hepatic Cell Progenitors of 11-day Postcoitus Mouse Embryo Liver Reconstitutes Cell-Depleted Liver Organoids", The Journal of Clinical Investigation, vol. 112, No. 8, 2003, pp. 1152-1163.
PCT/US2014/016331, "International Search Report and Written Opinion", dated May 22, 2014, 12 pages.
Sugiyama et al., "Embryonic Regulation of the Mouse Hematopoietic Niche", The Scientific World Journal, vol. 11, No. 1, 2011, pp. 51-1780.
Takeuchi, "Cultivation of aorta-gonad-mesonephros-derived hematopoietic stem cells in the fetal liver microenvironment amplifies long-term repopulating activity and enhances engraftment to the bone marrow", Blood, vol. 99, No. 4, Feb. 15, 2002, pp. 1190-1196.
Uygun et al., "Organ reengineering through development of a transplantable recellularized liver graft using decellularized liver matrix", Nature Medicine, vol. 16, No. 7, Jul. 2010, pp. 814-820.

* cited by examiner

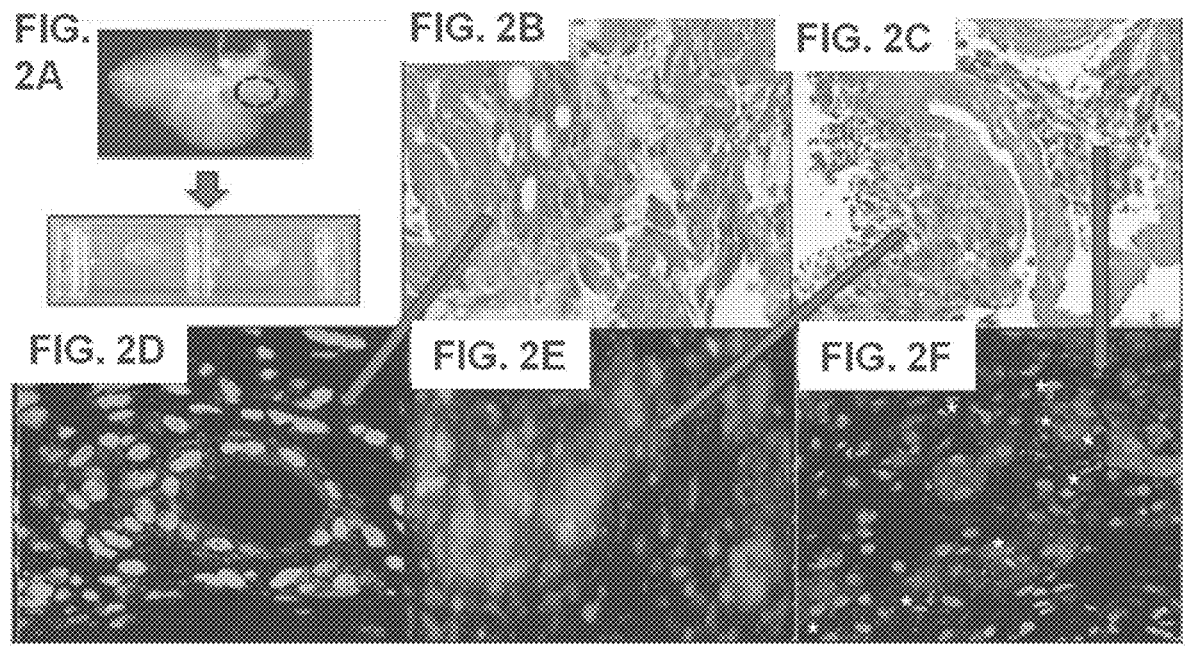
FIG. 2G
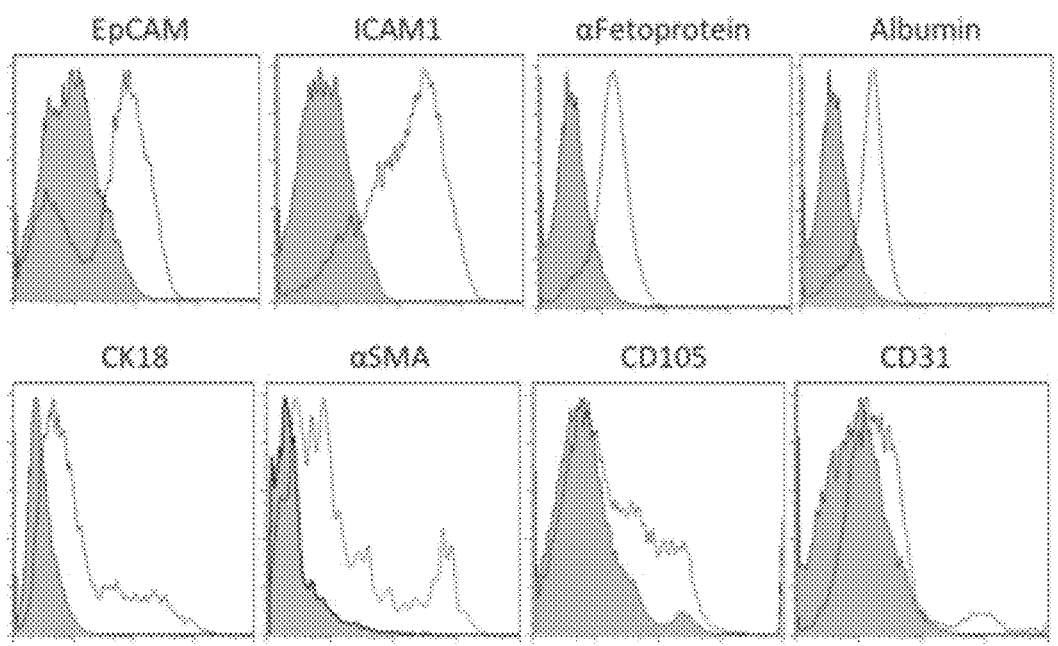

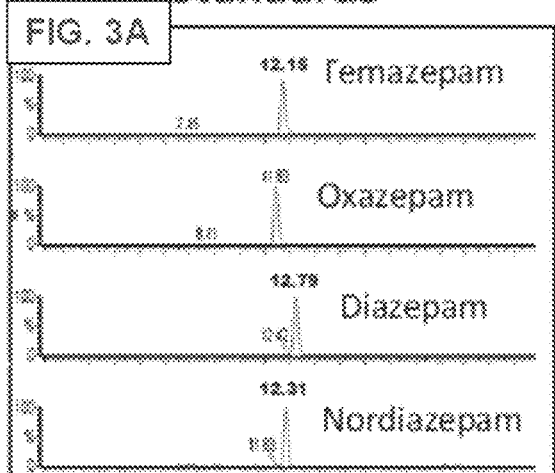
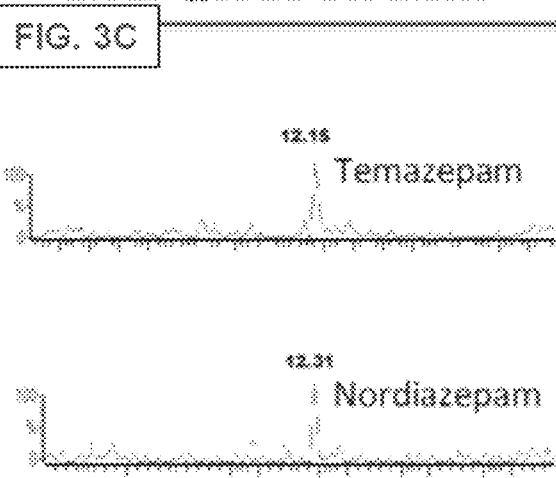
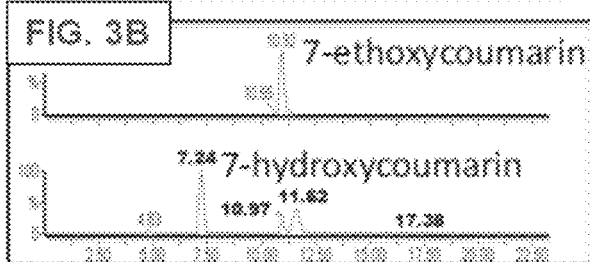
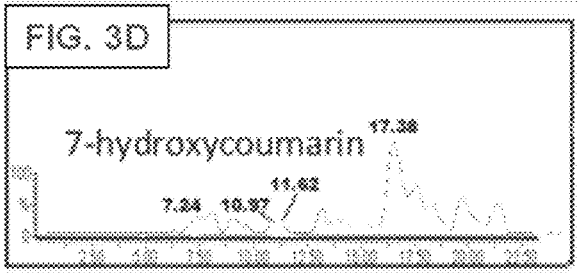
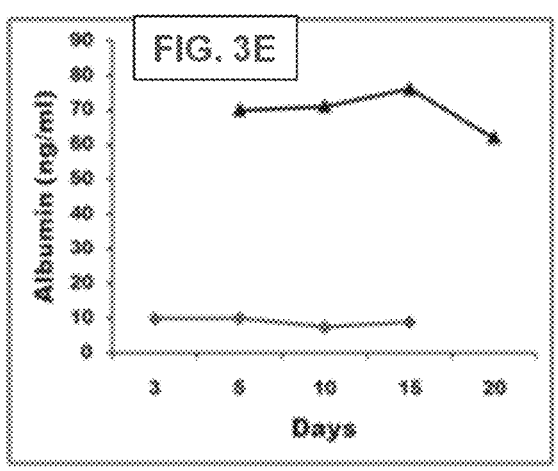
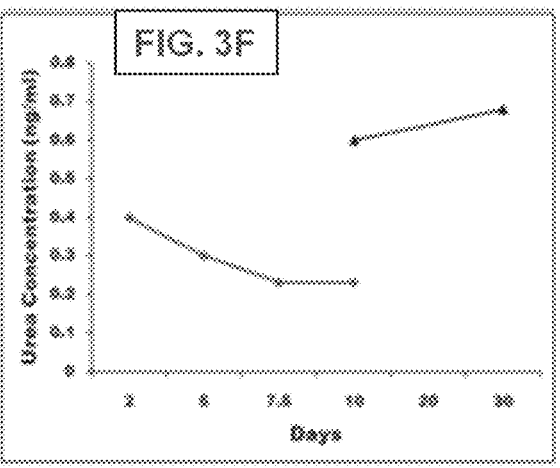

| Metabolites | 1 week culture | | | | 3 week culture | | | |
|---|---|---|---|---|---|---|---|---|
| | Time (hours) | | | | Time (hours) | | | |
| | 3 | 6 | 12 | 24 | 3 | 6 | 12 | 24 |
| Temazepam | − | + | + | + | + | + | + | + |
| Nordiazepam | − | − | + | + | − | + | + | + |
| 7-OH coumarin | − | − | + | + | − | − | − | + |

BIOENGINEERED LIVER CONSTRUCTS AND METHODS RELATING THERETO

CROSS-REFERENCE TO RELATED APPLICATIONS

The present application is a § 371 national stage application of International Application PCT/US2014/016331, filed Feb. 13, 2014, which claims the benefit of priority to U.S. Provisional Patent Application Ser. No. 61/764,174, filed Feb. 13, 2013. The disclosure of both these applications is hereby incorporated by reference in their entirety herein.

STATEMENT AS TO RIGHTS TO INVENTIONS MADE UNDER FEDERALLY SPONSORED RESEARCH AND DEVELOPMENT

This invention was made with government support under Grant No. 1R21HL117704 from the NIH/National Heart, Lung, and Blood Institute. The government has certain rights in this invention.

FIELD OF THE INVENTION

The present invention concerns to bioengineered liver constructs, methods of making such constructs, and method of using such constructs.

BACKGROUND

Cellular and tissue models that better mimic human liver developmental biology and physiology of interest to advance understanding of disease origin and progression, and aid in the pursue of better treatments. Until recently, most of the available models were predominantly standard 2-D in vitro cell culture systems or in vivo animal models (rodents). However, these models don't consistently match tissue development, or the physiologic processes, observed in the human body. These deficiencies fostered the creation of humanized animal liver models that can reproduce to some extent specific human drug metabolism, pathogen-host interaction and disease modeling [70-72]. However, none of these humanized animal liver models produced complete recapitulation of liver developmental biology or accurate physiological inflammatory responses [73], limiting their applications to a post-developmental stage and preventing their usage in the study of human hepato-biliary organogenesis mechanisms and associated diseases. For these reasons, novel methods of human hepatic micro-tissue generation have been developed in the last years, creating hepatic tissue in vitro that displays human specific metabolic and physiologic responses [74-77]. Nevertheless, these model systems suffer from some of the same limitations that plague the described animal models: none displays progressive hepato-biliary organogenesis that recapitulates human liver development, most of them lacking biliary tissue altogether. Most of these models focus on the mature functions of the bioengineered tissues.

Tissue engineering strategies have been developed for the generation of functional liver tissue using decellularized liver scaffolds repopulated with liver cells [9-12, 70-72, 78]. The decellularized liver bioscaffold offers several advantages over widely used synthetic polymer 3D scaffolds. The preservation of intact native vascular channels can be used to deliver cells into the parenchyma, culture media with nutrients and oxygen to the newly generated tissue, and subsequently anastomosed to the host vascular system. The retention of important ECM molecules in their native configuration can allow for site specific engraftment of different cell types along with providing signals that direct polarization, migration, proliferation, survival and differentiation [9-11]. Human fetal liver progenitor cells (hFLPCs) isolated from fetal livers can be used as a recellularized cell source due to their capability of differentiating into hepatocytes and cholangiocytes [9, 10].

One aspect of human fetal liver development is its role in hematopoiesis. The hematopoietic system is made up of all adult blood cell types and cells of the myeloid and lymphoid lineages. All of these cells are derived from multipotent hematopoietic stem cells (HSC) through a succession of precursors with progressively limited potential. HSC are tissue-specific stem cells that exhibit remarkable proliferative and self-renewal capacity and are responsible for the life-long maintenance of the hematopoietic system. HSCs are rare cells that reside in adult bone marrow where hematopoiesis is continuously taking place. They can also be found in cord blood, fetal liver, adult spleen, and peripheral blood. Human adult HSCs are largely quiescent and undergo limited self-renewal. This is in contrast to the higher frequency of cycling HSCs undergoing self-renewal during fetal development when hematopoiesis is transiently localized to the fetal liver.

It is well known that, during development, the fetal liver is the main site of HSC expansion and differentiation [13]. In contrast to the adult bone marrow, in which the vast majority of primitive HSC are quiescent in steady-state hematopoiesis, during the stage in development when the fetal liver is responsible for maintaining hematopoiesis, a dramatic increase in the absolute number of mature progeny occurs to meet the increasing hematopoietic demands of the rapidly growing fetus, yet the number of long-term repopulating HSC is maintained with remarkable precision. Within the fetal liver, HSC actively cycle and these cells outcompete adult HSC upon transplantation [13, 14]. Prior studies have shown that the initial divisional behavior of CB-HSPC is highly dependent upon their surrounding environment [17]. Asymmetric division is regulated by cell polarity, with specific components of the cell membrane, cytoplasmic constituents, and even nuclear contents being unevenly distributed throughout the stem cell such that, upon division, two daughter cells of differing composition are created [50-52]. Conversely, at other stages of development, the fetal liver also appears to harbor the ability to support true expansion of HSC via symmetric renewal, in which both daughter cells are bona fide HSC. For example, the stromal cell line AFT024 and fetal hepatoblasts, both of murine origin, have been shown, in 2-D cultures, to effectively preserve the self-renewal capacity of human and mouse HSC, respectively [17, 18]. Thus, within the hepatic tissue, cellular niches exist that promote asymmetric or symmetric self-renewal divisions, leading to maintenance or expansion of primitive HSC [15, 16]. In addition, the initial divisional behavior of HSPC isolated from cord blood is highly dependent upon the environment [17].

HSC transplantation (HSCT) provides the only curative treatment for a wide variety of malignant and nonmalignant hematologic disorders (e.g., bone marrow failure states such as myelodysplastic syndrome, metabolic storage diseases, and hemoglobinopathies). HSCT are preferred over transplantations using more differentiated cells (e.g., hematopoietic progenitor cells (HPC)), which have an increased risk of failure long-term. HSCTs are either autologous (using the subject's own cells) or allogeneic (using donor stem cells, typically from matched donor).

Common sources of HSC for transplantation are bone marrow, peripheral blood, and umbilical cord blood (CB). Many studies of allogeneic bone marrow transplantation have shown that a higher dose of marrow cells correlates with more robust hematopoietic engraftment and lower mortality from infectious complications. Peripheral blood stem cells (PBSC) collected after mobilization with granulocyte colony stimulating factor (G-CSF) contain a larger number of CD34-positive (CD34) progenitors and total cells than bone marrow, which may lead to lower mortality compared to transplantation of bone marrow. However, the higher T cell content of PBSC may also lead to increased incidence and severity of acute and chronic graft-versus-host disease (GVHD). This concern is especially serious when the donor is unrelated to the recipient. Currently, peripheral blood stem cells are the most common source of HSCs for allogeneic HSCT. However, 60-70% of the patients in need of a HSCT do not have a suitable human leukocyte antigen (HLA) matched donor.

CB has the potential to become an ideal hematopoietic stem cell (HSC) source to address limitations in donor availability due to its ready availability in CB banks and lower risk of transmitting viral infections or inducing GVHD in HLA mismatched recipients. However, the limited number of HSC in a single CB unit leads to an increased risk of graft failure, delayed hematological recovery (engraftment) and prolonged immunosuppression, particularly in adult patients. To compensate for low HSC counts per unit, infusion of two unrelated umbilical CB units—also known as "double UCB transplantation (dUCBT)"—is sometimes utilized, but early post-transplant complications remain unacceptably high. Several other strategies, such as optimization of myeloablative conditioning, increasing HPC yield at collection, minimization of HPC loss during processing and thaw, and ex vivo CB manipulations to enhance engraftment capacity, can also lead to improved rates of engraftment and faster neutrophil recovery.

Increasing the availability of HSC would clearly be advantageous to improving HSCT patient outcomes. Successful in vitro expansion of HSC for practical clinical purposes should meet the following criteria: (1) HSCs must be able to expand on a larger scale without sacrificing their self-renewal ability; and (2) expanded HSC must be safe and transplantable, and requires the method to be free of feeder cells, serum proteins, or microbial agents. HSC expansion is challenging due to the fact that culturing HSC results in differentiation of the cells into progenitor cells in the hematopoiesis lineages. Although HSC will rapidly expand after in vivo transplantation, experience from in vitro studies indicates that control of HSC self-renewal and differentiation in culture remains difficult. Protocols based on hematopoietic cytokines have failed to support reliable amplification of immature stem cells in culture, suggesting that additional factors are required. Current methods of ex vivo HSC expansion include the use of cytokine cocktails, copper chelators [1], exposure to signaling molecules, stromal support and overexpression of transcription factors [26, 27], which have been reported to affect HSC self-renewal and have improved ex vivo HSC expansion [62, 63]. However, most advances utilizing these various techniques are restricted to murine models [62]. Also, despite the advancements made in CB-HSC expansion, challenges remain regarding the ability to obtain, from a single CB unit, sufficient numbers of both long- and short-term repopulating cells for treatment of adolescents and adults [1, 2].

Previous efforts have shown that CB-HSPC can be expanded and the differentiation of these cells can be driven towards both the myeloid and lymphoid lineages in a serum-free culture system using a feeder layer of adult human bone marrow-derived stromal cells [3-6]. Initial progenitor content and cytokine concentrations for ex vivo expansion in 2-D cultures have also been assessed [6-8], and demonstrated that the expanded cells had the ability to engraft pre-immune fetal sheep [4]. However, while the absolute number of long-term engrafting HSC increased in this culture system, the relative percentage of these most primitive stem cells decreased with time (i.e., limited expansion of CB-HSPC, or exhaustion of the hematopoietic stem cell pool) [2, 3, 23-25]. Some success has been achieved with culturing CB CD34+ cells in suspension cultures in the presence of particular cytokines [64].

As such, there remains a need for improved methods of generating HSC and other hematopoietic cells for transplantation in sufficient quantities and with characteristics likely to lead to engraftment.

BRIEF SUMMARY

One aspect of the invention is a liver organoid comprising a bioscaffold derived from a decellularized donor subject liver comprising a native extracellular matrix (ECM) and native vascular channels; and liver cells having predominately fetal characteristics. The liver cells may comprise at least one of liver progenitor cells, hepatoblasts, vascular cells, cholangiocytes, or stromal cells. The vascular cells may comprise at least one of liver endothelial cells, liver sinusodial cells, vascular smooth muscle cells, or pericytes. The hepatoblasts may comprise at least one of fetal liver hepatoblasts, hepatoblasts derived from adult-derived liver stem cells, hepatoblasts derived from induced pluripotent stem cells, or hepatoblasts derived from embryonic stem cells. The liver cells may comprise an enriched fetal liver progenitor cell population comprising at least about 55-75% hepatic cells and not more than about 15-25% stromal cells and not more than about 5-15% endothelial cells. The liver cells may comprise an enriched fetal liver progenitor cell population comprising about 55-75% hepatic cells, about 15-25% stromal cells, about 5-15% endothelial cells. The liver cells may express at least one of α-fetoprotein or CYP3A7. The hepatic cells may comprise fetal liver progenitor cells.

Another aspect of the invention is a liver organoid comprising a bioscaffold derived from a decellularized donor subject liver comprising a native extracellular matrix (ECM) and native vascular channels; and liver cells having adult characteristics. The liver cells may comprise at least one of hepatoblasts, hepatocytes, vascular cells, cholangiocytes, or stromal cells. The vascular cells may comprise at least one of liver endothelial cells, liver sinusodial cells, vascular smooth muscle cells, or pericytes. The hepatocytes may be derived from at least one of fetal liver hepatoblasts, hepatoblasts derived from adult-derived liver stem cells, hepatoblasts derived from induced pluripotent stem cells, or hepatoblasts derived from embryonic stem cells. The liver organoid may comprise hepatocytic cell clusters and biliary ducts. The liver cells may express albumin. The liver cells may express at least one cytochrome P450 isoform. The liver cells may express at least one of CK7, CK19, transferrin, CYP3A4, HNF4 α, AST, ALT, TAT, CYP2E1 or A1AT. The liver cells may synthesize urea.

In another aspect, the invention is a method of generating a liver organoid comprising the steps of providing a bioscaffold derived from a decellularized donor subject liver comprising a native extracellular matrix (ECM) and native vascular channels, seeding the bioscaffold with liver cells; and culturing the liver cells with culture medium containing at least one growth factor to generate a liver organoid comprising differentiated liver cells over time. The liver cells may comprise at least one of hepatoblasts, hepatocytes, vascular cells, cholangiocytes, or stromal cells. The vascular cells may comprise at least one of liver endothelial cells, liver sinusodial cells, vascular smooth muscle cells, or pericytes. The hepatoblasts may comprise at least one of fetal liver hepatoblasts, hepatoblasts derived from adult-derived liver stem cells, hepatoblasts derived from induced pluripotent stem cells, or hepatoblasts derived from embryonic stem cells. The liver cells of step (b) may comprise an enriched fetal liver progenitor cell population comprising at least about 55-75% hepatic cells and not more than about 15-25% stromal cells and not more than about 5-15% endothelial cells. The liver cells of step (b) may comprise an enriched fetal liver progenitor cell population comprising about 55-75% hepatic cells, about 15-25% stromal cells, about 5-15% endothelial cells. The hepatic cells may comprise fetal liver progenitor cells. The liver organoid may comprise hepatocytic cell clusters and biliary ducts. The differentiated liver cells of step (c) may express albumin. The differentiated liver cells of step (c) may express at least one cytochrome P450 isoform. The culture medium of step (c) may comprise oncostatin M. The culture medium of step (c) may comprise at least one of dexamethasone, cyclic adenosine monophosphate (cAMP), Prolactin, Glucagon, niacinamide, α-lipoic acid, triiodothyronine, free fatty acids, epidermal growth factor (EGF), high-density lipoprotein (HDL), hepatocyte growth factor (HGF), fibroblast growth factor (FGF), or human growth hormone (HGH).

Another aspect of the invention is a liver organoid comprising a bioscaffold derived from a decellularized donor subject liver comprising a native extracellular matrix (ECM) and native vascular channels; and liver cells comprising at least one micro-environment niche that supports hematopoietic stem cell (HSC) expansion or differentiation. The at least one micro-environment niche may support expansion or differentiation of at least one of HSC obtained from cord blood, HSC obtained from bone marrow, HSC derived from induced pluripotent stem cells, HSC derived from embryonic stem cells, or HSC derived from direct reprogramming of adult somatic cells. In some embodiments, the liver cells of the liver organoid comprise at least two micro-environment niches, wherein in at least one micro-environment niche supports HSC expansion and at least one micro-environment niche supports HSC differentiation. The liver cells of the liver organoid may be fetal liver cells. Further, the liver cells may be at least one of liver progenitor cells, hepatoblasts, vascular cells, cholangiocytes, or stromal cells. In some aspects, the vascular cells may be at least one of liver endothelial cells, liver sinusoidal cells, smooth muscle cells, or pericytes. The hepatoblasts may be at least one of fetal liver hepatoblasts, hepatoblasts derived from adult-derived liver stem cells, hepatoblasts derived from induced pluripotent stem cells, or hepatoblasts derived from embryonic stem cells. In some embodiments, the at least one micro-environment niche supports expansion or differentiation of at least one of HSC obtained from cord blood, HSC obtained from bone marrow, HSC derived from induced pluripotent stem cells, HSC derived from embryonic stem cells, or HSC derived from direct reprogramming of adult somatic cells.

A further aspect of the invention is a method of generating the liver organoid using a bioscaffold derived from a decellularized liver from a donor subject that retains the native extracellular matrix and native vascular channels. The method includes the steps of: providing a bioscaffold derived from a decellularized donor subject liver comprising an extracellular matrix (ECM) and native vascular channels; seeding the bioscaffold with liver cells; culturing the liver cells with the bioscaffold in the presence of culture media for sufficient time to produce at least one micro-environment niche in the bioscaffold that supports hematopoietic stem cell (HSC) expansion or differentiation. In some embodiments, the liver cells are cultured with the bioscaffold in the presence of culture media for sufficient time to produce at least two micro-environment niches in the bioscaffold, wherein at least one micro-environment niche supports HSC expansion and at least one micro-environment niche supports HSC differentiation. In various embodiments, the liver cells of the liver organoid are as described in the previous paragraph. In some embodiments, the liver cells seeded on the organoids comprise an enriched fetal liver progenitor cell population containing at least about 55-75% hepatic cells, not more than about 15-25% stromal cells and not more than about 5-15% endothelial cells. In some embodiments, these liver cells comprise an enriched fetal liver progenitor cell population containing about 55-75% hepatic cells, about 15-25% stromal cells, and about 5-15% endothelial cells. In some embodiments, the hepatic cells may comprise fetal liver progenitor cells. In some embodiments, the liver cells seeded on the organoid may be cultured in culture media comprising at least one of epidermal growth factor (EGF), hepatocyte growth factor (HGF), insulin-like growth factor 1 (IGF-1), glycogen synthase kinase-3beta inhibitor (GSK3βi), or thiazovivin. The at least one micro-environment niche may support expansion or differentiation of at least one of HSC obtained from cord blood, HSC obtained from bone marrow, HSC derived from induced pluripotent stem cells, HSC derived from embryonic stem cells, or HSC derived from direct reprogramming of adult somatic cells. In some embodiments, the liver cells seeded on the organoid may be cultured for about 5 days. In some embodiments, the culture media for culturing the HSC cells may contain at least one exogenous factor. For example, in some embodiments, the media contains at least one of stem cell factor (SCF), interleukin-6 (IL-6), or Fms-like tyrosine kinase 3 (FLT3), oncostatin-M (OSM), TGFβ3, Jagged-1, fetal bovine serum (FBS), dexamethasone, cyclic adenosine monophosphate (cAMP), Prolactin, Glucagon, niacinamide, α-lipoic acid, triiodothyronine, epidermal growth factor (EGF), high-density lipoprotein (HDL), leukemia inhibitory factor (LIF), hepatocyte growth factor (HGF), fibroblast growth factor (FGF), or human growth hormone (HGH). In some embodiments, the media may comprise at least one of stem cell factor (SCF), fibroblast growth factor (FGF), interleukin-6 (IL-6), Fms-like tyrosine kinase 3 (FLT3), or leukemia inhibitory factor (LIF). In certain embodiments, factors added to the culture media are human factors. In some embodiments, the liver organoid is seeded with at least one of HSC obtained from cord blood, HSC obtained from bone marrow, HSC derived from induced pluripotent stem cells, HSC derived from embryonic stem cells, or HSC derived from direct reprogramming of adult somatic cells. The differentiated hematopoietic cells may comprise hematopoietic progenitor cells (HPC), myeloid progenitor cells (MPC), lymphoid progenitor cells (LPC), lymphocytes, granulocytes, macrophages, erythrocytes, or platelets. The differentiated hematopoietic cells comprise an enriched population of differentiated erythrocytes and the culture media may comprise erythropoietin (EPO).

An additional aspect of the invention is a method of producing hematopoietic cells using the liver organoid described herein. The method includes the steps of: obtaining a liver organoid comprising a bioscaffold derived from a decellularized donor subject liver comprising a native extracellular matrix (ECM) and native vascular channels and liver cells comprising at least one micro-environment niche that supports hematopoietic stem cell (HSC) expansion or differentiation; seeding the liver organoid with HSC; culturing the HSC on the liver organoid with culture media; and collecting expanded HSC and/or differentiated hematopoietic cells from the culture media. In some embodiments, the liver organoid comprises (i) a bioscaffold derived from a decellularized donor subject liver comprising a native extracellular matrix (ECM) and native vascular channels and (ii) liver cells comprising at least two micro-environment niches, wherein at least one micro-environment niche supports HSC expansion and at least one micro-environment niche supports HSC differentiation. The method enables collection of differentiated hematopoietic cells, including hematopoietic progenitor cells (HPC), myeloid progenitor cells (MPC), lymphoid progenitor cells (LPC), lymphocytes, granulocytes, macrophages, erythrocytes, or platelets. In some embodiments, the culture media does not include growth factors and/or cytokines. The culture media may exclude growth factors when expanded HSC and/or immature hematopoietic stem cells are collected from the culture media. For example the culture media that excludes growth factors may contain at least one of stem cell factor (SCF), fibroblast growth factor (FGF), interleukin-6 (IL-6), Fms-like tyrosine kinase 3 (FLT3), or leukemia inhibitory factor (LIF). The culture media may contain at least one growth factor when differentiated hematopoietic stem cells, such as, e.g., hematopoietic progenitor cells (HPC), myeloid progenitor cells (MPC), lymphoid progenitor cells (LPC), lymphocytes, granulocytes, macrophages, erythrocytes, or platelets, are collected in from the culture media. For example, the culture media containing at least one growth factor may contain at least one of stem cell factor (SCF), interleukin-6 (IL-6), or Fms-like tyrosine kinase 3 (FLT3), oncostatin-M (OSM), TGFβ3, Jagged-1, fetal bovine serum (FBS), dexamethasone, cyclic adenosine monophosphate (cAMP), Prolactin, Glucagon, niacinamide, α-lipoic acid, triiodothyronine, epidermal growth factor (EGF), high-density lipoprotein (HDL), leukemia inhibitory factor (LIF), hepatocyte growth factor (HGF), fibroblast growth factor (FGF), or human growth hormone (HGH). For example the culture media may contain at least one of stem cell factor (SCF), fibroblast growth factor (FGF), interleukin-6 (IL-6), Fms-like tyrosine kinase 3 (FLT3), or leukemia inhibitory factor (LIF). In some embodiments, an enriched population of differentiated erythrocytes is collected. Where differentiation of erythrocytes is desired, the culture media will at least include erythropoietin (EPO). In certain embodiments, the culture media is serum-free culture media. The liver organoid may be seeded with at least one of HSC obtained from cord blood, HSC obtained from bone marrow, HSC derived from induced pluripotent stem cells, HSC derived from embryonic stem cells, or HSC derived from direct reprogramming of adult somatic cells.

Another aspect of the invention is a cell population comprising hematopoietic cells produced by a process comprising (a) obtaining a liver organoid comprising (i) a bioscaffold derived from a decellularized donor subject liver comprising a native extracellular matrix (ECM) and native vascular channels and (ii) liver cells comprising at least one micro-environment niche that supports hematopoietic stem cell (HSC) expansion or differentiation, (b) seeding the liver organoid with HSC, (c) culturing the HSC on the liver organoid with culture media; and (d) collecting hematopoietic cells from the culture media. The hematopoietic cells may comprise expanded HSC and/or differentiated hematopoietic cells. The organoid may comprise (i) a bioscaffold derived from a decellularized donor subject liver comprising a native extracellular matrix (ECM) and native vascular network and (ii) liver cells comprising at least two micro-environment niches, wherein at least one micro-environment niche supports HSC expansion and at least one micro-environment niche supports HSC differentiation. The liver cells of step (a) may comprise fetal liver cells. The liver cells of step (a) may comprise at least one of liver progenitor cells, hepatoblasts, vascular cells, cholangiocytes, or stromal cells. The vascular cells may comprise at least one of liver endothelial cells, liver sinusodial cells, vascular smooth muscle cells, or pericytes. The hepatoblasts may comprise at least one of fetal liver hepatoblasts, hepatoblasts derived from adult-derived liver stem cells, hepatoblasts derived from induced pluripotent stem cells, or hepatoblasts derived from embryonic stem cells. The liver cells of step (a) may comprise an enriched fetal liver progenitor cell population comprising at least about 55-75% hepatic cells and not more than about 15-25% stromal cells and not more than about 5-15% endothelial cells. The liver cells of step (a) may comprise an enriched fetal liver progenitor cell population comprising about 55-75% hepatic cells, about 15-25% stromal cells, about 5-15% endothelial cells. The hepatic cells may comprise fetal liver progenitor cells. The liver cells seeded on the bioscaffold in step (b) may be cultured in culture media comprising at least one of epidermal growth factor (EGF), hepatocyte growth factor (HGF), insulin-like growth factor 1 (IGF-1), glycogen synthase kinase-3beta inhibitor (GSK3βi), or thiazovivin. The liver cells seeded on the bioscaffold in step (b) may be cultured for about 5 days. The culture media in step (c) may exclude exogenous growth factors, and wherein expanded HSC and/or immature hematopoietic stem cells are collected in step (d). The culture media in step (c) may comprise at least one of stem cell factor (SCF), fibroblast growth factor (FGF), interleukin-6 (IL-6), Fms-like tyrosine kinase 3 (FLT3), or leukemia inhibitory factor (LIF). The culture media in step (c) may comprise at least one exogenous growth factor, and wherein differentiated hematopoietic stem cells are collected in step (d). The culture media in step (c) may comprise at least one of stem cell factor (SCF), interleukin-6 (IL-6), Fms-like tyrosine kinase 3 (FLT3), oncostatin-M (OSM), TGFβ3, Jagged-1, fetal bovine serum (FBS), dexamethasone, cyclic adenosine monophosphate (cAMP), Prolactin, Glucagon, niacinamide, α-lipoic acid, triiodothyronine, epidermal growth factor (EGF), high-density lipoprotein (HDL), leukemia inhibitory factor (LIF), hepatocyte growth factor (HGF), fibroblast growth factor (FGF), or human growth hormone (HGH). The culture media in step (c) may comprise at least one of stem cell factor (SCF), fibroblast growth factor (FGF), interleukin-6 (IL-6), Fms-like tyrosine kinase 3 (FLT3), or leukemia inhibitory factor (LIF). The liver organoid may be seeded with at least one of HSC obtained from cord blood, HSC obtained from bone marrow, HSC derived from induced pluripotent stem cells, HSC derived from embryonic stem cells, or HSC derived from direct reprogramming of adult somatic cells. The differentiated hematopoietic cells may comprise hematopoietic progenitor cells (HPC), myeloid progenitor cells (MPC), lymphoid progenitor cells (LPC), lymphocytes, granulocytes, macrophages, erythrocytes, or platelets. The differentiated hematopoietic cells may comprise an enriched population of differentiated erythrocytes. The culture media in step (c) may comprise erythropoietin (EPO).

The present invention is explained in greater detail in the drawings herein and the specification set forth below.

BRIEF DESCRIPTION OF THE FIGURES

The present invention may be better understood by referring to the non-limiting figures included herein:

FIGS. 2A-2G show fabrication of bio-engineered liver disc organoids in accordance with alternate aspects of the invention. FIG 2A shows liver ECM discs (8 mm diameter, 300 µm thickness) made from acellular ferret livers. Human fetal liver cells seeded on the liver ECM discs were allowed to grow in culture for 1 week. H&E staining shows formation of biliary ducts (FIG. 2B) and clusters of hepatocytes/hepatoblasts (FIG 2C). FIG. 2D shows a biliary duct with polarized epithelium showing apical staining of ASBT (inner-most circular staining around duct at panel center with some staining along left middle axis of panel) and membrane staining of EpCAM (outer-most circular staining around duct at panel center with some staining in left quadrants and bottom right quadrant of panel). FIG. 2E shows immunohistochemical staining for CYP2A (hazy stain predominately in left side quadrants with smaller patches in right side quadrants of panel). FIG. 2F shows clusters of hepatocytes/hepatoblasts expressing albumin (hazy staining throughout panel) and α-fetoprotein (AFP) (particulate staining indicated by *), a specific marker for hepatoblasts and/or very immature hepatocytes. Cell nuclei were counterstained in FIGS. 2D, 2E, and 2F (light grey circular shapes throughout panels). FIG. 2G shows the composition of the enriched hFLCPs that are seeded and cultured on the acellular ECM discs after 1 week of culturing as described in Example 1, Section A. As characterized by fluorescence activated cells sorting (FACS) analysis, the cell population seeded onto the ECM discs shows the presence of a large population of hepatic cells comprising liver progenitor cells (~55-75%) that are positive for several putative hepatoblast markers (e.g., EpCAM<ICAM1, α-fetoprotein (αFP), ALB, CK18). The cell population also contains a smaller proportion of αSMA positive or CD105 positive stromal cells (~10-25%) and CD31 positive endothelial cells (~5-15%). Histograms are representative but cell population proportions were determined based on several experiments (n=5).

FIG. 3A-3F show metabolic analysis of bioengineered liver organoid discs in accordance with alternate aspects of the invention. The bioengineered liver organoids were first incubated with phenobarbital and 3-methylcholanthrene (3-MC) in order to induce enzymatic activity and then incubated with diazepam and 7-ethoxycoumarin. After 48 hours, media samples were collected and analyzed by mass spectrometry (FIGS. 3C and 3D), and compared with standards of individual metabolites (FIGS. 3A and 3B). After enzymatic activation, the media collected from the liver organoid discs was found to contain Phase-1 metabolites Temazepam, Nordiazepam and 7-hydroxycoumarin. Robust albumin (FIG. 3E) and urea (FIG. 3F) secretion by the cells in the organoids was observed. Higher expression is observed in these contracts (triangles) than the same cell populations grown as monolayers (diamonds).

FIG. 4A shows freshly seeded hFLPCs on an acellular liver disc. FIG. 4B shows a hematoxylin and eosin (H&E) stain of an organoid having clusters of cells with hepatoblast/hepatocyte morphology. FIG. 4C shows a H&E stain of an organoid showing ductal structures resembling bile ducts. FIG. 4D shows an IHC analysis of an organoid assessed for albumin-positive hepatocytic cells (red) and CK19+ biliary cells (green). The biliary cells are found forming the doughnut-shaped ductal structures on the left side of the image and the cellular structures in the bottom right of the image (brightest aspects). The hepatocytic cells are along parts of the interior of the ductal structures, with some also being present in the cellular structures in the bottom right of the image as well. Nuclei were stained with DAPI.

FIG. 5A shows gene expression analysis of characteristic hepatic markers in the liver organoid (3D) compared to two dimensional monolayer control cultures (2D). RT-PCR was performed on organoids/cells harvested after 1 day, 7 days, and 21 days culture. GAPDH was used for normalization. FIG. 5B shows fetal liver progenitor cell distribution and lineage specification of the progenitor cells into hepatocytic and biliary phenotype after 1 week (top row) and 3 weeks (bottom row) of differentiation in the organoids. The organoids were stained for EpCAM, Albumin, and Cytokeratin 19 (left to right). The panels on the right show an overlay of the staining, including nuclei staining with DAPI.

FIG. 9A shows comparison of organoid expression after 1 week and 3 weeks culture to fetal and adult liver tissue. α-Fetoprotein (AFP) expression (green), characteristic of hepatoblasts, is abundant at week 1 in the organoid (hazy staining in central left portion of image) and in fetal liver tissue (uniform staining) but is no longer present at week 3 or in adult liver tissue. Albumin (ALB) staining is low in the fetal liver tissue (uniform) and 1 week organoid (hazy staining in left side and bottom right) but significantly increases in the adult tissue (uniform) and 3 week organoid (uniform). FIG. 9B shows expression of several adult hepatocyte markers after 3 weeks of culturing. HNF4α (left side: bright circular spots (red)); A1AT (middle: some overlapping stain along right side of image (green)), and CYP3A4 (right: some overlapping staining at bottom left and top right of image (red)). Albumin (ALB) is stained as a control (extensive staining of cellular structures; left and right images: green; middle image: red). Nuclei are stained with DAPI in FIGS. 9A and 9B.

FIG. 10A shows expression of hepatocyte differentiation markers HNFα, AST, and TAT. FIGS. 10B and 10C show expression cytochrome P450 isoforms in the liver organoids compared to adult liver tissue and hFLPCs. In FIG. 10B, the cells expressed CYP2E1, and to a lesser extent CYP3A4 and CYP2B6, after 3 weeks of culturing. FIG. 10C shows expression of hepatocyte differentiation markers CYP3A4 (at week 3) and CYP3A7 (at week 1 and week 3).

FIG. 11A shows robust albumin and urea secretion by the hepatic cells in the organoids (squares/diamonds) at day 7, 14, and 21 of culturing. Higher expression is observed in the organoids as compared to two dimensional (2D; monolayer) cultured cells (circles). FIG. 11B shows metabolic activity for the organoids after 1 week and 3 weeks of culturing. The liver organoids were first incubated with phenobarbital and 3-MC in order to induce enzymatic activity and then incubated with diazepam and 7-ethoxycoumarin. After 3, 6, 12, and 24 hours, media samples were collected and analyzed by mass spectrometry. After enzymatic activation, the media collected from the liver organoid discs was found to contain Phase-1 metabolites Temazepam, Nordiazepam and 7-hydroxycoumarin where indicated (+).

FIG. 12A shows four different stages of bile duct formations that are comparable to duct developmental stages observed in human fetal liver. Epithelial cells are stained for laminin (green) and hepatic cells are stained for CK19 (red). DAPI staining is used to identify nuclei. The ductal layer is characterized by epithelial cells forming a doughnut-shaped structure surrounded by hepatic cells in human fetal liver tissue, and laminin staining is observed along the edges of hepatic cell clusters in the organoids. The second ductal layer is characterized by the increased presence of epithelial cells, with remaining hepatic cells in close contact with each other and the epithelial cells in both fetal liver tissue and the organoids. In both fetal liver tissue and the organoids, the immature duct is characterized by significantly reduced hepatic cell presence that is generally limited to rounded clusters of cells. In the mature duct, the hepatic cells form doughnut-shaped structures surrounded by epithelial cells in both fetal liver tissue and the organoids. The top row of 12B shows that the ductal structures are positive for CK19 (green), EpCAM (red), and SOX9 (red), which are all constitutive markers of cholangiocytes, and lack albumin expression at this stage of development (top row). CK19 and EpCAM stain the doughnut-shaped ducts, while SOX9 co-stains the nuclei (DAPI) (circular spots). The bottom row of FIG. 12B shows that the ductal structures had typical bile duct apical-basal polarity, with cilia (tubulin; green) and apical sodium-dependent bile acid transporter (ASBT; blue) staining in the apical membrane and beta-catenin (red) on the baso-lateral membrane. Hepatocytic cells were stained using EpCAM (left: green) and CK19 (middle: green; right: red). YOPRO (green) and DAPI (blue) were used to stain nuclei. FIG 12C shows (RT-PCR) gene expression analysis identified increased expression of mature cholangiocyte markers HNF6, HNF1β, AE2 and GGT1 in the organoids after 1 week and 3 weeks of culturing, with comparison to adult liver tissue and isolated hFLPCs.

FIGS. 14A shows seeding of the ECM disc with EpCAM+ hepatic cells. FIG. 14B shows the presence of CK19+ hepatic cells (bright punctate and hazy staining along left two-thirds of image (red)). FIG. 14C shows the significant presence of CD45+ hematopoietic cells (red) (bright punctate and hazy staining), with such cells also surrounding a cluster of EpCAM+ hepatic cells (green) (central portion of image). FIG. 14D shows the presence of nucleated and enucleated (arrows) red blood cells (inherent hemoglobin fluorescence and IHC for HbF; bright punctate staining). FIG. 14E shows the presence of aSMA+ stromal/mesenchymal cells (red) and CD45+ hematopoietic cells (green) distributed fairly uniformly within the organoid (hazy staining). Nuclei were stained with DAPI (blue) in all images in figure.

FIG. 15A shows cell numbers in culture as determined by hemocytometer counting.

DEFINITIONS

Figure 1:
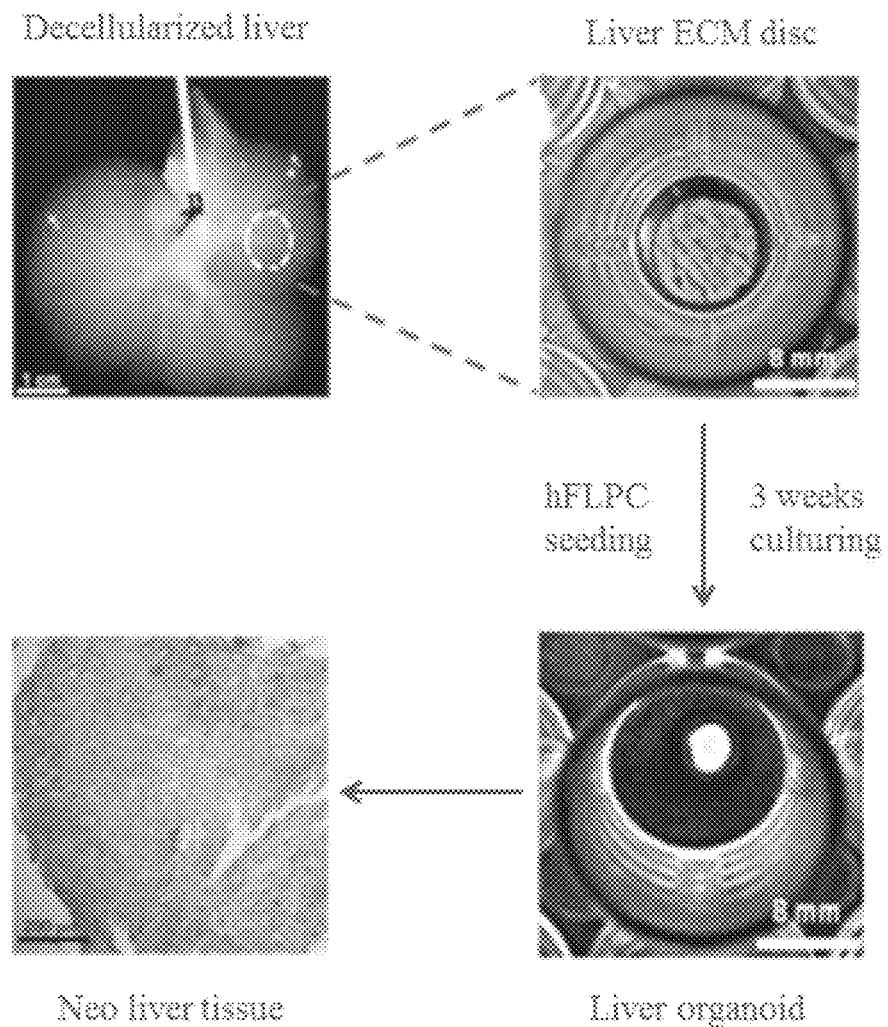
FIG. 1 shows the experimental design for generation of organoids from decellularized liver scaffold and seeding of liver progenitor cells in accordance with alternate aspects of the invention. After decellularization of a donor liver, a small portion (e.g., ECM disc) is prepared for seeding with enriched liver progenitor cells (hFLCPs). After 3 weeks of culture, a three dimensional organoid forms through recellularization of the ECM disc.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. Known methods and techniques are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with the laboratory procedures and techniques described herein are those well-known and commonly used in the art.

The following terms, unless otherwise indicated, shall be understood to have the following meanings:

As used herein, the terms "a", "an", and "the" can refer to one or more unless specifically noted otherwise.

The use of the term "or" is used to mean "and/or" unless explicitly indicated to refer to alternatives only or the alternatives are mutually exclusive, although the disclosure supports a definition that refers to only alternatives and "and/or." As used herein "another" can mean at least a second or more.

Throughout this application, the term "about" is used to indicate that a value includes the inherent variation of error for the device, the method being employed to determine the value, or the variation that exists among the study subjects.

"Bioscaffolds" or "scaffolds" or "matrices" as used herein refer to a substrate on which cells can grow. Generally, the bioscaffolds are derived from natural tissues or organs by decellularizing a natural tissue or a natural organ. These scaffolds are useful in both the medical and research settings. For example, the bioscaffolds disclosed herein may be used in hepatic tissue engineering, three-dimensional (3-D) cell culture systems and bioreactor systems. Generally, bioscaffolds are comprised of highly conserved proteins and heavily cross-linked ECM components like collagens, elastin, fibronectin, laminin and proteoglycans, which retain the characteristic 3-D architecture of the natural tissue or organ. In a some embodiment, a natural organ or a natural tissue is decellularized using a mix of detergents (e.g., Triton-X 100, SDS) and other chemicals (e.g., ammonium hydroxide, sodium deoxycholate) that allow retention of the native ECM and native vascular channels.

As used herein, the terms "decellularized" and "acellular" refer to a natural organ or a natural tissue that has been manipulated to remove all or most of the cells from the organ or tissue that are not part of the native extracellular matrix (ECM) or native vascular channels.

"Extracellular matrix" or "ECM" as used herein refers to the non-cellular component present within all natural tissues and natural organs. The ECM provides essential physical scaffolding for the cellular constituents of tissues and organs and also provides biochemical and biomechanical cues for tissue morphogenesis, differentiation and homeostasis. The ECM obtained from a natural tissue or a natural organ that is generally chemically and physically unchanged following decellularization of the natural tissue or the natural organ is referred to herein as the "native ECM".

As used herein, the terms "micro-environment niche" or "niche" are used to refer to a region in organ (e.g., fetal liver) that supports certain cellular functions of the organ. These niches are made up of one or more cell populations within the organ that produce chemical signals that influence cell function or behavior. For example, in the fetal liver, there are niches that support of HSC expansion (proliferation) or differentiation. The characteristics of a niche that supports HSC expansion are in part different from the characteristics of a niche that supports HSC differentiation. The cells in different niches communicate with one another through contact and/or release of paracrine factors to regulate the rate of HSC expansion and differentiation.

"Natural organs" and "natural tissues" are organs and tissues that are freshly retrieved from animals and humans without manipulation. Organs and tissues that may be used to carry out the present invention may be from any suitable animal source, including human, other mammalian (e.g., cat, dog, pig, cow, sheep, horse, monkey), avian (e.g., chicken, turkey, duck, goose, etc.), reptile, amphibian, etc. In some embodiments of the invention, the natural organ is a liver and the natural tissue is a portion of a liver.

As used herein, the terms "organoid" or "organoid disc" or "disc" or "bioengineered organoid" are used to refer to an organ-like structure or a tissue-like structure that mimics some or all of the properties of a natural organ or natural tissue in vivo. An organoid resembles a natural organ in structural appearance or qualities. The organoid can resemble either an adult organ or a fetal organ in structural appearance or qualities. In the context of the invention, the organoid retains the extracellular matrix and native vascular channels of the natural organ or natural tissue. Organoids are derived in part from a natural organ or portion of natural tissue obtained from a donor subject. Where the organoid is a portion of tissue, the portion of tissue can range in size from at least 200,000 cells to nearly the full size of the natural organ. An organoid can be derived from a full-size natural organ or portion of natural tissue. The term organoid also refers to small excised portions of a larger organoid (e.g., an excised disc).

As used herein, the terms "subject", "individual" and "patient" are used interchangeably to refer to an animal, preferably a human, but also includes other mammals (e.g., cat, dog, pig, cow, sheep, horse, monkey), birds (e.g., chicken, turkey, duck, goose, etc.), reptiles, amphibians, etc.

"Native vascular channels" as used herein refers to the circulatory system components present in natural organs and natural tissues, which include vessels and capillaries. The vascular channels are distributed throughout natural organs and natural tissues and acts to provide nutrients and oxygen to the surrounding cells. The vascular channels, not including the vascular cells, obtained from a tissue or organ that is generally unchanged following decellularization of the tissue or organ is referred to herein as native vascular channels.

DETAILED DESCRIPTION

Disclosed herein are liver organoids, methods of making such organoids, and methods of using such organoids.

A. Bioengineered Liver Organoids

While previous studies provided critical "proof-of-concept" that a scaffold comprised of a decellularized liver ECM can be used to fabricate fully functional, human liver tissue, a repopulated whole liver does not lend itself to multi-parameter optimization of the culture conditions to support/expand human HSC.

Thus, in accordance with embodiments of the invention, in vitro three-dimensional (3-D), liver extracellular matrix (ECM)-derived scaffolds have been developed. When human fetal hepatoblasts and endothelial cells are seeded into these scaffolds, they are engrafted in their putative native locations within the liver ECM scaffolds, and subsequently display typical endothelial, hepatic, and biliary epithelial markers, thus creating a hepatic-like tissue in vitro.

In embodiments of the invention, a decellularized donor liver tissue is used as the bioscaffold for a liver organoid. The bioscaffold has the native ECM and native vascular channels of the donor liver tissue. Liver cells are then seeded onto the bioscaffold and cultured with culture media. The liver cells may be hepatoblasts, stromal cells, cholangiocytes, endothelial cells, or any combination thereof.

In some embodiments, the invention is a liver organoid comprising a bioscaffold derived from a decellularized donor subject liver comprising a native extracellular matrix (ECM) and native vascular channels; and liver cells having predominately fetal characteristics. For example, the liver cells may be immature or fetal-like in nature. In some embodiments, the liver cells may comprise at least one of liver progenitor cells, hepatoblasts, vascular cells, cholangiocytes, or stromal cells. In certain embodiments, the vascular cells may comprise at least one of liver endothelial cells, liver sinusodial cells, vascular smooth muscle cells, or pericytes. In some embodiments, the hepatoblasts may comprise at least one of fetal liver hepatoblasts, hepatoblasts derived from adult-derived liver stem cells, hepatoblasts derived from induced pluripotent stem cells, or hepatoblasts derived from embryonic stem cells. In certain embodiments, the liver cells may comprise an enriched fetal liver progenitor cell population comprising at least about 55-75% hepatic cells and not more than about 15-25% stromal cells and not more than about 5-15% endothelial cells. In some embodiments, the liver cells may comprise an enriched fetal liver progenitor cell population comprising about 55-75% hepatic cells, about 15-25% stromal cells, about 5-15% endothelial cells. In some embodiments, the liver cells may express at least one of α-fetoprotein or CYP3A7. In certain embodiments, the hepatic cells may comprise fetal liver progenitor cells.

Another embodiment of the invention is a liver organoid comprising a bioscaffold derived from a decellularized donor subject liver comprising a native extracellular matrix (ECM) and native vascular channels; and liver cells having adult characteristics. For example, the liver cells may have mature or adult-like gene expression patterns or capabilities. In some embodiments, the liver organoid has liver cells that have fetal characteristics and adult characteristics, reflecting maturation of the cells of the organoid. In some embodiments, the liver cells comprise at least one of hepatoblasts, hepatocytes, vascular cells, cholangiocytes, or stromal cells. In certain embodiments, the vascular cells may comprise at least one of liver endothelial cells, liver sinusodial cells, vascular smooth muscle cells, or pericytes. In some embodiments, the hepatocytes may be derived from at least one of fetal liver hepatoblasts, hepatoblasts derived from adult-derived liver stem cells, hepatoblasts derived from induced pluripotent stem cells, or hepatoblasts derived from embryonic stem cells. In certain embodiments, the liver organoid may comprise hepatocytic cell clusters and biliary ducts. In certain embodiments, the liver cells may express albumin. In some embodiments, the liver cells may express at least one cytochrome P450 isoform. In some embodiments, the liver cells may express at least one of CK7, CK19, transferrin, CYP3A4, HNF4 α, AST, ALT, TAT, CYP2E1 or A1AT. In certain embodiments, the liver cells may synthesize urea. In some embodiments, the liver cells can metabolize certain drug compounds metabolized by the adult liver in vivo.

In another embodiment, the invention is a method of generating a liver organoid comprising the steps of providing a bioscaffold derived from a decellularized donor subject liver comprising a native extracellular matrix (ECM) and native vascular channels, seeding the bioscaffold with liver cells; and culturing the liver cells with culture medium containing at least one growth factor to generate a liver organoid comprising differentiated liver cells over time. In some embodiments, the liver cells may comprise at least one of hepatoblasts, hepatocytes, vascular cells, cholangiocytes, or stromal cells. In certain embodiments, the vascular cells may comprise at least one of liver endothelial cells, liver sinusodial cells, vascular smooth muscle cells, or pericytes. In some embodiments, the hepatoblasts may comprise at least one of fetal liver hepatoblasts, hepatoblasts derived from adult-derived liver stem cells, hepatoblasts derived from induced pluripotent stem cells, or hepatoblasts derived from embryonic stem cells. In certain embodiments, the liver cells of step (b) may comprise an enriched fetal liver progenitor cell population comprising at least about 55-75% hepatic cells and not more than about 15-25% stromal cells and not more than about 5-15% endothelial cells. In certain embodiments, the liver cells of step (b) may comprise an enriched fetal liver progenitor cell population comprising about 55-75% hepatic cells, about 15-25% stromal cells, about 5-15% endothelial cells. In some embodiments, the hepatic cells may comprise fetal liver progenitor cells. In some embodiments, the liver organoid may comprise hepatocytic cell clusters and biliary ducts. In some embodiments, the differentiated liver cells of step (c) may express albumin. In certain embodiments, the differentiated liver cells of step (c) may express at least one cytochrome P450 isoform. In some embodiments, the culture medium of step (c) may comprise oncostatin M. In certain embodiments, the culture medium of step (c) may comprise at least one of dexamethasone, cyclic adenosine monophosphate (cAMP), Prolactin, Glucagon, niacinamide, α-lipoic acid, triiodothyronine, free fatty acids, epidermal growth factor (EGF), high-density lipoprotein (HDL), hepatocyte growth factor (HGF), fibroblast growth factor (FGF), or human growth hormone (HGH).

In some embodiments of the invention, liver cells used to generate the organoids are from natural sources (e.g., fetus tissue). In some embodiments, the liver cells from natural sources are enriched prior to culturing in the liver organoids. Fetal liver cells can be identified by the expression of specific cell surface markers such as, e.g., EpCAM, ICAM1, α-fetoprotein, albumin (ALB), and CD18. In some embodiments of the invention, liver cells may be enriched by active selection of the fetal hepatic cell population using a cell surface marker characteristic of these cells. Similarly, other cell populations present in the fetal liver may also be isolated, including stromal cells (identified by, e.g., markers such as αSMA or CD105) and endothelial cells (identified by, e.g., markers such as CD31).

In some embodiments of the invention, the source of liver cells used to generate the organoids are is embryonic stem cells (ES cells). ES cells are pluripotent stem cells derived from the inner cell mass of a blastocyst, an early-stage embryo. ES cells can be induced to become liver cells (mature or immature) for use in embodiments of the invention.

In other embodiments of the invention, the source of liver cells used to generate the organoids are is induced pluripotent stem cells (iPS cells or iPSC). iPS cells are a type of pluripotent stem cell artificially derived from a non-pluripotent cell—typically an adult somatic cell—by inducing expression of specific genes (e.g., at least Oct-3/4 (Pou5f1), Sox2). iPS cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. iPS cells can be generated from a variety of adult somatic cells, including, e.g., stomach cells, liver cells, skin cells and blood cells. iPS cells can be induced to become liver cells (mature or immature) for use in embodiments of the invention.

In some embodiments of the invention, liver cells used to generate the organoids are directly reprogrammed adult somatic cells. Direct reprogramming, or transdifferentiation, is the direct conversion of one cell type to another without undergoing an intermediate pluripotent state or progenitor cell type. Reprogramming of cells to a different cell type is usually done by either somatic cell nuclear transfer (SCNT) or through expression of transcription factors or microRNA precursors. Direct reprogramming can be performed using a variety of cells types, including, e.g., skin, muscle, blood, pancreatic, and neurons. Studies have shown that adult somatic cells (e.g., fibroblasts) can be directly reprogrammed into multipotent blood progenitor cells [65].

In some embodiments, the liver organoids are useful for studying liver development in vitro. Reconstitution of differentiation of fetal liver cells on bioscaffolds enables in vitro monitoring of different developmental stages with respect to morphology, molecular characteristics, and functionality. In various embodiments, the liver organoids present a small scale, simple system for early stage assessment of drugs without requiring use of animal studies. In other embodiments, the liver organoids are useful for in vitro assessment of pharmacokinetics and pharmacology drug metabolism and liver function. In addition, in some embodiments, the liver organoids are useful for in vitro toxicity studies. For example, in some embodiments, teratogenesis studies can be conducted using the liver organoids to assess the impact of compounds on morphogenesis during development/embryogenesis. In certain embodiments, the types of studies described above are performed using liver organoids comprising liver cells having adult characteristics. In other embodiments, the studies may be performed using liver organoids comprising liver cells having predominately fetal characteristics. In other embodiments, the studies may be initiated on liver organoids comprising liver cells having predominately fetal characteristics and performed overtime to monitor the impact of the compounds assessed on maturation of the liver organoid to one comprising liver cells having adult characteristics. In certain embodiments, the types of studies described above are performed by introducing compounds to be assessed into the culture medium in which the liver organoids are being cultured.

In some embodiments of the invention, liver organoids are produced as liver organoid discs. As shown in and Fig. 2A, liver ECM discs may be made from acellular animal livers. Human fetal liver cells (enriched fetal liver progenitor cells) may be seeded on the liver ECM discs and allowed to grow in culture (e.g., 1 week). In some embodiments, H&E staining identifies formation of biliary ducts (FIG. 2B) and clusters of hepatocytes/hepatoblasts (FIG. 2C) after 3 weeks of culturing. In some embodiments, apical staining and membrane staining (FIG. 2D), as well as IHC staining for CYP2A (FIG. 2E) of biliary ducts with polarized epithelial can be performed after 3 weeks of culturing. In some embodiments, hepatocytes/hepatoblasts in the liver organoid can be assessed by staining for expression of albumin and AFP (FIG. 2F).

Liver organoids are generated from acellular ECM discs seeded with human fetal liver cells (enriched fetal liver progenitor cells) (FIG. 2A). Biliary structure may be observed by H&E staining (FIG. 2B) and also identified by HSC staining for bile ducts (ABST+) amongst hepatic cells (EpCAM+) (FIG. 2D). Hepatic structures may also be observed by H&E staining (FIG. 2C) and identified by HSC staining for hepatic cell markers CYP2A (Panel E) and albumin and α-fetoprotein (FIG. 2F).

Figure 4A:
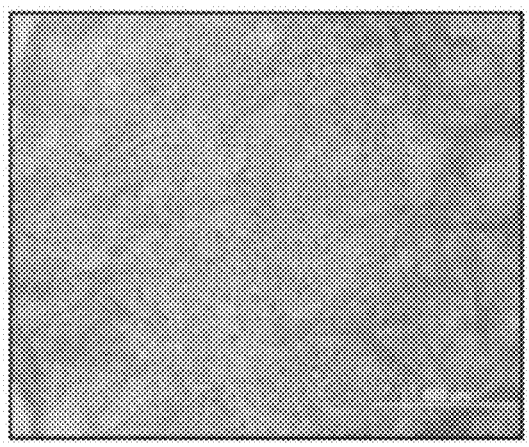
FIGS. 4A-4D show the self-assembly of the enriched hFLPC population seeded onto the ECM discs into a three dimensional organoid structure within 7-10 days of culturing.
Figure 4B:
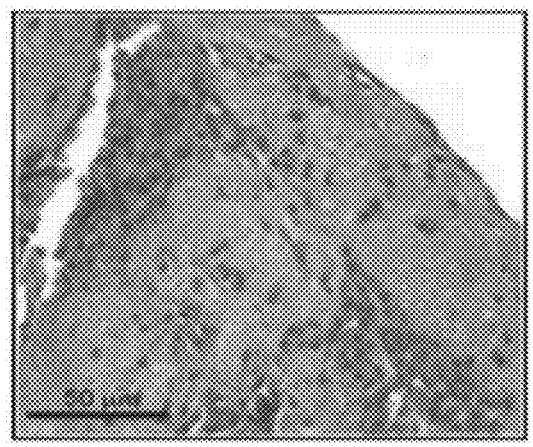
Figure 4C:
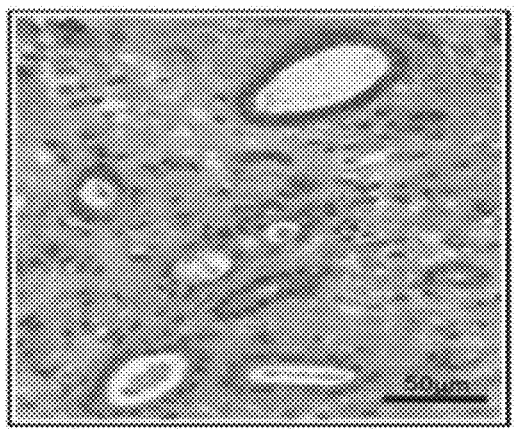
Figure 4D:
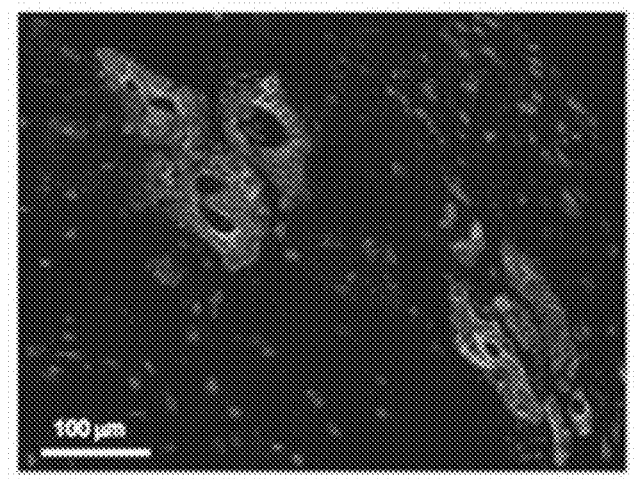

In addition, in some embodiments, assembly of fetal liver cells on the ECM discs into liver organoids occurs after 5-7 days of culturing. The organoids have large expanses of liver cells (FIG. 4A) that show hepatic morphology (FIG. 4B) and also the formation of biliary duct structures (FIG. 4C) as demonstrated by H&E staining. The presence of hepatic and biliary cells present in the organoids can be confirmed by IHC staining for albumin and CK19, respectively.

In some embodiments, the fetal liver cells seeded on the ECM discs are an enriched population of fetal liver progenitor cells (hFLPCs) isolated from fetal liver tissue. As shown in FIG. 2G, FACS analysis identifies the different subpopulations of cells present in the enriched hFLPCs, including hepatic cells (as shown by markers EpCAM, ICAM1, α-fetoprotein, albumin, and CK18), stromal cells (as shown by markers α-SMA and CD105), and endothelial cells (as shown by marker CD31). In some embodiments, the enriched hFLPCs contain about 55-75% hepatic cells (primarily liver progenitor cells), about 15-25% stromal cells, and about 5-15% endothelial cells. In some embodiments, depending on the culture conditions used to generate the enriched hFLPCs, the enriched hFLPCs contain at least about 55-75% hepatic cells (primarily liver progenitor cells), not more than about 15-25% stromal cells, and not more than about 5-15% endothelial cells.

Figure 11A:
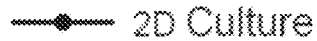
FIGS. 11A and FIG. 11B show synthetic and metabolic analyses of liver organoids in accordance with alternate aspects of the invention.
Figure 11B:
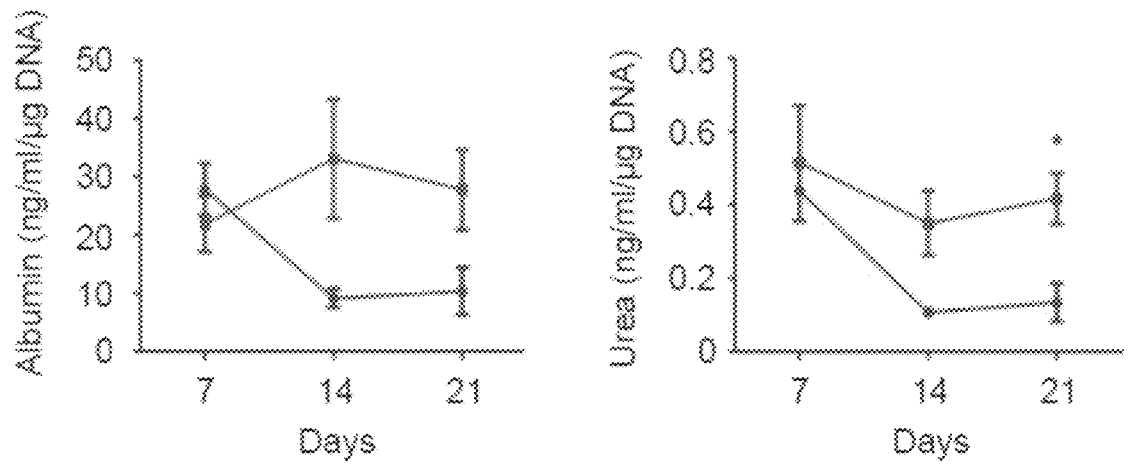

In some embodiments, the liver organoids can be used to assess liver function. For example, in some embodiments of the invention, metabolic activity of liver organoid discs can be assessed as shown in FIG. 3A-3F. The liver organoid discs can be first incubated with phenobarbital and 3-MC in order to induce enzymatic activity and then incubated with Diazepam and 7-ethoxycoumarin. After 48 hrs, media samples can be collected and analyzed by mass spectrometry (FIGS. 3C and 3D), and compared with standards of individual metabolites (FIGS. 3A and 3B). The media collected from the liver organoid discs can be assessed for Phase-1 metabolites (e.g., Temazepam, Nordiazepam and 7-hydroxycoumarin). A similar analysis is shown in FIG. 11B. In addition, in some embodiments, the liver organoids can be used to assess liver function. For example, albumin and urea secretion by the hepatic cells in the organoids can be assessed as shown in FIG. 3E and FIG. 3F, respectively. A similar analysis is shown in FIG. 11A.

Figure 5A:
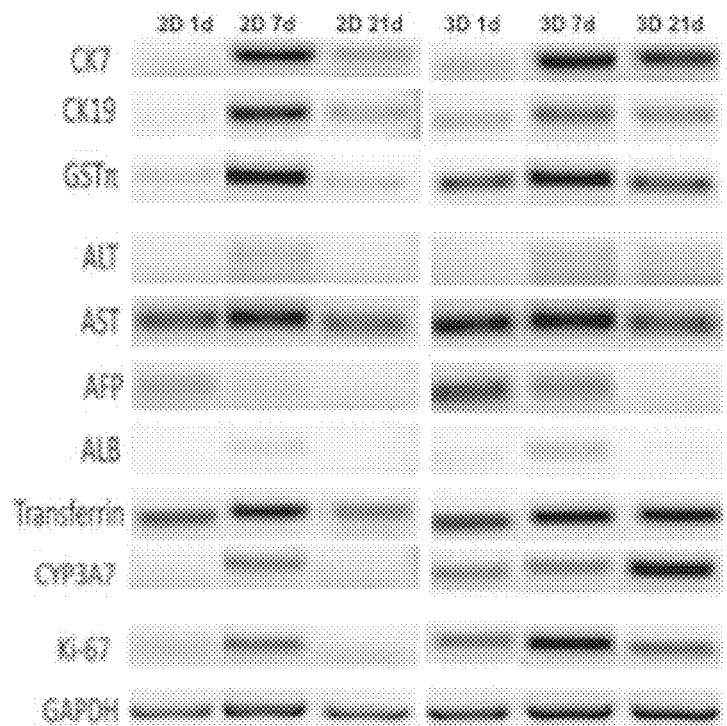
FIG. 5A and FIG. 5B show liver organoid characteristics in accordance with alternate aspect of the invention.

In some embodiments of the invention, the liver organoids display characteristic expression of many liver cell markers. For example, as shown in FIG. 5A, RT-PCR analysis identifies increased expression of many liver proteins over time. In some embodiments, this expression greater than that observed for 2D monolayer cell cultures. In addition, in some embodiments, the liver organoids contain differentiated cell populations and more mature, adult-like morphology. For example, as shown by IHC in FIG. 5B, after 3 weeks of culturing, the liver organoids contain hepatic cell clusters (ALB+/CK19−) and biliary ductal structure (ALB−/CK19+) as can be shown by IHC analysis. In certain embodiments, EpCAM expression decreases over time and expression moves from the cytoplasm at 1 week of culturing to the cell membrane after 3 weeks of culturing.

Figure 6:
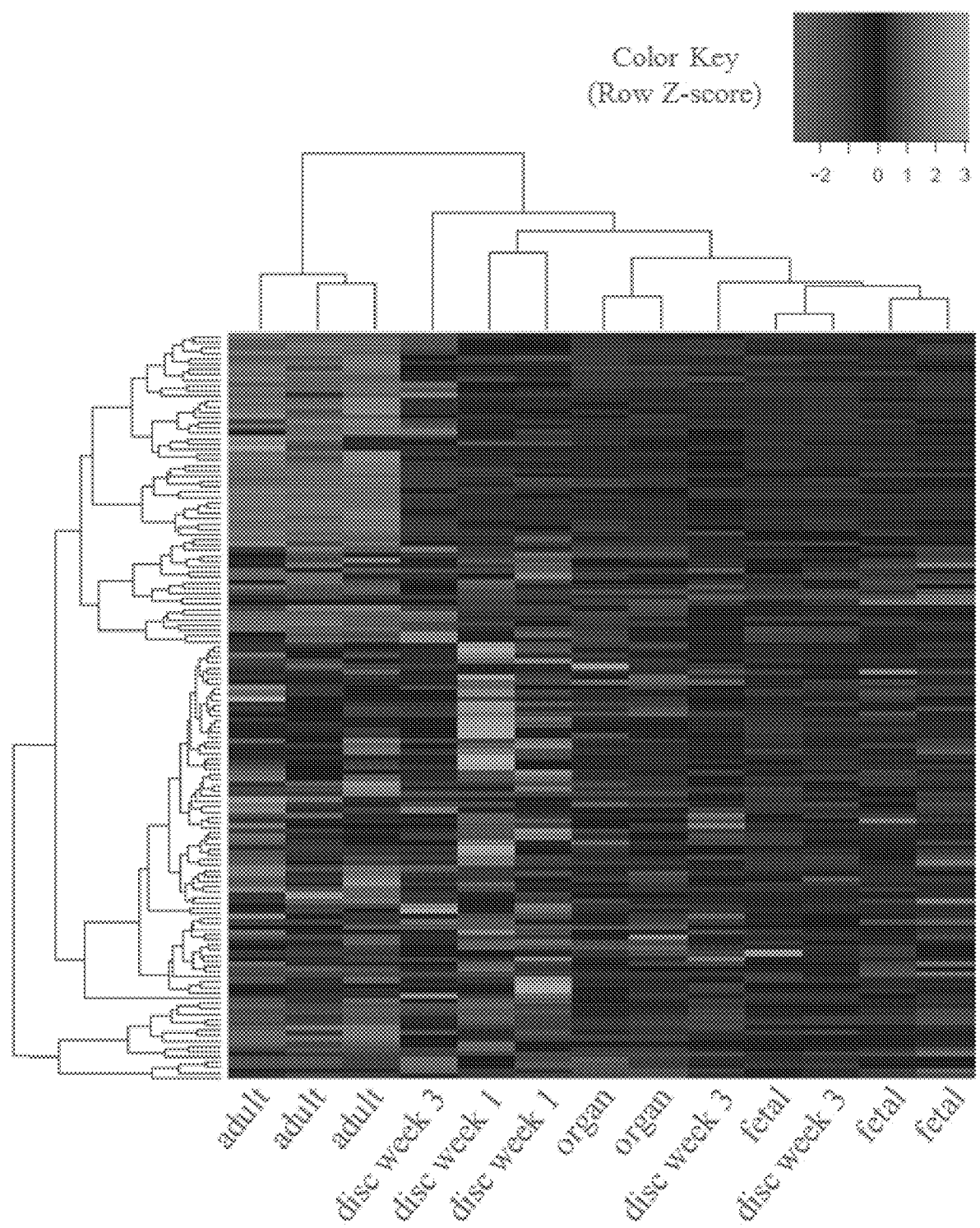
FIG. 6 shows cDNA microarray analysis heat map of a large range of putative liver genes in accordance with alternate aspects of the invention. Gene expression patterns in the organoids after 1 week and 3 weeks of culturing were compared to expression patterns in adult tissue, fetal tissue, and recellularized liver. The intensity/color of each gene reflects extent of expression (Z score) in comparison to fetal liver tissue controls: red/medium grey (low), black (medium), green/light grey (high).
Figure 7:
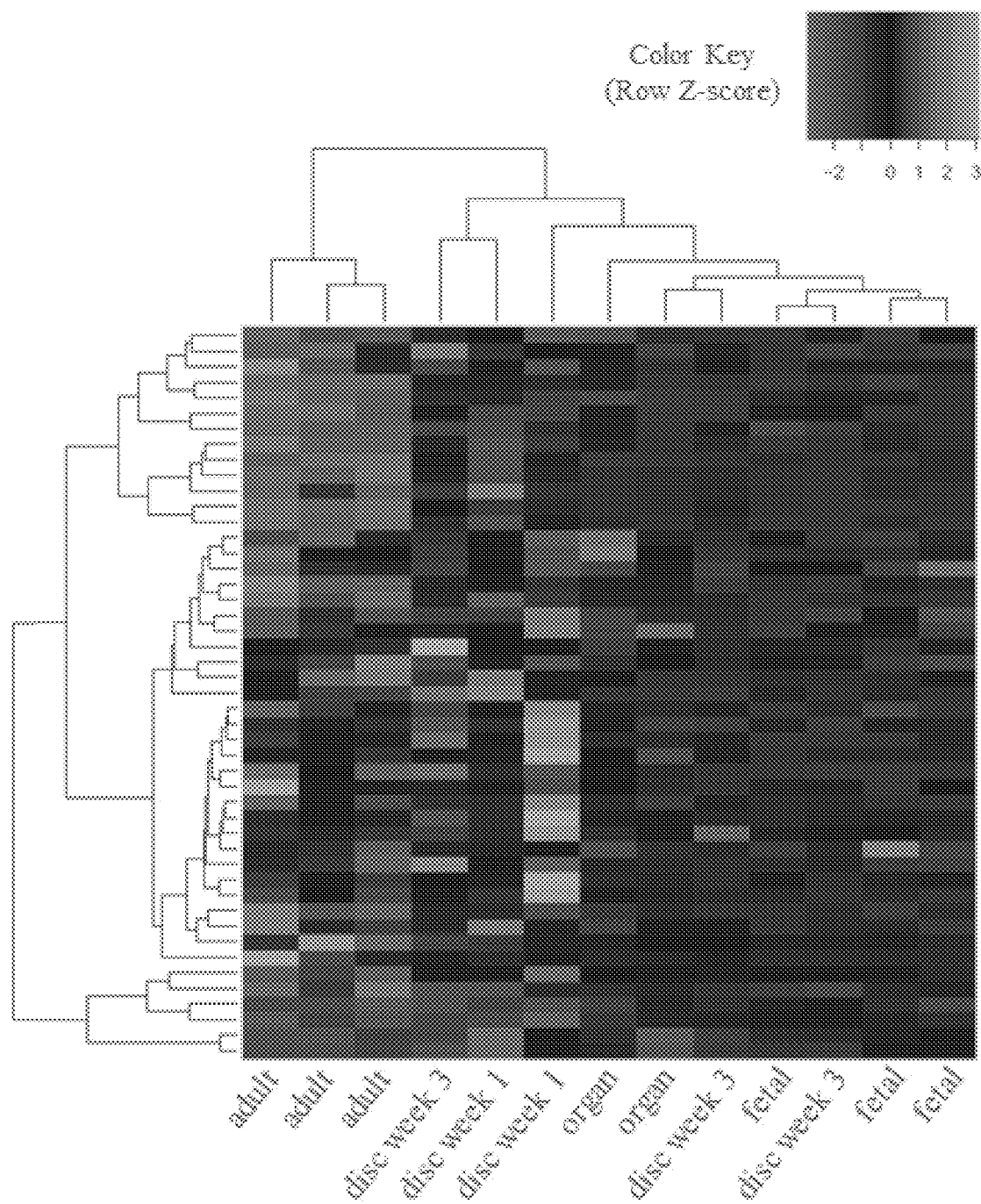
FIG. 7 shows cDNA microarray analysis heat map of genes associated with reactome bile acid and bile salt metabolism in accordance with alternate aspects of the invention. Gene expression patterns in the organoids after 1 week and 3 weeks of culturing were compared to expression patterns in adult tissue, fetal tissue, and recellularized liver. The intensity/color of each gene reflects extent of expression (Z score) in comparison to fetal liver tissue controls: red/medium grey (low), black (medium), green/light grey (high).
Figure 8:
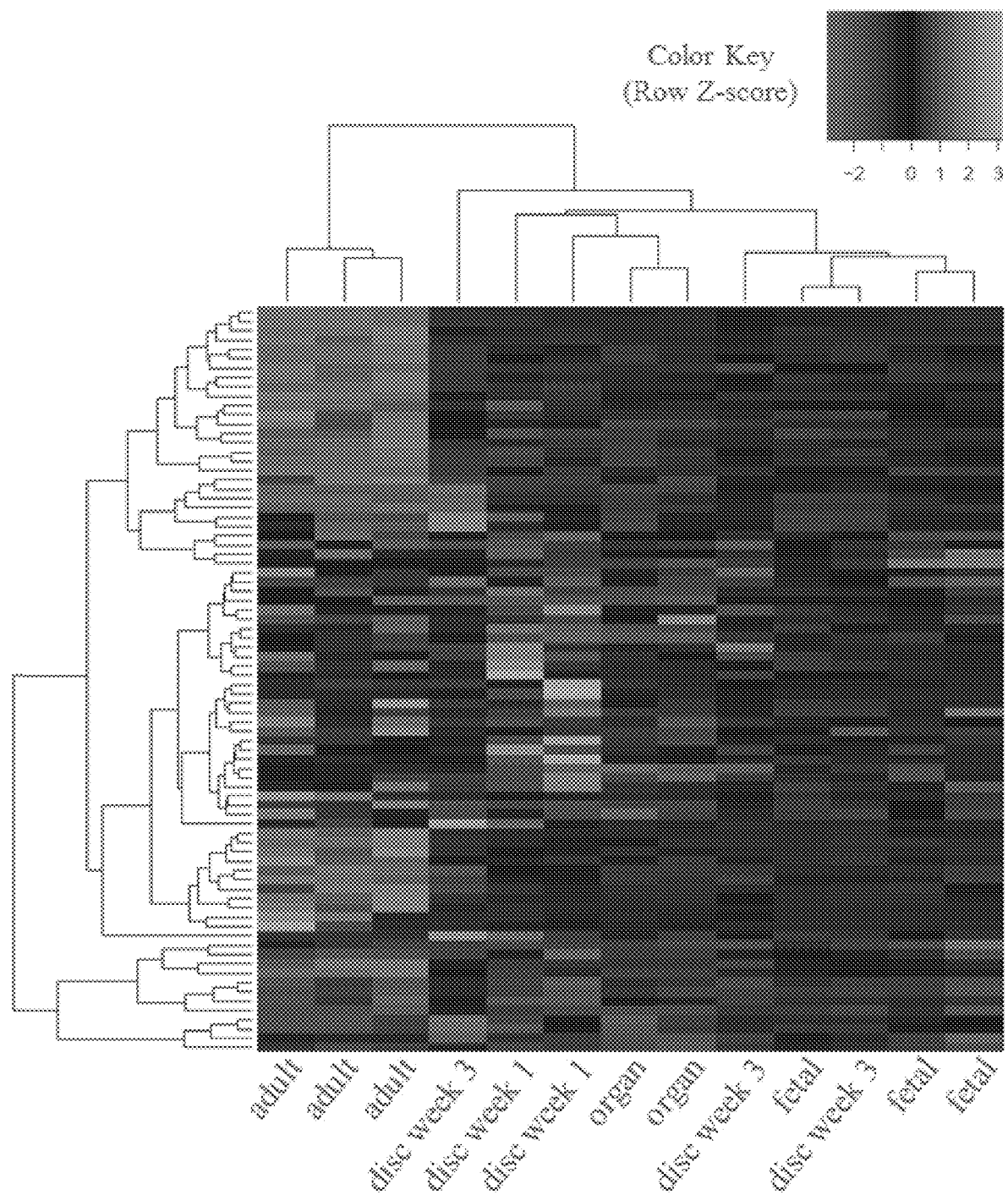
FIG. 8 shows cDNA microarray analysis heat map of hepatic genes in accordance with alternate aspects of the invention. Gene expression patterns in the organoids after 1 week and 3 weeks of culturing were compared to expression patterns in adult tissue, fetal tissue, and recellularized liver. The intensity/color of each gene reflects extent of expression (Z-score) in comparison to fetal liver tissue controls: red/medium grey (low), black (medium), green/light grey (high).

In embodiments of the invention, the organoid discs mature during culturing, showing progressive differentiation. For example, microarray analysis shows a gene expression pattern for putative liver genes more similar to adult than fetal human liver at 3 weeks (as shown in FIG. 6), as well as biliary and hepatic genes (as shown in FIG. 7 and FIG. 8, respectively).

Figure 9A:
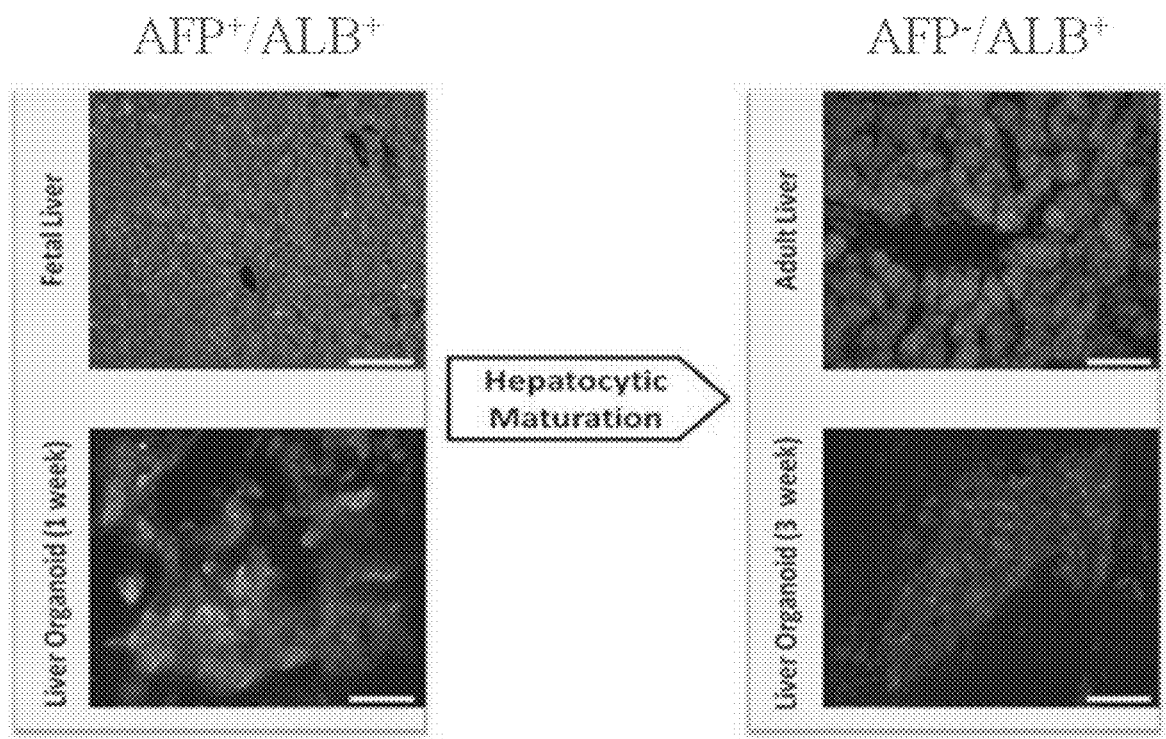
FIGS. 9A and FIG. 9B show the maturation of the liver organoids in accordance with alternate aspects of the invention.
Figure 9B:
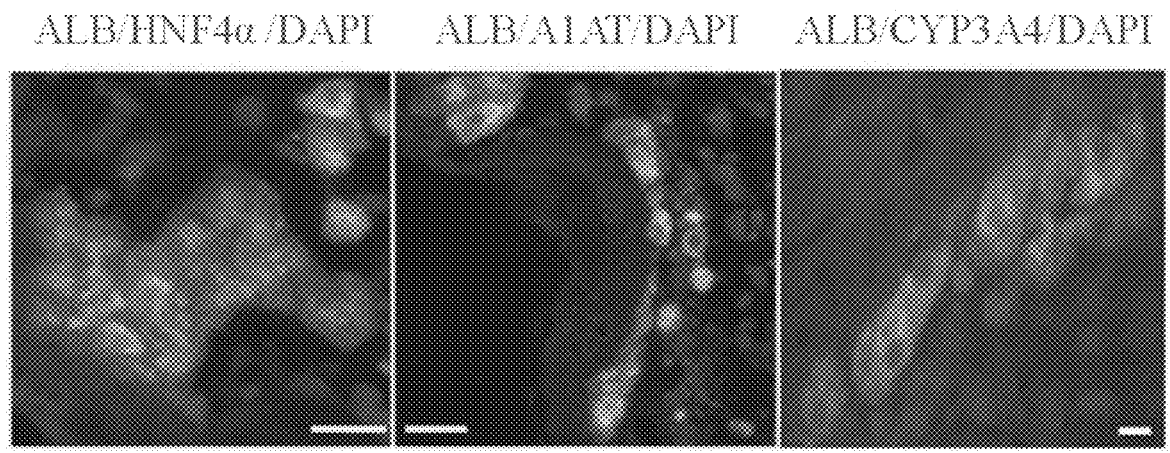

In some embodiments, the liver organoids show developmental maturation over time while in culture. As shown in FIG. 9A, after 1 week of culture the liver organoids bear morphological and protein expression characteristics similar to fetal liver tissue, while after 3 weeks of culture, the bear morphological and protein expression characteristics similar to adult tissue as can be determined by IHC analysis. For example, in some embodiments, the liver organoids after 1 week of culture express α-fetoprotein (AFP) and low levels of albumin (ALB), while after and 3 weeks of culture do not express AFP but does express ALB fetal liver tissue, as do fetal and adult liver tissue, respectively. In some embodiments, as shown in FIG. 9B, the liver organoids have hepatic cell clusters characteristic of mature liver tissue. In addition, in some embodiments, the hepatic clusters show expression of adult hepatocyte markers HNF4α, alpha-1-antitrypsin (A1AT), and cytochrome P450 3A4 after three weeks of culture as can be shown by IHC analysis.

Figure 10A:
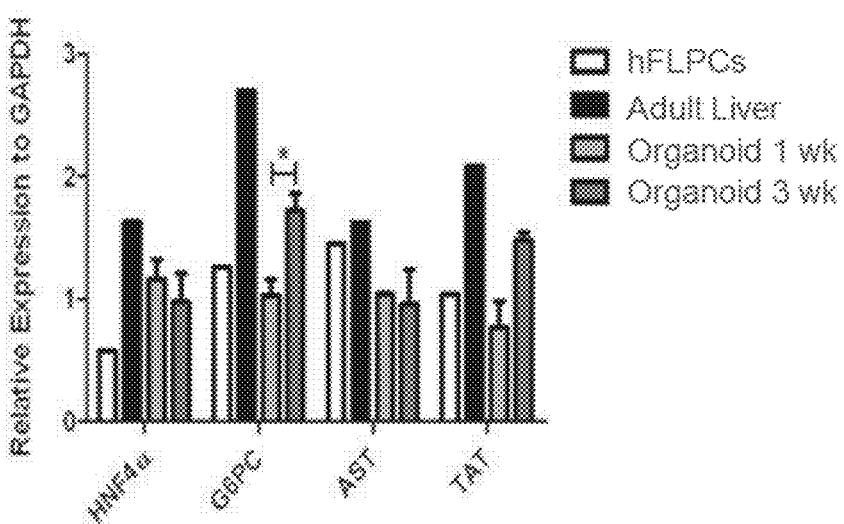
FIGS. 10A-10C show gene expression analysis (RT-PCR) of the liver organoids compared to adult liver tissue and hFLPCs in accordance with alternative aspects of the invention.
Figure 10B:
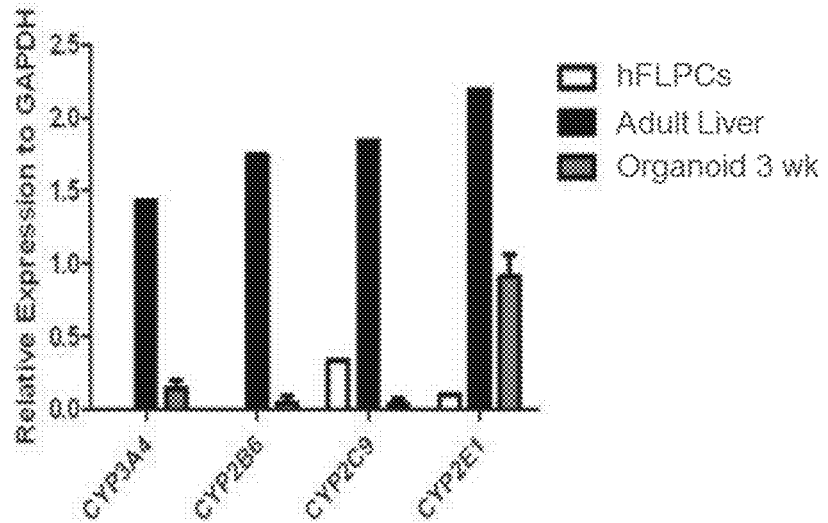
Figure 10C:
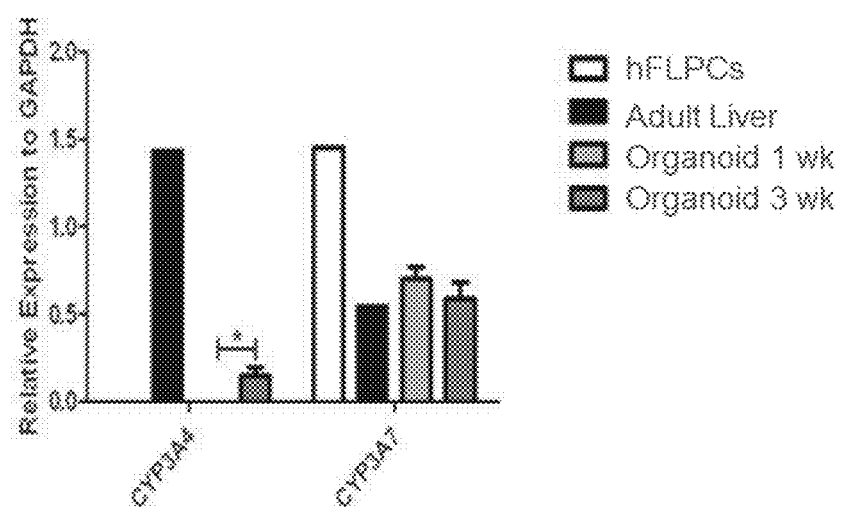

In some embodiments, the liver organoids can be used to assess development of the liver. For example, as shown in FIG. 10A, the liver organoids express HNF4α and AST after 3 weeks of culture. In addition, the liver organoids showed high expression of different cytochrome P450 isoforms (mature liver enzymes) whether the organoids were induced with the drugs phenobarbital and 3-methylcholanthrene (FIG. 10B) or not (FIG. 10C).

Figure 12A:
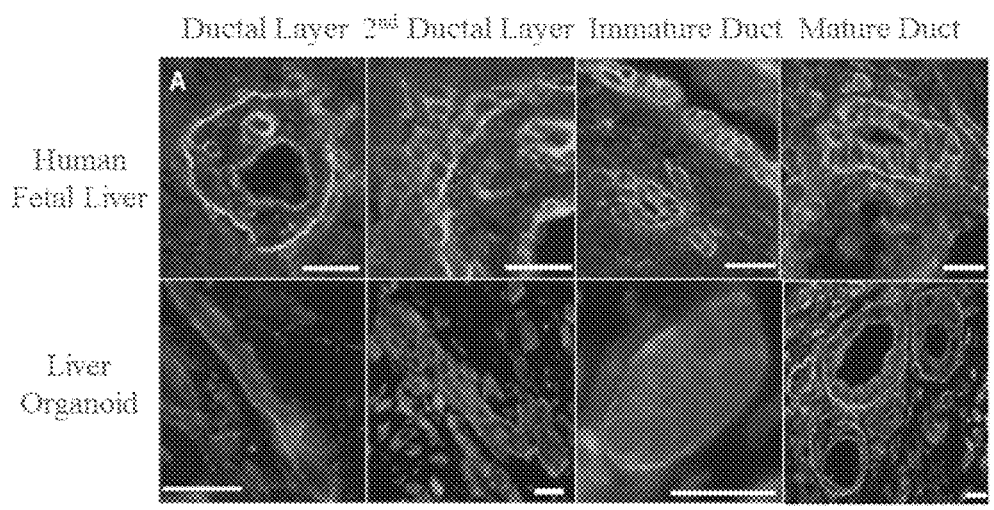
FIG. 12A and FIG 12C show bile duct/epithelial cells differentiation of cells in the liver organoid in accordance with alternate aspects of the invention.
Figure 12B:
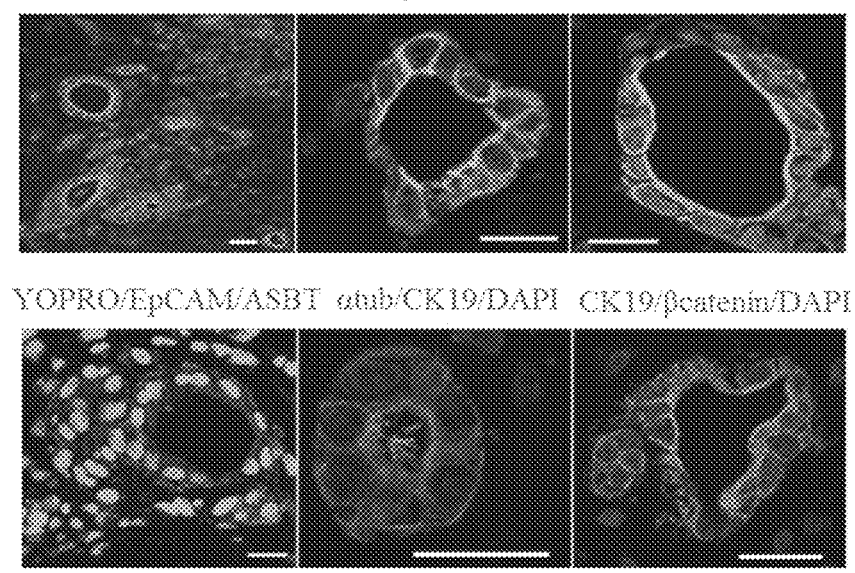

For example, in some embodiments, the liver organoids are useful for assessing morphogenesis of liver structures during development. As shown in FIG. 12A by IHC analysis, the liver organoids show four different stages of bile duct formation (ductal layer, second ductal layer, immature duct, mature duct). In some embodiments, the liver organoids contain CK19+/EpCAM+/SOX9+ biliary duct cells identical to that observed during the fetal duct morphogenesis process including laminin in the basal membrane surrounding the CK19+ biliary duct cells (cholangiocytes) as shown in FIG. 12B (top row). In some embodiments, the liver organoids contain biliary structures exhibiting typical bile duct apical-basal polarity, indicated by the presence of primary cilia (antitubulin) and a bile salt transporter (ABST) in the apical membrane and beta-catenin on the baso-lateral membrane FIG. 12B (bottom row). In some embodiments, as shown by RT-PCR analysis in FIG. 12C, the liver organoids express of HNF6 (a critical transcription factor in bile duct morphogenesis), HNF1β (a transcription factor important for lineage specification of hepatoblasts into cholangiocytes), anion exchange factor 2 (AE2); and GGT1, all markers of mature cholangiocytes.

B. Fetal Liver Organoids for Hematopoietic Cell Culturing

A liver organoid can be created to mimic the function of the human fetal liver such that HSC can be cultured in vitro using the liver organoid to support the expansion and/or differentiation of HSC. The disclosed invention allows for the in vitro expansion of long-term repopulating HSC in such a way that sufficient numbers of HSC can be obtained to engraft an adult, while simultaneously increasing committed progenitor populations that are able to shorten time to engraftment (i.e., speed hematopoietic recovery after transplant). As such, in embodiments of the invention, the described liver organoids, and methods of using them, support asymmetric division and symmetric renewal of HSC (and HPC).

In embodiments of the invention, liver organoids are disclosed herein are able to (1) support HSC expansion on a large scale without sacrificing their self-renewal ability, (2) produce expanded HSC that are safe, transplantable, and free of feeder cells, serum proteins, and microbial agents, and (3) also support differentiation of HSC to allow large scale production of differentiated hematopoietic cells. The availability of these liver organoids allows use of readily available sources of HSC that otherwise have limited utility (e.g., cord blood HSC) to use for transplantation to treat a range of illnesses. In addition, these liver organoids permit the production of large pools of HSC having defined characteristics (e.g., blood type, HLA class) as well as specific HSC pools (e.g., patient-specific, ethnicity matched). Also, the liver organoids also enable production of a wide range of differentiated hematopoietic cells.

One embodiment of the invention is a liver organoid comprising: (a) a bioscaffold derived from a decellularized donor subject liver comprising a native extracellular matrix (ECM) and native vascular channels; and (b) liver cells comprising at least one micro-environment niche that supports hematopoietic stem cell (HSC) expansion or differentiation. In embodiments of the invention, the liver organoids may comprise one or more types of liver cells. In some embodiments of the invention, the liver cells comprise at least two micro-environment niches, wherein in at least one micro-environment niche supports HSC expansion and at least one micro-environment niche supports HSC differentiation. In some embodiments of the invention, the liver cells of the liver organoid may comprise fetal liver cells. In some embodiments of the invention, the liver cells of the liver organoid may comprise at least one of liver progenitor cells, hepatoblasts, vascular cells, cholangiocytes, or stromal cells. In some embodiments of the invention, where the liver cells of the liver organoid are vascular cells, the vascular cells may comprise at least one of liver endothelial cells, liver sinusodial cells, vascular smooth muscle cells, or pericytes. In some embodiments of the invention where the liver cells of the liver organoid are stromal cells, the stromal cells may comprise mesenchymal cells. In some embodiments of the invention where hepatoblasts are liver cells of the liver organoid, the hepatoblasts may comprise at least one of fetal liver hepatocytes, hepatoblasts derived from adult-derived liver stem cells, hepatoblasts derived from induced pluripotent stem cells, or hepatoblasts derived from embryonic stem cells.

In some embodiments of the invention, the at least one micro-environment niche supports expansion and/or differentiation of HSC from a variety of sources. In some embodiments of the invention, the at least one micro-environment niche supports expansion or differentiation of at least one of HSC obtained from cord blood, HSC obtained from bone marrow, HSC derived from induced pluripotent stem cells, HSC derived from embryonic stem cells, or HSC derived from direct reprogramming of adult somatic cells. In certain embodiments, the at least one micro-environment niche supports expansion or differentiation of HSC obtained from cord blood.

In some embodiments of the invention, the liver organoids provide a system to study the different micro-environment niches of the fetal liver that support asymmetric division and symmetric renewal of HSC.

Another embodiment of the invention is a method of generating a liver organoid comprising the steps of: (a) providing a bioscaffold derived from a decellularized donor subject liver comprising a native extracellular matrix (ECM) and native vascular channels; (b) seeding the bioscaffold with liver cells; and (c) culturing the liver cells with the bioscaffold in the presence of culture media for sufficient time to produce at least one micro-environment niche in the bioscaffold that supports hematopoietic stem cell (HSC)

expansion or differentiation. In certain embodiments of the invention, the method generates liver organoids as described in the above embodiments. In some embodiments of the invention, the liver cells are cultured with the bioscaffold in the presence of culture media for sufficient time to produce at least two micro-environment niches in the bioscaffold, wherein at least one micro-environment niche supports HSC expansion and at least one micro-environment niche supports HSC differentiation. In some embodiments, the liver cells of step (a) may comprise fetal liver cells. In some embodiments, the liver cells of step (a) may comprise at least one of liver progenitor cells, hepatoblasts, vascular cells, cholangiocytes, or stromal cells. In certain embodiments, the vascular cells may comprise at least one of liver endothelial cells, liver sinusodial cells, vascular smooth muscle cells, or pericytes. In certain embodiments, the hepatoblasts may comprise at least one of fetal liver hepatoblasts, hepatoblasts derived from adult-derived liver stem cells, hepatoblasts derived from induced pluripotent stem cells, or hepatoblasts derived from embryonic stem cells. In some embodiments, the liver cells of step (a) may comprise an enriched fetal liver progenitor cell population comprising at least about 55-75% hepatic cells and not more than about 15-25% stromal cells and not more than about 5-15% endothelial cells. In certain embodiments, the liver cells of step (a) may comprise an enriched fetal liver progenitor cell population comprising about 55-75% hepatic cells, about 15-25% stromal cells, about 5-15% endothelial cells. In some embodiments, the hepatic cells are primarily liver progenitor cells. In some embodiments of the invention, the culture media used the method may comprise components that facilitate development of the at least one micro-environment niche in the bioscaffold that supports HSC expansion or differentiation. For example, in some embodiments, the culture media in step (c) may comprise at least one of stem cell factor (SCF), interleukin-6 (IL-6), or Fms-like tyrosine kinase 3 (FLT3), oncostatin-M (OSM), TGFβ3, Jagged-1, fetal bovine serum (FBS), dexamethasone, cyclic adenosine monophosphate (cAMP), Prolactin, Glucagon, niacinamide, α-lipoic acid, triiodothyronine, epidermal growth factor (EGF), high-density lipoprotein (HDL), leukemia inhibitory factor (LIF), hepatocyte growth factor (HGF), fibroblast growth factor (FGF), or human growth hormone (HGH). Also, in some embodiments, the culture media in step (c) may contain factors that stimulate activation of endogenous Notch receptors, copper chelators, or enhancers of engraftment such as PEG2 or CXCR4. However, in some embodiments, no additional factors (e.g., cytokines, growth factors) are added to the culture media of step (c). In some embodiments, the at least one micro-environment niche supports expansion or differentiation of at least one of HSC obtained from cord blood, HSC obtained from bone marrow, HSC derived from induced pluripotent stem cells, HSC derived from embryonic stem cells, or HSC derived from direct reprogramming of adult somatic cells. In some embodiments, the liver cells seeded on the bioscaffold in step (b) are cultured in culture media comprising at least one of epidermal growth factor (EGF), hepatocyte growth factor (HGF), insulin-like growth factor 1 (IGF-1), glycogen synthase kinase-3beta inhibitor (GSK3βi), or thiazovivin. In certain embodiments, the liver cells seeded on the bioscaffold in step (b) are cultured for about 5 days.

An additional embodiment of the invention is a method of producing hematopoietic cells comprising the steps of: (a) obtaining a liver organoid comprising (i) a bioscaffold derived from a decellularized donor subject liver comprising a native extracellular matrix (ECM) and native vascular channels and (ii) liver cells comprising at least one micro-environment niche that supports hematopoietic stem cell (HSC) expansion or differentiation; (b) seeding the liver organoid with HSC; (c) culturing the HSC on the liver organoid with culture media; and (d) collecting expanded HSC and/or differentiated hematopoietic cells from the culture media. In certain embodiments of the invention, the method uses liver organoids as described in the embodiments above. In some embodiments of the invention, the liver organoid comprises (i) a bioscaffold derived from a decellularized donor subject liver comprising a native extracellular matrix (ECM) and native vascular channels and (ii) liver cells comprising at least two micro-environment niches, wherein at least one micro-environment niche supports HSC expansion and at least one micro-environment niche supports HSC differentiation. In some embodiments, the liver cells of step (a) may comprise fetal liver cells. In some embodiments, the liver cells of step (a) may comprise at least one of liver progenitor cells, hepatoblasts, vascular cells, cholangiocytes, or stromal cells. In certain embodiments, the vascular cells may comprise at least one of liver endothelial cells, liver sinusodial cells, vascular smooth muscle cells, or pericytes. In certain embodiments, the hepatoblasts may comprise at least one of fetal liver hepatoblasts, hepatoblasts derived from adult-derived liver stem cells, hepatoblasts derived from induced pluripotent stem cells, or hepatoblasts derived from embryonic stem cells. In some embodiments, the liver cells of step (a) may comprise an enriched fetal liver progenitor cell population comprising at least about 55-75% hepatic cells and not more than about 15-25% stromal cells and not more than about 5-15% endothelial cells. In certain embodiments, the liver cells of step (a) may comprise an enriched fetal liver progenitor cell population comprising about 55-75% hepatic cells, about 15-25% stromal cells, about 5-15% endothelial cells. In some embodiments, the hepatic cells are primarily liver progenitor cells. In some embodiments of the invention, the liver organoid can be seeded with HSC from a variety of sources. In some embodiments of the invention, the liver organoid may be seeded with at least one of HSC obtained from cord blood, HSC obtained from bone marrow, HSC derived from induced pluripotent stem cells, HSC derived from embryonic stem cells, or HSC derived from direct reprogramming of adult somatic cells. In certain embodiments, the liver organoid may be seeded with HSC obtained from cord blood.

In some embodiments, the liver cells seeded on the bioscaffold in step (b) are cultured in culture media comprising at least one of epidermal growth factor (EGF), hepatocyte growth factor (HGF), insulin-like growth factor 1 (IGF-1), glycogen synthase kinase-3beta inhibitor (GSK3βi), or thiazovivin. In certain embodiments, the liver cells seeded on the bioscaffold in step (b) are cultured for about 5 days. In some embodiments of the invention, the culture media used the method may comprise components that facilitate development of the at least one micro-environment niche in the bioscaffold that supports HSC expansion or differentiation. For example, in some embodiments, the culture media in step (c) may comprise at least one of stem cell factor (SCF), interleukin-6 (IL-6), or Fms-like tyrosine kinase 3 (FLT3), oncostatin-M (OSM), TGFβ3, Jagged-1, fetal bovine serum (FBS), dexamethasone, cyclic adenosine monophosphate (cAMP), Prolactin, Glucagon, niacinamide, α-lipoic acid, triiodothyronine, epidermal growth factor (EGF), high-density lipoprotein (HDL), leukemia inhibitory factor (LIF), hepatocyte growth factor (HGF), fibroblast growth factor (FGF), or human growth hormone (HGH). Also, in some embodiments, the culture media in step (c) may contain factors that stimulate activation of endogenous Notch receptors, copper chelators, or enhancers of engraftment such as PEG2 or CXCR4. However, in some embodiments, no additional factors (e.g., cytokines, growth factors) are added to the culture media of step (c). In certain embodiments, the culture media in step (c) may comprise at least one of stem cell factor (SCF), fibroblast growth factor (FGF), interleukin-6 (IL-6), Fms-like tyrosine kinase 3 (FLT3), or leukemia inhibitory factor (LIF). In some embodiments, the liver organoid may be seeded with at least one of HSC obtained from cord blood, HSC obtained from bone marrow, HSC derived from induced pluripotent stem cells, HSC derived from embryonic stem cells, or HSC derived from direct reprogramming of adult somatic cells. In certain embodiments, the differentiated hematopoietic cells may comprise hematopoietic progenitor cells (HPC), myeloid progenitor cells (MPC), lymphoid progenitor cells (LPC), lymphocytes, granulocytes, macrophages, erythrocytes, or platelets. In some embodiments, the differentiated hematopoietic cells may comprise an enriched population of differentiated erythrocytes. In some embodiments, where an enriched population of differentiated erythrocytes is to be obtained, the culture media in step (c) may comprise erythropoietin (EPO).

In another embodiment, the invention is a cell population comprising hematopoietic cells produced by a process comprising (a) obtaining a liver organoid comprising (i) a bioscaffold derived from a decellularized donor subject liver comprising a native extracellular matrix (ECM) and native vascular channels and (ii) liver cells comprising at least one micro-environment niche that supports hematopoietic stem cell (HSC) expansion or differentiation, (b) seeding the liver organoid with HSC, (c) culturing the HSC on the liver organoid with culture media; and (d) collecting hematopoietic cells from the culture media. In some embodiments, the hematopoietic cells may comprise expanded HSC and/or differentiated hematopoietic cells. In certain embodiments, the organoid may comprise (i) a bioscaffold derived from a decellularized donor subject liver comprising a native extracellular matrix (ECM) and native vascular network and (ii) liver cells comprising at least two micro-environment niches, wherein at least one micro-environment niche supports HSC expansion and at least one micro-environment niche supports HSC differentiation. In some embodiments, the liver cells of step (a) may comprise fetal liver cells. In some embodiments, the liver cells of step (a) may comprise at least one of liver progenitor cells, hepatoblasts, vascular cells, cholangiocytes, or stromal cells. In certain embodiments, the vascular cells may comprise at least one of liver endothelial cells, liver sinusodial cells, vascular smooth muscle cells, or pericytes. In certain embodiments, the hepatoblasts may comprise at least one of fetal liver hepatoblasts, hepatoblasts derived from adult-derived liver stem cells, hepatoblasts derived from induced pluripotent stem cells, or hepatoblasts derived from embryonic stem cells. In some embodiments, the liver cells of step (a) may comprise an enriched fetal liver progenitor cell population comprising at least about 55-75% hepatic cells and not more than about 15-25% stromal cells and not more than about 5-15% endothelial cells. In certain embodiments, the liver cells of step (a) may comprise an enriched fetal liver progenitor cell population comprising about 55-75% hepatic cells, about 15-25% stromal cells, about 5-15% endothelial cells. In some embodiments, the hepatic cells are primarily liver progenitor cells.

In some embodiments, the liver cells seeded on the bioscaffold in step (b) may be cultured in culture media comprising at least one of epidermal growth factor (EGF), hepatocyte growth factor (HGF), insulin-like growth factor 1 (IGF-1), glycogen synthase kinase-3beta inhibitor (GSK3βi), or thiazovivin. In some embodiments, the liver cells seeded on the bioscaffold in step (b) may be cultured for about 5 days. The culture media in step (c) may exclude exogenous growth factors, and wherein expanded HSC and/or immature hematopoietic stem cells are collected in step (d). In certain embodiments, the culture media in step (c) may comprise at least one of stem cell factor (SCF), fibroblast growth factor (FGF), interleukin-6 (IL-6), Fms-like tyrosine kinase 3 (FLT3), or leukemia inhibitory factor (LIF). In some embodiments, the culture media in step (c) may comprise at least one exogenous growth factor, and wherein differentiated hematopoietic stem cells are collected in step (d). In certain embodiments, the culture media in step (c) may comprise at least one of stem cell factor (SCF), interleukin-6 (IL-6), Fms-like tyrosine kinase 3 (FLT3), oncostatin-M (OSM), TGFβ3, Jagged-1, fetal bovine serum (FBS), dexamethasone, cyclic adenosine monophosphate (cAMP), Prolactin, Glucagon, niacinamide, α-lipoic acid, triiodothyronine, epidermal growth factor (EGF), high-density lipoprotein (HDL), leukemia inhibitory factor (LIF), hepatocyte growth factor (HGF), fibroblast growth factor (FGF), or human growth hormone (HGH). In certain embodiments, the culture media in step (c) may comprise at least one of stem cell factor (SCF), fibroblast growth factor (FGF), interleukin-6 (IL-6), Fms-like tyrosine kinase 3 (FLT3), or leukemia inhibitory factor (LIF). In some embodiments, the liver organoid may be seeded with at least one of HSC obtained from cord blood, HSC obtained from bone marrow, HSC derived from induced pluripotent stem cells, HSC derived from embryonic stem cells, or HSC derived from direct reprogramming of adult somatic cells. In certain embodiments, the differentiated hematopoietic cells may comprise hematopoietic progenitor cells (HPC), myeloid progenitor cells (MPC), lymphoid progenitor cells (LPC), lymphocytes, granulocytes, macrophages, erythrocytes, or platelets. In some embodiments, the differentiated hematopoietic cells may comprise an enriched population of differentiated erythrocytes. In some embodiments, where an enriched population of differentiated erythrocytes is to be obtained, the culture media in step (c) may comprise erythropoietin (EPO).

In some embodiments of the invention, the culture media used in the method may comprise components that facilitate development of the at least one micro-environment niche in the bioscaffold that supports HSC expansion or differentiation. In some embodiments of the invention, HSC (i.e., expanded HSC) and/or immature hematopoietic stem cells are collected from the culture media. The culture media may exclude growth factors when expanded HSC and/or immature hematopoietic stem cells are collected from the culture media. For example, in some embodiments, the culture media that excludes growth factors may comprise at least one of stem cell factor (SCF), fibroblast growth factor (FGF), interleukin-6 (IL-6), Fms-like tyrosine kinase 3 (FLT3), or leukemia inhibitory factor (LIF). Also, in some embodiments, the culture media may contain factors that stimulate activation of endogenous Notch receptors, copper chelators, or enhancers of engraftment such as PEG2 or CXCR4.

In other embodiments of the invention, differentiated hematopoietic cells are collected from the culture media. In some embodiments of the invention, the differentiated hematopoietic cells comprise hematopoietic progenitor cells (HPC), myeloid progenitor cells (MPC), lymphoid progenitor cells (LPC), lymphocytes, granulocytes, macrophages, erythrocytes, or platelets. In some embodiments of the invention, the culture media may contain at least one growth factor when differentiated hematopoietic stem cells are collected in from the culture media. For example, the culture media comprising at least one growth factor may comprise at least one of stem cell factor (SCF), interleukin-6 (IL-6), or Fms-like tyrosine kinase 3 (FLT3), oncostatin-M (OSM), TGFβ3, Jagged-1, fetal bovine serum (FBS), dexamethasone, cyclic adenosine monophosphate (cAMP), Prolactin, Glucagon, niacinamide, α-lipoic acid, triiodothyronine, epidermal growth factor (EGF), high-density lipoprotein (HDL), leukemia inhibitory factor (LIF), hepatocyte growth factor (HGF), fibroblast growth factor (FGF), or human growth hormone (HGH). For example the culture media may contain at least one of stem cell factor (SCF), fibroblast growth factor (FGF), interleukin-6 (IL-6), Fms-like tyrosine kinase 3 (FLT3), or leukemia inhibitory factor (LIF). In some embodiments, an enriched population of differentiated erythrocytes is collected. In certain embodiments, differentiation of erythrocytes is promoted. In such embodiments, the culture media will at least include erythropoietin (EPO). However, in some embodiments, no additional factors (e.g., cytokines, growth factors) are added to the culture media. In some embodiments, the culture media does not include growth factors and/or cytokines. In some embodiments, the culture media is serum-free culture media. In some embodiments of the invention, both expanded HSC and differentiated hematopoietic cells are collected from the culture media.

Some embodiments of the invention encompass use of factors in the culture media used in generating the liver organoids of the invention and/or the culture media used in culturing HSC in the liver organoids of the invention to produce hematopoietic cells (e.g., HSC and more differentiated hematopoietic cells). Some extrinsic signaling molecules including colony-stimulating factors (CSFs) and interleukins (ILs) that activate intracellular signaling molecules such as kinases are known to influence HSC pluripotency, proliferation, and lineage commitment. Approaches of HSC culturing in vitro that included or involved activation of endogenous Notch receptors, copper chelators [1], or enhancers of engraftment such as PEG2 [26] or CXCR4 [27] have shown some potential for ex vivo expansion or engraftment of CB-HSPC. In some embodiments of the invention, the culture media used to generate the liver organoids or the culture media used to produce hematopoietic cells may comprise one or more of these types of factors. In some embodiments, the different culture media of the invention may comprise one or more cytokines, chemokines, receptor ligand molecules, or intracellular signaling molecules.

Proteins (such as growth factors) or other additives (such as antibiotics, anti-inflammatories, and modulators of the immune response) may also be added to the cell and/or bioscaffold preparations, or to the culture media, at any time. Also, various treatments may be applied to enhance adherence of cells to the bioscaffold and/or to each other. Appropriate treatments are described, for example, in U.S. Pat. No. 5,613,982. Such treatments include the application of various proteins, e.g., growth factors or extracellular matrix proteins to the bioscaffold substrate or to the growing construct. For example, collagen, elastin, fibronectin, laminin, or proteoglycans may be applied to the bioscaffold. The bioscaffold can be impregnated with growth factors such as nerve growth factor (NGF), aFGF, bFGF, PDGF, TGFβ, VEGF, GDF-5/6/7, BMP-1/2/3/4/5/6/7/13/12/14, IGF-1, etc., or these agents may be provided in the culture medium.

As noted above, the liver organoid of the invention, and methods relating thereto, are useful for in vitro culturing of HSC such that HSC can be expanded and/or differentiated using readily available sources of HSC. In some embodiments of the invention, the source of HSC for culturing is cord blood. However, in some embodiments of the invention, HSC may be obtained from other sources.

For example, in some embodiments of the invention, the source of HSC is bone marrow. Bone marrow can be an appropriate source of HSC for culturing using the liver organoid of the invention in instances where a subject has certain cancers of the blood or bone marrow (e.g., multiple myeloma or leukemia) and treatment of the subject with radiation or chemotherapy destroys the subject's immune system. Prior to treatment of the cancer, bone marrow can be harvested from the subject and subsequently cultured in vitro using the liver organoid and methods of the invention. The hematopoietic cells generated using the invention, particularly the HPC, can then be transplanted back into the subject after the cancer treatment is completed.

In some embodiments of the invention, HSC from natural sources (e.g., bone marrow, cord blood) is enriched prior to culturing in the liver organoids. HSC (and their differentiated progeny) can be identified by the expression of specific cell surface lineage markers such as Cluster of Differentiation (CD) proteins and cytokine receptors. In some embodiments of the invention, HSC may be enriched by active selection of the HSC cell population using a cell surface marker characteristic of HSC. Human HSC are characterized by the following cell surface markers: aldehyde dehydrogenase high (ALDH(hi)), CD34+, CD133+, CD49F, CD59+, CD90/Thy1+, CD38low/(−), c-Kit(−)/low, and Lin (−). As such, in some embodiments, HSC are selected and/or enriched by selecting for cells expressing any one of these markers. In other embodiments of the invention, HSC may be enriched by selection and removal of lineage-committed cells using cell surface markers characteristic of lineage-committed cells.

In some embodiments of the invention, the source of HSC is embryonic stem cells (ES cells). ES cells are pluripotent stem cells derived from the inner cell mass of a blastocyst, an early-stage embryo. ES cells can be induced to become HPC for use in embodiments of the invention.

In other embodiments of the invention, the source of HSC is induced pluripotent stem cells (iPS cells or iPSC). iPS cells are a type of pluripotent stem cell artificially derived from a non-pluripotent cell—typically an adult somatic cell—by inducing expression of specific genes (e.g., at least Oct-3/4 (Pou5f1), Sox2). iPS cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. iPS cells can be generated from a variety of adult somatic cells, including, e.g., stomach cells, liver cells, skin cells and blood cells. iPS cells can be induced to become HPC for use in embodiments of the invention. As the iPS cells can be obtained from a subject in need of a HSC transplantation, the HPC derived therefrom may result in improved transplantation outcome for the subject by reducing the risk of host-vs-graft disease.

In some embodiments of the invention, the HSC are directly reprogrammed adult somatic cells. Direct reprogramming, or transdifferentiation, is the direct conversion of one cell type to another without undergoing an intermediate pluripotent state or progenitor cell type. Reprogramming of cells to a different cell type is usually done by either somatic cell nuclear transfer (SCNT) or through expression of transcription factors or microRNA precursors. Direct reprogramming can be performed using a variety of cells types, including, e.g., skin, muscle, blood, pancreatic, and neurons. Studies have shown that adult somatic cells (e.g., fibroblasts) can be directly reprogrammed into multipotent blood progenitor cells [65].

As such, the invention encompasses liver organoids (i.e., bioengineered human liver tissue constructs) that allow functional and efficient expansion of CB-HSPC using a more physiological condition. The invention further encompasses development of a new approach to expand CB-HPSC using bioengineered human fetal liver-like organoids (tissue constructs). In some embodiments of the invention, the liver organoids are built upon a natural 3-D liver extracellular matrix (i.e., bioscaffold), into which seeded liver cells (e.g., fetal liver-derived mesenchymal cells, hepatoblasts, and/or endothelial cells) become functionally integrated and assembled. In embodiments of the invention, the bioscaffold contains necessary elements to mimic the fetal liver microenvironmental niches known to promote rapid expansion of HSC during development. In addition, in some embodiments of the invention, the liver organoids provide a model system in which to dissect the role of its individual cellular and matrix components in supporting CB maintenance, expansion, and differentiation.

Figure 13:
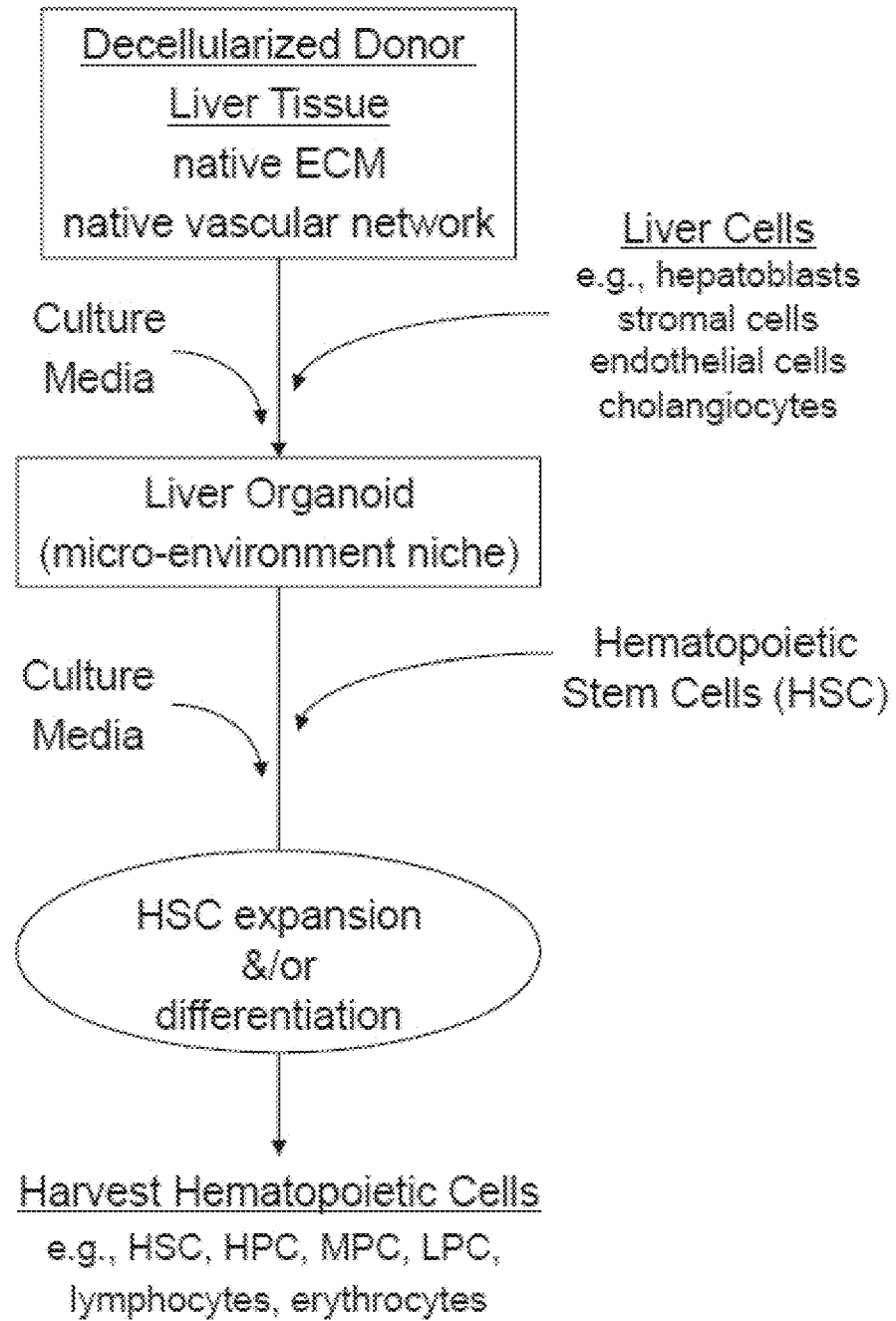
FIG. 13 shows a schematic in accordance with alternate aspects of the invention that outlines the steps involved in producing a liver organoid and using the liver organoid to culture HPC and produce hematopoietic cells.

As shown in FIG. 13, in some embodiments of the invention, a liver organoid may be produced that contains at least one microenvironment niche that supports HSC expansion or differentiation. In embodiments of the invention, a decellularized donor liver tissue is used as the bioscaffold for a liver organoid. The bioscaffold has the native ECM and native vascular channels of the donor liver tissue. Liver cells are then seeded onto the bioscaffold and cultured with culture media. The liver cells may be hepatoblasts, stromal cells, cholangiocytes, endothelial cells, or any combination thereof. In some embodiments of the invention, culturing the liver cells with the bioscaffold results in the production of a liver organoid comprising at least one micro-environment niche. In certain embodiments of the invention, the liver organoid comprises at least two micro-environment niches—at least one niche that supports HSC expansion and at least one niche that supports HSC differentiation. In some embodiments of the invention, the liver organoid is seeded with HSC and the cells are cultured in the presence of culture media to support the growth of hematopoietic cells. The cultured hematopoietic cells may be HSC, early progenitor cells such as HPC, MPC or LPC, or further differentiated cells such as the lymphocytes, granulocytes, and macrophages of the immune system, or erythrocytes and platelets. As show in FIG. 15A, in some embodiments, CD34+ CB-derived HSCs expand progressively and efficient on the organoids cultured with long term HSC. In some embodiments, HSCs may be expanded continuously for at least 7 weeks. In some embodiments, the liver organoid discs support expansion of multipotent progenitor cells, as identified in colony-forming assays as CFU-GEMM. In some embodiments, the CFU-GEMM cell population is expanded 20-fold over 7 weeks of culturing. In addition, in some embodiments, the liver organoid discs supported maintenance of granulocyte, monocyte progenitors, as identified in colony-forming assays as CFU-GM for at least 6 weeks of culturing.

The present invention is explained in greater detail in the following non-limiting Examples.

EXAMPLES

Example 1

Preparation and Characterization of Bioengineered Liver Organoids

A. Preparation of Liver Organoids
Liver Harvesting and Decellularization.
Four to five weeks old ferret livers (Marshall Bioresources, New York) are utilized for decellularization and disc preparation. Alternatively, human, rodent (e.g., rat, mouse), pig, monkey, ape, bovine and sheep livers can be used. Livers are harvested with intact vessels and the portal vein was cannulated with a 16-gauge cannulae (Cathlon® Clear, Johnson & Johnson Medical Ltd., Arlington, Tex., USA). The livers are then connected to a pump (Masterflex L/S peristaltic pump with Masterflex L/S easy load pump head and L/S 14 gauge tubing, Cole-Palmer, Vernon Hills, Ill., USA) and perfused with 2 liters of distilled water at the rate of 6 mL/min. The livers are then perfused with 4 liters of detergent made up of 1% Triton-X 100 (Sigma-Aldrich Co., St. Louis, Mo., USA) with 0.1% Ammonium hydroxide (Sigma-Aldrich Co., St. Louis, Mo., USA). Finally, the livers are perfused with 8 liters of distilled water to wash out the decellularization detergent.

Acellular Liver Disc Preparation.
Decellularized livers are cut into small lobes and embedded in plastic molds using TissueTek® O.C.T. Compound (Sakura® Finetek USA, Torrance, Calif., USA) and flash froze with liquid nitrogen. FIG. 1A (top left) and FIG. 2A show images of decellularized ferret liver. The cryopreserved liver lobes are mounted onto a cryotome (Leica CM1950 Crystat) to obtain liver ECM discs. The cryotome temperature is set to about −8° C. to −10° C. in order to maintain the liver lobes at warmer temperatures, facilitating thick and intact sectioning of liver lobes. The sections are cut to about 300 µm thickness. To generate a disc from the liver sections, an about 8 mm diameter biopsy punch equipped with a plunger is used in order to place the discs in the wells of, e.g., a 48-well plate. The 48-well plate is kept inside the cryotome until the desired number of discs is generated. The discs are then air-dried for up to 4-6 hours or until they are almost dry. Following the drying step, the discs are washed carefully with multiple washes of PBS and kept in PBS at 4° C. until ready for sterilization. The discs are sterilized by gamma irradiation at a dose of 1.5 Mrad using a Wheeler Cobalt-60 Gamma Irradiator.

Isolation and Propagation of Enriched hFLPCs. Human fetal livers at developmental stages between approximately 18 and 21 weeks of gestation are obtained (e.g., Advanced Biological Resources, Alameda, Calif.). Detailed description for isolation of hFLPCs has been described previously [12, 78]. Briefly, nonhepatic tissue is removed by scalpel and livers are enzymatically digested at 37° C. by collagenase type IV (Worthington Biochemical Corporation, New Jersey) and deoxyribonuclease to yield small tissue clumps. Following digestion, a neutralizing wash using DMEM containing 10% FBS is performed, followed by two washed in Hepatocyte Washing Media (Gibco) (sedimentation at 1200-1500 g). The resultant parenchymal cell clumps (predominantly hepatoblasts) are resuspended in culture medium and then passed through a 100 µm nylon mesh, followed by a 40 µm nylon mesh, to yield highly enriched suspensions of single cell and small cell aggregates of 3-8 hepatoblasts. The cells are then resuspended in culture medium and then overlaid onto a Histopaque®-1077 density gradient (Sigma-Aldrich, 10771) and spun (400 g for 30 minutes) to separate the hematopoietic and nonparenchymal cells from the parenchymal cell fraction. The resultant pellet is highly enriched in fetal hepatoblasts (single and small cell aggregates), liver stem cells, and red blood cells. The interface between layers contains enriched amounts of non-parenchymal cells (stromal, endothelial). The lower fraction cell pellet is resuspended in media and plated on Collagen-IV (5 mg/cm$^2$) and Laminin (1 mg/cm$^2$) coated 15-cm culture plates and incubated at 37° C. After 24 hours, the cells are washed to remove blood cells. The enriched hFLPCs are cultured until enough cells are produced to seed onto acellular discs. The enriched hFLPCs may also be cultured in suspension.

Different culture medias can be used to culture the enriched hFLPCs. For example, they can be cultured in liver progenitor cell (LPC) seeding medium as described in [12, 78] made of Advanced RPMI (Invitrogen, 12633012) containing 1% antibiotics/antimycotic (Invitrogen), 10 mg/L Ascorbic Acid, 0.04 mg/L dexamethasone, 2.45 mg/L cAMP, 10 µ/L hProlactin, 1 mg/L hGlucagon, 10 mM niacinamide, 0.105 mg/L alpha lipoic acid, 67 ng/L triiodothyronine (Sigma-Aldrich), 40 ng/mL human Epidermal Growth Factor (hEGF) (R&D Systems, Inc., Minneapolis, Minn., USA), 10 mg/L hHDL (Cell Sciences, Canton, Mass., USA), 20 ng/mL human hepatocyte growth factor (hHGF) (eBiosciences, San Diego, Calif., USA), 3.33 ng/mL human Growth Factor (hGH), 76 µl/L Free Fatty Acid Mix, and 0.056 µg/L (D-Ala2, D-Leu5)-Enkephalin Acetate, supplemented with 5% Fetal Bovine Serum (FBS) and 1.2 mg/50 mL of BD Matrigel™ (BD Biosciences) for the first 24 hours and then LPC maintenance medium (same recipe but lacking FBS and Matrigel™). Alternatively, the enriched hFLPCs can be cultured in minimal LPC media made of Kubota Medium (KM) containing RPMI 1640 containing 10 mg/L Ascorbic Acid, 0.04 mg/L Dexamethasone (or 10$^{-7}$M hydrocortisone), 5 mM Niacinamide, 76 µl/L Free Fatty Acid Mix, 5 mg/L insulin, 10 mg/L transferrin, 5 µg/L sodium selenite and 0.5 g of bovine serum albumin (BSA), and supplemented with 10 ng/mL human Epidermal Growth Factor (hEGF) (R&D Systems, Inc., Minneapolis, Minn., USA) and 10 ng/mL hepatocyte growth factor (HGF). KM is a serum-free and growth factor-free medium optimized for ex vivo expansion of hepatic progenitor cells [69]. In addition, they can be cultured in hepatic fetal liver progenitor (hFLP) medium made of KM supplemented with 10 µM thiazovivin, 20 ng/ml IGF-1 and 50 nM Glycogen Synthase Kinase-3beta inhibitor (GSK3βi). Culturing the enriched hFLPCs in either the minimal LPC medium or the hFLP medium results in a less differentiated cell population for seeding on the acellular discs and improved seeding and growth on the discs as compared to when cultured using the LPC seeding and maintenance medias.

This protocol could be modified to isolate fetal liver mesenchymal stem cells (MSC) and hepatic sinusoidal endothelial cells (HSEC) from the pellet following density gradient separation using fluorescence-activated cell sorting with antibodies to Stro-1 and VE-cadherin and/or CD31. These markers have enabled consistent isolation of pure populations of MSC from a variety of tissues [32-36] and HSEC, respectively. These three populations can then be seeded onto the decellularized discs (e.g., 600,000 hepatoblasts, 200,000 MSC, and 200,000 HSEC per well/disc) for culturing as described below.

Progenitor Cell Seeding on Acellular Discs.

Sterilized discs are incubated with medium for 30-45 minutes prior to cell seeding and then air dried in biosafety cabinet. hFLPCs are harvested from culture plates using collagenase IV and then counted. hFLPCs ($0.5 \times 10^6$-$1.0 \times 10^6$ cells) are resuspended in 10 µl volume in medium for each disc. The cell suspension (10 µl) is slowly pipetted on top of each disc and incubated for about an hour at 37° C. for attachment before adding additional medium to a final volume of 500 µl (per well). As a 2D (monolayer) control, the same number of hFLPCs can be seeded on a collagen IV and laminin coated 48-well tissue culture plates. The medium used for these steps can be either the LPC seeding medium or the minimal LPC medium. After 24 hours, the discs and 2D control cells are incubated with liver differentiation medium made of Advanced RPMI (Invitrogen, 12633012) containing 1% antibiotics/antimycotic (Invitrogen), 10 mg/L Ascorbic Acid, 0.04 mg/L dexamethasone, 2.45 mg/L cAMP, 10 µ/L hProlactin, 1 mg/L hGlucagon, 10 mM niacinamide, 0.105 mg/L alpha lipoic acid, 67 ng/L triiodothyronine (Sigma-Aldrich), 40 ng/mL human Epidermal Growth Factor (hEGF) (R&D Systems, Inc., Minneapolis, Minn., USA), 10 mg/L hHDL (Cell Sciences, Canton, Mass., USA), 20 ng/mL human hepatocyte growth factor (hHGF), 3.33 ng/mL human Growth Factor (hGH), 76 µl/L Free Fatty Acid Mix, and 0.056 µg/L (D-Ala2, D-Leu5)-Enkephalin Acetate, supplemented with 10 µg/L Oncostatin M. The seeded discs are then cultured at 37° C. The culture medium is changed every 24 hours. FIG. 1 shows an overview of this process. Over a period of 3 weeks, a three dimensional organoid has formed through recellularization of the ECM disc.

Characterization of Enriched hFLPCs.

Fluorescence activated cells sorting (FACS) analysis of the enriched hFLPC population can be performed after 1 week of culturing. Antibodies for different cell types can be used to assess the proportion of cells in the enriched population: putative hepatoblast markers (e.g., EpCAM, ICAM1, α-fetoprotein (αFP), ALB, CK18); stromal cells (αSMA, CD105), endothelial cells (CD31). Based on repeated experiments, the enriched hFLPC population has about 55-75% hepatic cells (primarily liver progenitor cells), about 10-25% stromal cells, and about 5-15% endothelial cells when cultured using LPC seeding medium and LPC maintenance medium. Representative histograms are shown in FIG. 2G. Use of minimal LPC seeding medium and minimal LPC maintenance medium results in less differentiation of the initial cell populations (empirical analysis; data not shown). Use of hFLP medium to culture the enriched hFLPCs also results in less differentiation of the initial cell populations (less even than with the minimal LPC seeding and maintenance medias) and favors proliferation of the hepatic cells in the population over the stromal and endothelial cells (empirical analysis; data not shown).

B. Characterization of Liver Organoids

In a first experiment, the acellular discs were prepared using decellularized ferret liver as described above in Section A (FIG. 2A). The ECM discs were seeded with enriched hFLCPs and cultured as described above in Section A using LPC seeding and maintenance media. As an alternative, the organoids can be prepared using minimal LPC medium or hFLP medium instead. The seeded discs were cultured for 3 weeks and then harvesting for immunohistochemical and molecular analysis. Over the course of the incubation, the cells infiltrated the ECM and grew into 3-D liver organoids that formed biliary and hepatocytic structures like that of native liver (FIGS. 2B and 2C), and expressed common hepatic markers (FIG. 2D-F). Specifically, bile duct-specific apical sodium dependent bile transporter (ASBT) and EpCAM expressing hepatocytic cells were observed in ductular structures present throughout these constructs (FIG. 2D). Hepatocyte/hepatoblast clusters were also observed through the entire tissue expressing hepatic specific cytochrome P450 2A (CYP2A) (FIG. 2E), as well as albumin and α-fetoprotein (AFP) (FIG. 2F).

For hepatocyte functional analysis, culture medium was collected after the three week incubation. The media was stored at −80° C. until it was used for analysis. For analyzing albumin synthesis, albumin ELISA assay (Bethyl Laboratories Inc.) was carried out on each samples in triplicates. The albumin concentrations were normalized per mg of DNA. The media was also analyzed in the same fashion for urea secretion using a Quantichrome™ Urea Assay Kit (BioAssay Systems, Inc.). To assess drug metabolic activity, the liver organoids were first incubated with phenobarbital and 3-MC in order to induce enzymatic activity and then incubated with diazepam and 7-ethoxycoumarin, two compounds known to be metabolized by liver enzymes. After 48 hours, media samples were collected and analyzed by mass spectrometry (FIGS. 3C and 3D), and compared with standards of individual metabolites (FIGS. 3A and 3B). After enzymatic activation, the media collected from the liver organoid discs was found to contain Phase-1 metabolites Temazepam, Nordiazepam and 7-hydroxycoumarin. These results support the conclusion that the engineered liver tissue is functional, over a long period of time (3 weeks), and possess metabolic capabilities of a native human liver.

The seeded fetal liver cells became fully functional upon integration into the scaffold, secreting albumin and urea (FIGS. 3E and 3F), and acquiring the ability to correctly metabolize common drugs such as diazepam and 7-ethoxycoumarin (FIG. 3A-D), which are functionalities that fetal livers have, though to a lesser extent that adult liver. The degree of differentiation or function of these fetal liver cells will be manipulated using culture conditions. To generate a more immature liver organoid, culture media containing very few growth factors will be used (e.g., selected from those described herein, amongst others).

In a second experiment, the liver organoids were prepared as described above in Example 1, Section A using LPC seeding and maintenance media. Alternatively, the organoids can be prepared using minimal LPC medium or hFLP medium instead. After seeding with hFLPCs, the discs were cultured for 3 weeks, with harvesting of cells at 1 week and 3 weeks for immunohistochemical and molecular analysis. Assays assessing albumin and urea synthesis and IHC analyses were performed as described above. Gene expression analyses were performed by RT-PCR after harvesting the organoids. Drug metabolism activity in the organoids was assessed after 1 week and 3 weeks of culturing. The liver organoids were first incubated with phenobarbital and 3-MC in order to induce enzymatic activity and then incubated with diazepam and 7-ethoxycoumarin. After 3, 6, 12, and 24 hours, media samples were collected and analyzed by mass spectrometry. After enzymatic activation, the media collected from the liver organoid discs was assessed for the presence of Phase-1 metabolites Temazepam, Nordiazepam and 7-hydroxycoumarin.

Figure 5B:
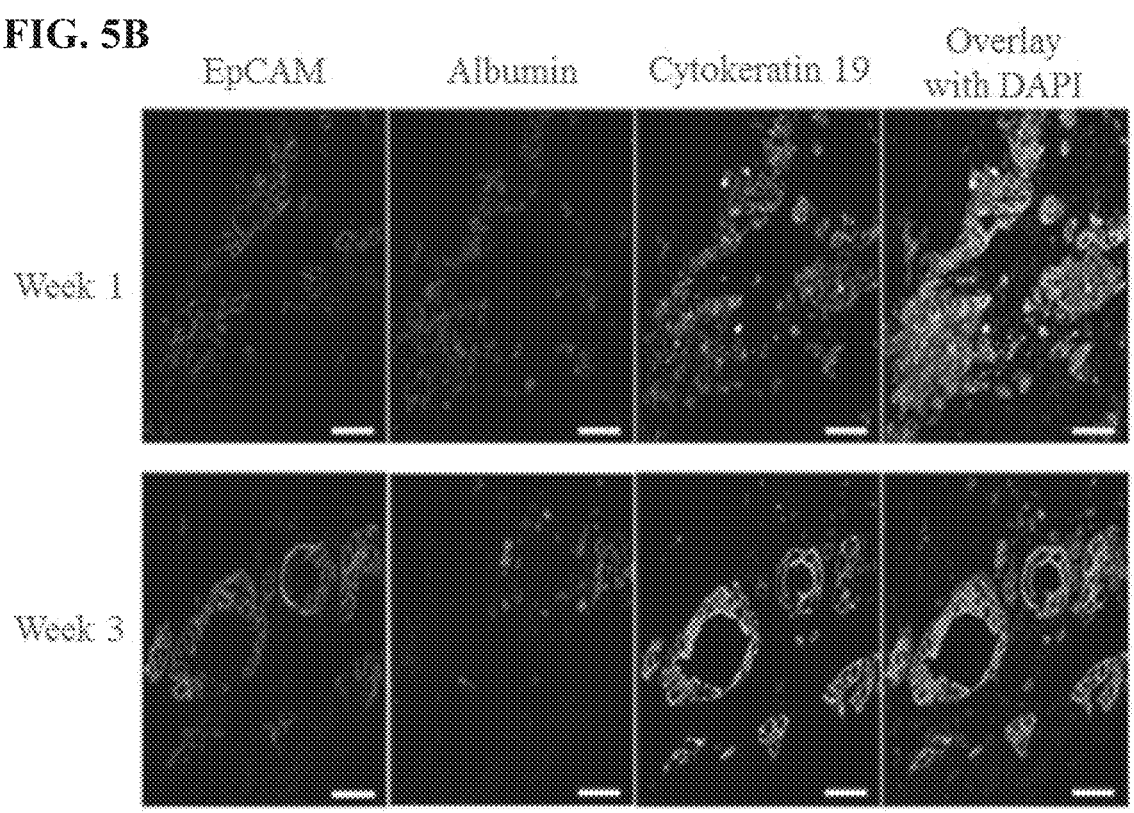

The progressive cellular organization and cell differentiation of the organoid was observed. RT-PCR analysis was used to assess expression of genes characteristic of biliary cells (CK7, CK19), hepatic cells (ALT, AST), hepatoblasts (AFP, ALB, CYP3A7), hepatocytes (transferrin), and proliferating cells (Ki-67). This analysis showed more extensive differentiation, proliferation and higher survival of hFLPCs in the 3D liver organoids than in 2D tissue culture dishes coated with collagen IV and laminin (FIG. 5A). Specifically, after 21 days in the 3D liver organoids, higher expression of proteins and enzymes of mature liver tissue including GST, ALT, transferrin and CYP 3A7 was observed, while maintaining high expression of Ki67 indicating cell proliferation. Further analysis, showed large clusters of cells expressing fetal hepatoblast markers (ALB$^+$/CK19$^+$/EpCAM$^+$) after 1 week culture, suggesting no lineage specification at that stage (FIG. 5B; top panels). After 3 weeks there was a clear change in cell phenotype including ALB$^+$/CK19$^-$ clusters and ALB$^-$/CK19$^+$ ductular structures, suggesting lineage specification into hepatocytes and cholangiocytes, respectively (FIG. 5B; bottom panels). Also, EpCAM expression decreased over time and expression shifted from the cytoplasm to the cell membrane, as is observed in vivo.

Whole genome expression analysis of the organoid cells was also performed using Affymetric GeneChip® Human Genome U133 Plus 2.0 Arrays. Data analysis was performed using Gene Set Enrichment Analysis (GSEA) (available at http://www.broadinstitute.org/gsea/index.jsp). GSEA is a computational tool to help in interpreting results from gene experiment analyses when comparing two conditions and an a priori collection of predefined gene sets. GSEA provides a significance to each gene set based on how differentially expressed that gene set is to the biological experiment. Gene sets were chosen from the Molecular Signatures Database (MSigDB): a large range of liver genes of interest (e.g., liver progenitor, hepatic, biliary, carbohydrate metabolism, drug metabolism, fatty acid metabolism), reactome synthesis of bile acids and bile salts, mature liver cells (e.g., hepatocyte and biliary). The genes in these panels are listed at the end of this section. Expression in liver organoid discs after 1 week or 3 weeks culturing was compared to expression in adult and fetal tissue as well as whole recellularized organ prepared as described in [12, 78]. This analysis showed a trend of progressive differentiation of the liver cells of the organoids showing a gene expression pattern for putative liver genes more similar to adult than fetal human liver at 3 weeks (FIG. 6). This pattern was further confirmed in biliary and hepatic gene sets (FIG. 7 and FIG. 8, respectively).

Hepatocyte maturation is a dynamic process highlighted by changes in levels of various cytokines and transcription factors associated with differentiation and maturation of hepatoblast into hepatocytes. Transcriptional switch from α-fetoprotein (AFP) to albumin resulting into loss of AFP expression and increased levels of albumin is one of the hallmark of hepatocyte maturation. hFLPCs displayed this progressive maturation into hepatocytes within the organoids as clusters of cells expressed both AFP and albumin after 1 week of differentiation, similar to fetal liver (FIG. 9A, left panel), and subsequently lost AFP expression as the cells matured within the organoids after 3 weeks of differentiation, resembling adult liver (FIG. 9A, right panel). Further characterization of these clusters using immunohistochemical analysis showed expression of several adult hepatocyte markers such as HNF4α, alpha-1-antitrypsin (A1AT) and cytochrome P450 3A4 (FIG. 9B). RT-PCR analysis further confirmed expression of hepatocyte differentiation markers including HNF4α and AST (FIG. 10A). Differentiated hepatocytes also showed high expression of different cytochrome P450 isoforms whether they were induced with the drugs phenobarbital and 3-methylcholanthrene (FIG. 10B) or not (FIG. 10C). The liver organoids also showed significantly higher albumin and urea secretion compared with hFLPCs differentiated in culture plates (FIG. 11A). Furthermore, the liver organoids metabolized diazepam into temazepam and nordiazepam, and 7-ethoxy coumarin into 7-hydroxy coumarin, both phase I metabolites (FIG. 11B).

Figure 12C:
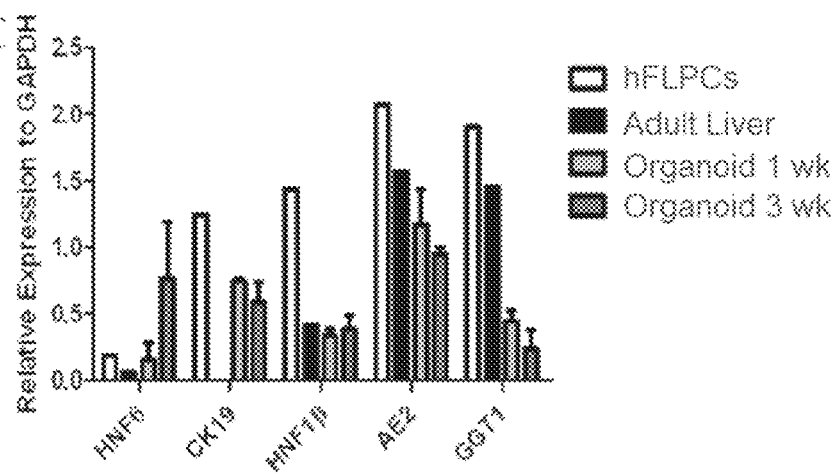

During fetal liver development, liver progenitor cells also differentiate into cholangiocytes that give rise to bile ducts through unique morphogenesis. This process lacks in many of the in vitro liver organoid systems but the liver organoid system described above allows for concomitant bile duct morphogenesis. Four different stages of bile duct formations were observed in these organoids, comparable to the duct developmental stages observed in human fetal liver (FIG. 12A). Significantly, the ECM composition around these biliary duct cells was identical to that observed during the fetal duct morphogenesis process including laminin in the basal membrane surrounding the CK19⁻ biliary duct cells (cholangiocytes). These ductular structures were positive for CK19, EpCAM and SOX9, constitutive markers of cholangiocytes, and as expected for this stage of specification, lacked albumin expression (FIG. 12B; top row). These structures also exhibited typical bile duct apical-basal polarity, indicated by the presence of primary cilia (antitubulin) and a bile salt transporter (ABST) in the apical membrane and beta-catenin on the baso-lateral membrane (FIG. 12B; bottom row). RT-PCR analysis also showed up-regulation of HNF6 (a critical transcription factor in bile duct morphogenesis), HNF1β (a transcription factor important for lineage specification of hepatoblasts into cholangiocytes), anion exchange factor 2 (AE2); and GGT1, all markers of mature cholangiocytes (FIG. 12C).

Genes in FIG. 6 (in Order): SLCO1B1, SLC27A2, C1OB, C1OC, CYP3A4, CYP2C9, HNF4A, CYP8B1, BAAT, CYP3A4, AKR1D1, SLCO1B3, TPMT, CYP2D6, CYP2A6, CYP7B1, CYP3A5, SLC27A2, ABCB11, CYP2A6, AMACR, CYP7A1, CYP2C19, NAT2, CYP2A6, CYP2C9, CYP2E1, CYP2C9, CYP2C9, SLC10A1, CYP2E1, CYP2E1, CYP3A4, CYP2A6, CYP2C9, CYP2C9, CYP2C9, SULT1A1, FOXA2, OSTalpha, HNF4A, ABCC3, KRT8, COMT, SLC27A5, KRT18, HSD3B7, CP, SOX9, CP, CYP3A5, F2, F12, CYB27A1, CYB39A1, CYB3A7, CYB3A7, FOXA2, SLC27A5, AMACR, AOP4, KRT7, FABP6, ACOT8, HNF4A, AOP4, SLC10A2, AMACR, FABP6, AOP4, COMT, SLCO1A2, TPMT, KRT7, HSD17B4, AOP4, ABCB11, FOXA1, F12, FABP6, CYP39A1, CYP1A2, KRT7, AOP4, FOXA2, CYP2E1, SERPINA1, SLCO1A2, ABCC3, KRT19, CYP3A4, AYP46A1, COMT, KRT7, ABCC3, FOXA1, CYP39A1, CYP2D6, F8, UGT1A6, AKR1C4, CH25H, HNF1B, ACOX2, CYP3A7, HNE4A, ONECUT1, HNF4A, SULT1A1, COMT, HNF1A, KRT8, GSTP1, CYP2D6, ABCC3, HNF1B, SOX9, HNF1A, C1OA, AMACR, AFP, TPMT, SCP2, ABCC3, CP, CP, SULT1A1, HSD17B4, CYP3A5, SCP2, C3, SERPINA1, ALB, ALB, SERPINA1, SERPINA1.

Genes in FIG. 7 (in Order): HSD3B7, SLC27A, AMACR, CYP8B1, BAAT, CYP27A1, CYP39A1, SLCO1B1, SLC27A2, SLC27A2, SLCO1B3, SLC10A1, AKR1D1, ABCC3, ACOT8, ABCC3, CYP7B1, CYP39A1, ABCC3, CYP46A1, AMACR, ABCC3, ABCB11, ACOX2, SLC10A2, FABP6, SLCO1A2, HSD17B4, SLCO1A2, AMACR, AMACR, SLC27A5, ACOT8, FABP6, ABCB11, FABP6, CYP39A1, AKR1C4, SLCO1A2, CH25H, CYP7A1, SCP2, HSD17B4, ABCC3, SCP2, ALB, ALB.

Genes in FIG. 8 (in Order): CYP2E1, CYP2E1, CYP3A4, CYP2A6, CYP2C9, CYP2C9, CYP2C9, CYP2A6, CYP2C9, CYP1A2, SULT1A1, FOXA2, HNF4A, CYP3A4, CYP2C9, CYP2C9, CYP2C9, CYP2E1, CYP3A5, F2, F12, CYP3A4, CYP3A7, CYP3A7, KRT18, COMT, KRT8, CP, HNF4A, ONECUT1, HNF4A, HNF4A, SULT1A1, COMT, HNF1A, KRT8, CYP2D6, CYP3A4, HNF1A, C1QA, COMT, F12, UGT1A6, FOXA1, CYP2D6, F8, FOXA2, CYP1A2, TPMT, HNF4A, COMT, FOXA1, CYP2E1, FOXA2, SERPINA1, CYP3A7, TPMT, CYP2D6, CYP2A6, CYP7B1, C1QB, C1QC, CYP3A5, CYP2C19, NAT2, CYP2A6, CYP7A1, AFP, SERPINA1, C3, SULT1A1, CYP3A5, CP, CP, TPMT, CP, ALB, ALB, SERPINA1, SERPINA1.

Example 2

Fetal Liver Organoids for Hematopoietic Cell Culturing

A. Preparation of Fetal Liver Organoids and Culturing of HSPCs

Liver Organoid Preparation. The liver organoid system can be modified to support the maintenance and expansion of HSPC. Fetal livers are harvested, decellularized, acellular ECM discs are prepared, and enriched hFLPCs are isolated as described above in Example 1 with the following modifications. Sterilized discs were incubated with KM medium for 30-45 minutes prior to cell seeding and then air dried in biosafety cabinet. hFLPCs were re-suspended in hFLP medium, and each disc was seeded with $0.5 \times 10^6$ hFLPCs in hFLP medium. Alternatively, the hFLPCs can be resuspended in Kubota's Media (KM) and seeded in minimal LPC medium. These seeded discs were then allowed to mature for ~5 days at 37° C. to allow the formation of functional liver organoids. The culture medium is changed every 24 hours.

HSPC Preparation from Cord Blood. Cord blood (CB) units are obtained from publicly available sources (e.g., NHLBI BioLINCC Biologic Specimen and Data Repository Information Coordinating Center). Each CB unit is expected to contain about $200 \times 10^6$ total cells but some CB units will have significantly fewer cells and other CB units will have significantly more cells. CB units are thawed, and the mononuclear fraction obtained by centrifugation over a Ficoll density gradient. If necessary, the mononuclear cell fraction is incubated with an ammonium chloride solution (STEMCELL Technologies) to lyse any residual red blood cells. Magnetic separation using MiniMACS™ columns (Miltenyi Biotec) is performed to obtain an enriched population of CD34+ HSP cells. Use of MiniMacs columns to enrich for CD34+ cells enables enrichment of small numbers of highly primitive CD34(−) HSC found in CB units that are often removed during high stringency sorting, resulting in a reduced output from feeder-based expansion cultures [3, 4, 6, 8]. To ensure retention of this rare population, HSPC enrichment may alternatively be performed by lineage depletion rather than positive selection for CD34 expression. Flow cytometry (FACS analysis) is performed to determine the purity of the isolated HSPC population as described in [3, 4, 6, 8, 37].

Long term culture-initiating cells (LTC-IC) can be used as an in vitro indicator of CB-HSPC activity/functionality, as LTC-IC have been shown to be a better predictor of long-term engrafting ability than cobblestone area-forming cells (CAFC) in cord blood [46]. The expanded CB-HSPC can also be tested by transplanting the cells into immunodeficient mice to test their repopulating ability in vivo.

HSPC Culturing on Organoids. After incubating the organoids for 5-7 days, 125,000 CD34⁺ HSP cells were seeded onto each disc. The following different culture media conditions were tested in triplicate: (1) KM, (2) hFLP growth medium; and (3) long term HSC medium made of QBSF-60 serum-free medium (Quality Biological, Gaithersburg, Md., USA) containing 100 ng/ml stem cell factor (SCF), 5 ng/ml basic fibroblast growth factor (bFGF), 10 U/mL leukemia inhibitory factor (LIF), and 100 ng/mL Flt-3 (Peprotech, Rocky Hill, N.J., USA) [3, 4]. Each organoid was cultured at 37° C. in a final volume of 1 mL medium. Media was changed every other day by removing and replacing 500 µl of medium per well. Every 7 days, the media was fully changed, and cells were resuspended in 1 mL of fresh media. At the same time, 500 µl aliquots of cell suspension were retained for HSPC expansion analysis. The liver organoids were cultured for 7 weeks.

B. Evaluation of Fetal Liver Organoids and Characterization of HSPC Expansion

1. Evaluation of Fetal Liver Organoids

At the 7 week mark, the liver organoids were fixed with 10% buffered formalin (Fisher Scientific, Inc., USA), tissue processed and paraffin embedded. Blocks were sectioned at 5 µm and antigen retrieval was performed using Target Retrieval Solution (Dako Co, USA) Immunohistochemical (IHC) analysis was then performed for using primary antibodies for EpCAM (Santa Cruz Biotechnology, USA), CK19 (Santa Cruz Biotechnology, USA), CD45 (BD, USA), αSMA (Abcam, UK) and Hemoglobin F (Bethyl Laboratories, USA). Appropriate secondary antibodies were used for imaging. Sections were analyzed and pictures were taken with a fluorescence microscope (Carl Zeiss Gmgb, Germany).

Figure 14A:
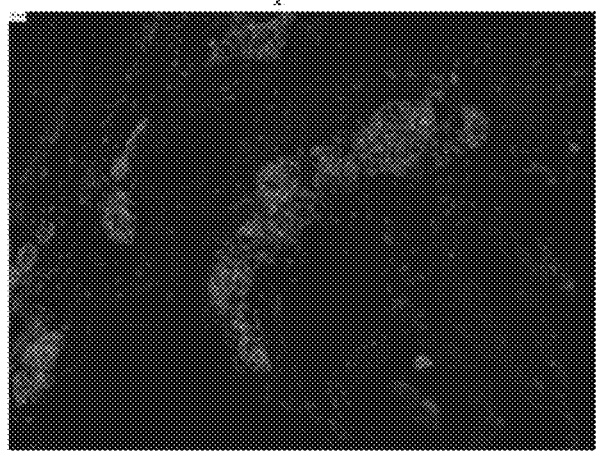
FIGS. 14A-14E show the cellular composition of the fetal liver organoids in accordance with alternate aspects of the invention Immunohistochemical analysis of fetal liver organoids cultured with HSCs was performed after 7 weeks of culturing.

IHC analysis showed that there is extended in vitro survival of abundant clusters of EpCAM+ hepatic cells in the bioengineered liver tissue (FIG. 14A) compared to what is observed under the culture conditions described in Example 1, Section B (growth up to 4 weeks). IHC analysis also showed several CD45+ hematopoietic cells surrounding EpCAM+ hepatic cell clusters and aSMA+ stromal cells, showing two potential stromal populations of the bioengineered liver organoids (FIG. 14B-D).

Figure 14B:
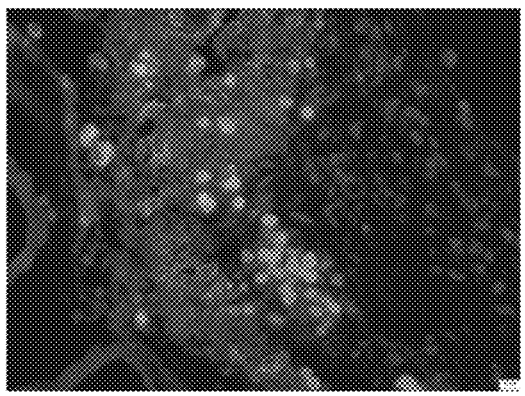
Figure 14C:
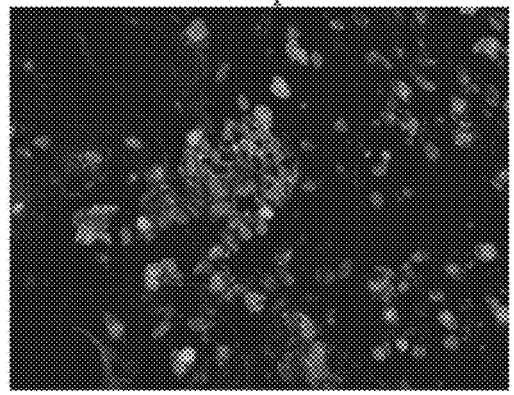
Figure 14D:
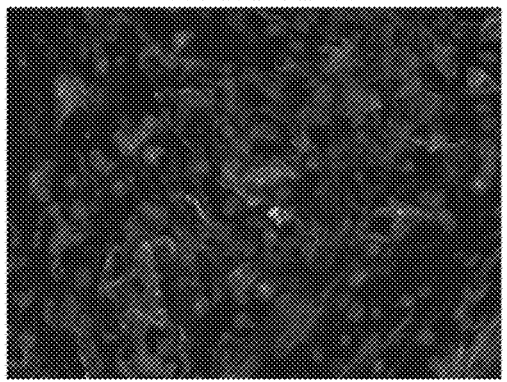
Figure 14E:
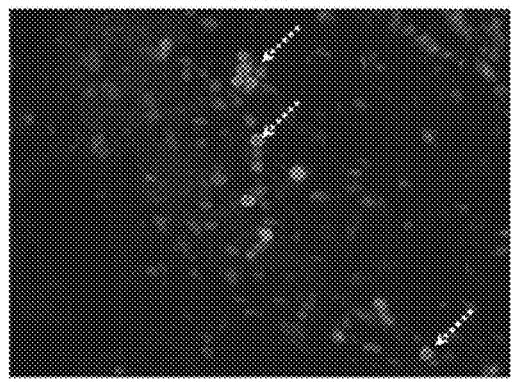

At 7 weeks, it was also possible to observe CK19+ hepatic cell clusters with cells resembling red blood cells (RBC) (FIG. 14B). Further staining with fetal hemoglobin (HbF) confirmed the presence of these nucleated RBCs (FIG. 14E). Because generation of RBCs in in vitro culture systems is difficult and highly inefficient, these data point to a useful application for this culture system.

2. Characterization of HSPC Expansion

As noted, 500 µl aliquots of media were collected from each well every 7 days over the course of 7 weeks. Cells from these aliquots were counted using a hemocytometer to determine the total cell number. Cells were also plated in methylcellulose for colony-forming assay (MethoCult™ H4034 Optimum, STEMCELL Technologies, Inc.) and cultured at 37° C. in an incubator for 7 days before colony forming units (CFU) or burst forming units (BFU) were assessed. As a control, HSCs isolated from cord blood were also assessed directly in the colony forming assay without first culturing on the organoids to determine the baseline colony forming potential of the cell population.

Figure 15A:
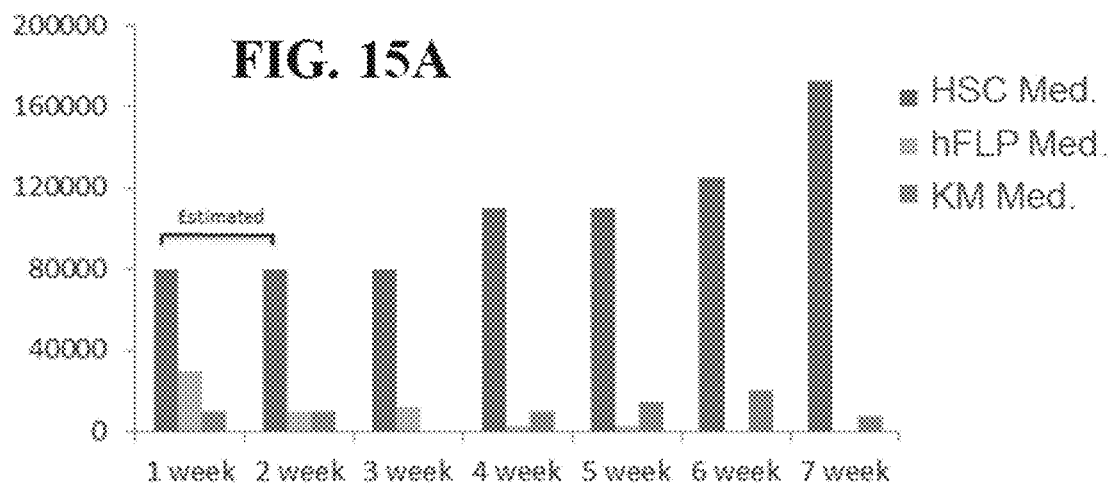
FIG. 15A-FIG.C show hematopoietic cell expansion & colony forming analysis of HSCs cultured on organoids over 7 weeks in KM, hFLP medium, or long term HSC medium in accordance with alternate aspect of the invention.

Cell Expansion. CD34+ CB-derived cells expanded progressively and more efficiently in the wells containing long term HSC media (FIG. 15A). Neither KM nor hFLP medium supported expansion of the CD34+ cells. Significantly, the CD34+ cells were expanded continuously for all 7 weeks of the analysis. This is in contrast to previous studies where HSP cells were cultured using the same long term HSC medium on stromal cells as a feeder layer and were found to expand efficiently for only the first 2 weeks of culturing [3-4].

Figure 15B:
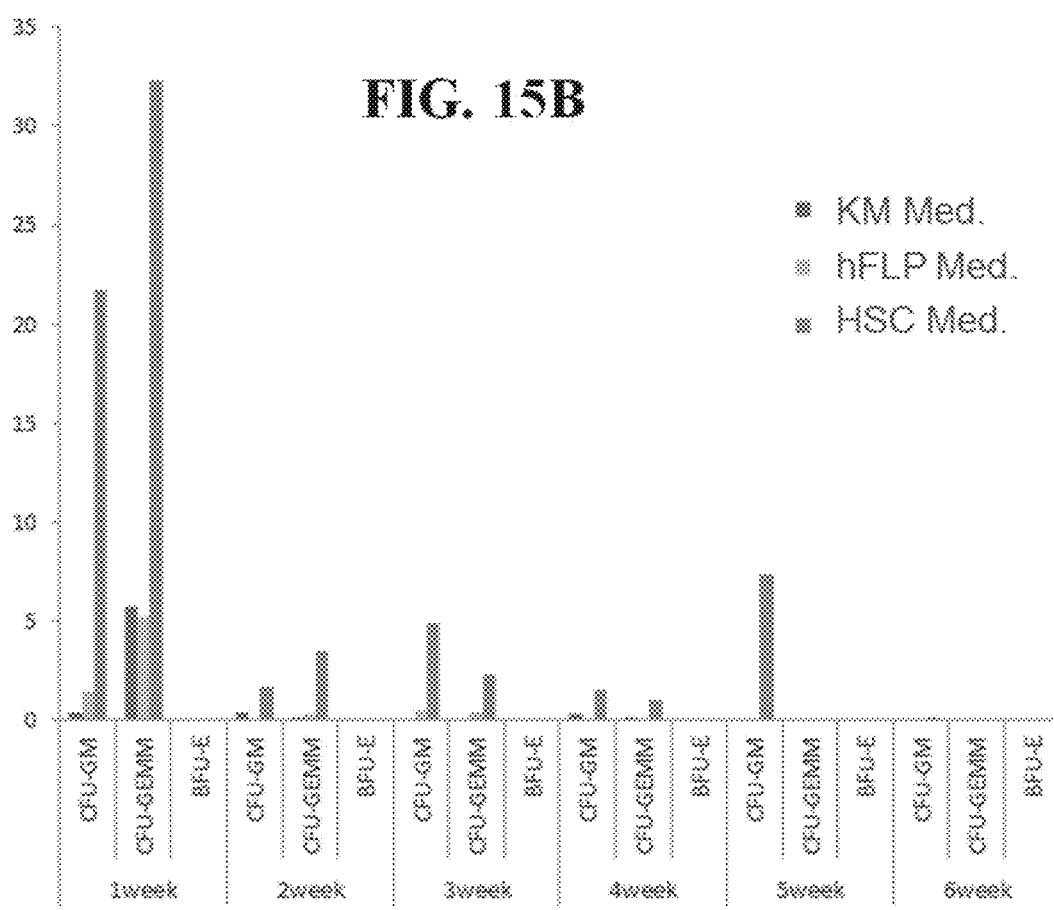
FIG. 15B shows colony forming ability of expanded cells on methylcellulose over 6 weeks. Colony forming units (CFU) were assessed for granulocytes and monocytes (CFU-GM), granulocytes, erythrocytes, monocytes, and megakaryocytes (CFU-GEMM), and erythroid progenitors (BFU-E).
Figure 15C:
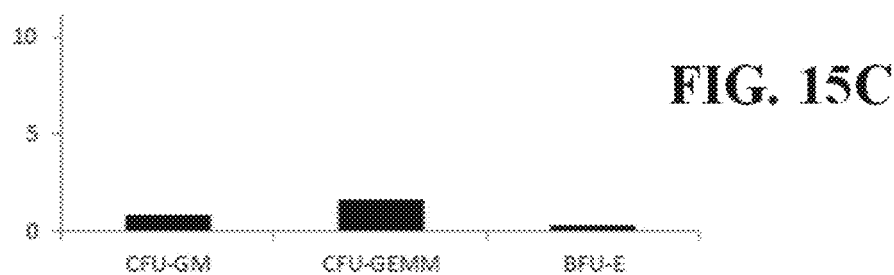
FIG. 15C shows colony forming ability of control HSCs isolated from cord blood.

Colony-Forming Analysis. Three cell populations were assessed by colony forming assay: CFU-GEMM, CFU-GM, and BFU-E. CFU-GEMM assess the presence of multipotent progenitor cells that give rise to granulocytes, erythrocytes, monocytes, and megakaryocytes. These cells give rise to CFU-GM and, eventually, to BFU-E cell populations. CFU-GM assess the presence of granulocyte and monocyte progenitors, which give rise to monoblasts and myeloblasts. BFU-E assess the presence of the earliest known erythroid precursor cell, which give rise to proerythroblasts. Colony-forming assays demonstrated that, during the first week of culture, expansion occurred within the most primitive hematopoietic cells as observed by the 20-fold expansion of CFU-GEMM and that, by week 4, these cultures still contained significant numbers of these primitive colonies (FIG. 15B). The final accumulated number of CFU-GEMM throughout the 7 weeks of the experiment totaled a 25-fold expansion. Also, in comparison with our previously published work in which CFU-GM were lost from culture after 2 weeks, CFU-GM were further maintained in culture until week 6 by culturing on the fetal liver organoid [3-4].

C. Additional Experimental Conditions for Culturing HSCs

Additional analysis of HSPC expansion can also be performed. Organoids can be prepared as described above in Example 2, Section A. As references/controls, as described in [4], the following will be included: 1) cultures in which these three cell populations are plated at this same ratio directly into tissue culture wells to grow in 2-D monolayers; and 2) monolayer cultures of bone marrow-derived MSC (BM-MSC). HSPCs will be prepared from CB as described above in Example 2, Section A. Once the organoids have fully repopulated and the monolayers have been established, culturing of CB-HSPCs will begin. For example, ~250,000 CB-HSPC will be plated in each well containing a hepatic organoid, a 3 cell type monolayer (control), or a BM-MSC monolayer (control), and various media conditions will be tested on the 5-7 day organoids as described above. One condition will be the long term HSC medium. Another condition will include supplementing the medium with a cytokine cocktail 20 ng/mL SCF, 10 ng/mL IL6, and 30 ng/mL FLT3 previously employed in hepatoblast-based HSPC expansion cultures as described in [18]. Other media conditions will also be evaluated, removing or adding certain components. As a control, some organoids will be grown in medium with no added cytokines to rigorously test the ability of the fetal liver organoids to support CB-derived hematopoiesis. While other culture media conditions will be assessed (e.g., containing other components to stimulate HSC expansion), no growth factors will generally be included in the culture media so as to avoid stimulating differentiation of the HSC into mature hematopoietic stem cells. Every 12 hours, 0.5 mL of fresh media will be added to wells. See [39] (indicating that frequent media addition is required to continually dilute factors that cause inhibitory feedback and thus block subsequent HSPC expansion). Every 72 hours throughout the 28-day course of the experiment, 2 mL of media containing the non-adherent cells will be removed from each well prior to the scheduled 0.5 mL media addition. To enable each condition to be performed/analyzed in triplicate and still ensure adequate cell numbers for all analyses are obtained, media/non-adherent cells will be collected from 9 wells with each culture condition and sets of 3 wells pooled together.

Several analyses will then be performed on each of these samples: 1) counting with a hemocytometer to determine the total cell number; 2) flow cytometry to establish the HSPC and lineage content of the expanded population, using monoclonal antibodies against CD3, CD7, and CD19 to evaluate lymphoid lineage differentiation; CD14, CD15, and CD33 to evaluate myeloid differentiation; and CD34 and CD38 to assess the percentage of HSPC remaining in culture; 3) flow cytometric cell cycle analysis, with 7-aminoactinomycin D (7-AAD) to establish the divisional behavior of CD34+ HSPC at each time point in culture, using ModFit software (Becton Dickinson), 4) RNA analysis for markers active during HSC expansion, and 5) IP analysis of fetal liver organoids. These data will then be used to calculate the expansion in total cell number and the fold expansion of both $CD34^+$ CB-HSPC and the more primitive $CD34^+CD38^-$ CB-HSPC at each time point in culture and further characterize the potential of the fetal liver organoids.

D. Measure HSC Activity/Functionality In Vitro

To evaluate the hematopoietic stem/progenitor activity present within the various expansion cultures, cells collected from the organoid cultures each 72 hours will be analyzed using traditional, methylcellulose colony-forming assays (CFU-GEMM, BFU-E, and CFU-GM) to assess the progenitor content of the expanded hematopoietic cell population [25]. Given its ability to allow high throughput, semi-automated screening, the HALO®-96 Human Stem/Progenitor Cell Assay (HuSPCA, Hemogenix) will also be used as described in [40]. This assay can simultaneously detect and quantitate 7 different HSPC populations at varying stages of differentiation, including progenitors of both the myeloid and lymphoid lineages. The populations to be identified/quantitated are: HPP-CFC, CFC-GEMM, CFC-GM, BFU-E, CFC-Mk, CFC-T, and CFC-B. Instead of requiring colonies of cells to be identified visually and enumerated, HALO® relies upon advanced, ATP-based, luciferin/luciferase bioluminescence readout. The assay is highly reproducible, eliminates the inherent subjectivity of visually-scored methylcellulose assays, and is extremely sensitive, requiring roughly 2-logs fewer input cells and allowing the detection of as little as 20 cells. While CFC-GEMM and HPP-CFC detect fairly early hematopoietic cells, long term culture-initiating cell (LTC-IC) assays will be performed as described in [41] to rigorously quantitation of the most primitive HSC content of the expanded cells.

Example 3

Evaluating Signaling of Cell-Fate Determining Microenvironments for Hematopoietic Cells The availability of decellularized liver scaffolds and the ability to selectively repopulate these scaffolds with specific cell populations enables systematic study of the role each niche cell type plays in CB-HSPC fate determination. These studies will allow optimization of conditions that favor either HSC expansion or HSC differentiation. Liver organoids will be prepared as described in Example 2, Section A and B, using long term HSC medium and including any modifications deemed appropriate based on Example 2, Section C and cultured with CD34+ HSPC prepared as described in Example 2, Section A. A control group of empty scaffolds (no cells) will be included to account for the effect of the ECM alone. The ECM is now appreciated to be a key regulator of cell and tissue behavior, by virtue of its ability both to arrange cells in a highly ordered 3-D array, and to serve as a reservoir of growth factors and cytokines [47-49].

As such, it is expected that the fetal liver ECM will exert some effects upon CB-HSPC, even in the absence of niche cells.

CB-HSPC will be plated in each well containing (i) an acellular hepatic disc, or (ii) an acellular hepatic disc repopulated with enriched hFLPCs (or isolated populations of hepatic, stromal and endothelial cells) and the media will be changed long term HSC medium as described above. As described in Example 2, Section C, to rigorously test the support each individual niche cell type can provide to CB-derived hematopoiesis, some cultures will be supplemented with a cytokine cocktail (see also [18]), and others will not. Other media conditions as determined in Example 2, Section C may also be included. Additional culture media conditions will include supplementing the basic culture media and the cytokine culture media with one or more growth factors, hormones, or other factors to support HSC differentiation. Some growth factors, hormones, or other factors that will be tested include oncostatin-M (OSM), TGFβ3, Jagged-1, fetal bovine serum (FBS), dexamethasone, cyclic adenosine monophosphate (cAMP), Prolactin, Glucagon, niacinamide, α-lipoic acid, triiodothyronine, epidermal growth factor (EGF), high-density lipoprotein (HDL), hepatocyte growth factor (HGF), or human growth hormone (HGH). As described in Example 2, Sections A and B, cultures will be fed by adding 0.5 mL of fresh media every 12 hours to continually dilute inhibitory factors. Each 72 hours, 2 mL of media containing the non-adherent cells will be removed from each well, and the following 6 analyses will then be performed on each of these samples:

1) Counting with a hemocytometer to determine the total cell number;
2) Flow cytometry using monoclonal antibodies against lymphoid (CD3, CD7, and CD19) and myeloid (CD14, CD15, and CD33) lineage markers; and CD34 and CD38 to assess the HSPC and lineage content of the expanded population;
3) Methylcellulose colony-forming assays as described in [25] to assess the progenitor content of the expanded hematopoietic cell population;
4) HALO®-96 Human Stem/Progenitor Cell Assay (Hemogenix) as described in [40] to simultaneously detect and quantitate the following HSPC populations at varying stages of differentiation: (i) HPP-SP1 (high proliferative potential—stem and progenitor cell 1), (ii) HPP-SP2, (iii) CFC-GEMM1 (colony-forming cell—granulocyte, erythroid, macrophage, megakaryocyte 1), (iv) CFC-GEMM2, (v) CFC-GEM1 (colony-forming cell—granulocyte, erythroid, macrophage 1), (vi) CFC-GEM2, (vii) CFC-GEM3, and (viii) primitive HPP-CFC.
5) Long term culture-initiating cell (LTC-IC) assays as described in [41] to rigorously quantitate the most primitive HSC content of the expanded cells;
6) To begin decoding the signaling occurring between each niche cell type and the nearby CB-HSPC, culture supernatants will be analyzed with the Human Cytokine 30-Plex Panel (Life Technologies), which simultaneously quantifies 30 different human cytokines, chemokines, and growth factors.

These data will be used to calculate the expansion in total cell number, the fold expansion of primitive CB-HSPC, defined both phenotypically (CD34+, CD34+CD38−) and functionally (HPP-CFC and LTC-IC), and to identify any bias in the lineage commitment as a result of expanding the CB-HSPC over each individual niche cell type.

Example 4

Analysis of Cellular and Matrix Niche Components on HSPC Replication and Division The decellularized hepatic scaffold discs, repopulated with enriched hFLPCS (or isolated hepatoblasts, MSC, and HSEC, singly or in combination) as described above provide an ideal system to study the micro-environment niches of the fetal liver that support asymmetric division and symmetric renewal of HSC. Asymmetric division is regulated by cell polarity, with specific components of the cell membrane, cytoplasmic constituents, and even nuclear contents being unevenly distributed throughout the stem cell such that, upon division, two daughter cells of differing composition are created [50-52]. One key membrane protein within HSC that has been shown to segregate during cell polarization is CD133 [53]. As such, its distribution between daughter cells following cell division has been used to conclusively distinguish between symmetric and asymmetric cell division in cycling stem cells [54] Importantly, CD133$^+$ cells from cord blood and bone marrow are highly enriched in long term culture-initiating cells (LTC-IC) [55, 56] and long-term repopulating cells [57, 58], and expression of CD133 is lost upon differentiation. As such, the transfer of CD133 to daughter progeny of CB-HSPC expanded in the various hepatic discs will be used to determine the characteristics of cellular niches that support asymmetric division and the characteristics of cellular niches that promote self-renewing symmetric division.

Fetal liver organoids will be prepared as described above in Example 2, Sections A-C and culture conditions determined by the experiments described in Example 3 to induce: 1) the greatest degree of expansion of long term culture-initiating cells (LTC-IC); or 2) maintenance of LTC-IC numbers with concomitant production of committed progeny. These outcomes should be indicative of symmetric renewal and asymmetric division, respectively. Once the discs have repopulated to form the liver organoids (5 days), cord blood mononuclear cells will be labeled with the fluorescent membrane dye PKH2 (as described in [59]), and then PKH2-labeled CD133$^+$ HSPC will be isolated on a FACS Aria II, depositing single cells into the individual disc-containing wells of the 96-well plates. Accuracy of single cell deposition will be confirmed visually on an inverted fluorescence microscope. The plate will then be placed in a humidified incubator for a period of 240 hr, as prior studies have shown that the majority of CB-HSPC undergo their first division by day 10 of culture [59]. Every 6 hours, the cells in wells from each experimental group will be fixed with 4% paraformaldehyde to preserve the phenotype until completion of the experiment (t=240 hr). Wells will then be stained with anti-CD133 and examined by confocal microscopy to assess the presence of CD133 within the daughter cells arising from each HSOC division. Prior studies have shown that this method provides very clear-cut results regarding asymmetric division (1 CD133$^+$ cell, 1 CD133$^-$ cell) versus symmetric renewal (2 CD133$^+$ cells) or symmetric commitment (2 CD133$^-$ cells) [54]. Analyzing the percentage of CB-HSPC undergoing each form of division on scaffolds populated with each individual niche cell type will enable identification of which specific niches within the fetal liver support asymmetric division, which support self-renewal, and which promote solely differentiation, with resultant stem cell depletion. Performing IHC and morphologic analysis on the wells containing all 3 niche cell types together will confirm these results at the level of a functional "tissue".

The niche cells may communicate with one another through contact and/or release of paracrine factors, and may thus exert greater, synergistic effects when working together. As such, the outcome of the expansion cultures in which the liver scaffold has been repopulated with a single niche cell type may differ from that obtained when all three cell types are seeded into the scaffold together. Differences such as degree of expansion, extent of differentiation, rate of differentiation, and skewing of lineage output would all provide valuable information about the role each cell type within the niche likely plays in the process of fetal liver hematopoiesis and CB-HSPC expansion.

REFERENCES

1. Tung, S. S., et al., Ex vivo expansion of umbilical cord blood for transplantation. *Best Practice & Research. Clinical Haematology*, 2010. 23(2):245-57.
2. Dahlberg, A., et al., Ex vivo expansion of human hematopoietic stem and progenitor cells. *Blood*, 2011. 117(23): 6083-90.
3. da Silva, C. L., et al., A human stromal-based serum-free culture system supports the ex vivo expansion/maintenance of bone marrow and cord blood hematopoietic stem/progenitor cells. *Experimental Hematology* 33(7): 828-835 (2005).
4. Gonçalves, R., et al., A Stro-1(+) human universal stromal feeder layer to expand/maintain human bone marrow hematopoietic stem/progenitor cells in a serum-free culture system. *Experimental Hematology* 34(10):1353-1359 (2006).
5. Frias, A. M., et al., Generation of functional natural killer and dendritic cells in a human stromal-based serum-free culture system designed for cord blood expansion. *Experimental Hematology* 36(1):61-68 (2008).
6. da Silva, C. L., et al., Differences amid bone marrow and cord blood hematopoietic stem/progenitor cell division kinetics. *Journal of Cellular Physiology* 220(1):102-111 (2009).
7. Andrade, P. Z., et al., Systematic delineation of optimal cytokine concentrations to expand hematopoietic stem/progenitor cells in coculture with mesenchymal stem cells. *Molecular bioSystems* 6(7):1207-1215 (2010).
8. Andrade, P. Z., et al., Initial CD34+ cell enrichment of cord blood determines hematopoietic stem/progenitor cell yield upon ex vivo expansion. *Journal of Cellular Biochemistry* 112(7):1822-1831 (2011).
9. Baptista, P. M., et al., The use of whole organ decellularization for the generation of a vascularized liver organoid. *Hepatology* (2010).
10. Baptista, P. M., et al., Whole organ decellularization—a tool for bioscaffold fabrication and organ bioengineering. *Conference proceedings: Annual International Conference of the IEEE Engineering in Medicine and Biology Society. IEEE Engineering in Medicine and Biology Society. Conference.* 2009:6526-6529 (2009).
11. Lang, R., et al., Three-dimensional culture of hepatocytes on porcine liver tissue-derived extracellular matrix. *Biomaterials* 32(29):7042-7052 (2011).
12. Baptista, P. M., et al., The use of whole organ decellularization for the generation of a vascularized liver organoid. *Hepatology* 53(2):604-617 (2011).

13. Morrison, S. J., et al., The purification and characterization of fetal liver hematopoietic stem cells. *Proc Natl Acad Sci USA* 92(22):10302-10306 (1995).
14. Harrison, D. E., et al., Relative to adult marrow, fetal liver repopulates nearly five times more effectively long-term than short-term. *Experimental Hematology* 25(4): 293-297 (1997).
15. Brummendorf, T. H., et al., Asymmetric cell divisions in hematopoietic stem cells. *Annals of the New York Academy of Sciences* 872:265-72; Discussion 272-273 (1999).
16. Mikkola, H. K. and S. H. Orkin, The journey of developing hematopoietic stem cells. *Development* 133 (19):3733-3744 (2006).
17. Liu, D., et al., Initial division behavior of cord blood hematopoietic stem cells depends on microenvironment. *Zhonghua Xue Ye Xue Za Zhi* 23(10):534-537 (2002).
18. Chou, S. and H. F. Lodish, Fetal liver hepatic progenitors are supportive stromal cells for hematopoietic stem cells. *Proc Natl Acad Sci USA* 107(17): 7799-7804 (2010).
19. Koh, L. P. and N. Chao, Haploidentical hematopoietic cell transplantation. *Bone Marrow Transplantation* 42 Suppl 1:S60-S63 (2008).
20. Ballen, K. K. and Spitzer, T. R., The great debate: haploidentical or cord blood transplant. *Bone Marrow Transplantation* 46(3):323-329 (2011).
21. Ballen, K. K., et al., Selection of optimal alternative graft source: mismatched unrelated donor, umbilical cord blood, or haploidentical transplant. *Blood* 119(9):1972-1980 (2012).
22. Gluckman, E., et al., Hematopoietic reconstitution in a patient with Fanconi's anemia by means of umbilical-cord blood from an HLA-identical sibling. The *New England Journal of Medicine* 321(17):1174-1178 (1989).
23. Broxmeyer, H. E., Insights into the biology of cord blood stem/progenitor cells. *Cell Proliferation.* 44 Suppl 1:55-59 (2011).
24. McNiece, I., et al., Ex vivo expansion of cord blood mononuclear cells on mesenchymal stem cells. *Cytotherapy* 6(4):311-317 (2004).
25. Almeida-Porada, G., et al., Evaluation of serum-free culture conditions able to support the ex vivo expansion and engraftment of human hematopoietic stem cells in the human-to-sheep xenograft model. *J. Hematother. Stem Cell Res.* 9(5):683-693 (2000).
26. Hoggatt, J., et al., Prostaglandin E2 enhances hematopoietic stem cell homing, survival, and proliferation. *Blood* 113(22):5444-5455 (2009).
27. Campbell, T. B., et al, Inhibition of CD26 in human cord blood CD34+ cells enhances their engraftment of nonobese diabetic/severe combined immunodeficiency mice. *Stem Cells and Development* 16(3):347-354 (2007).
28. Choi, Y. S., et al., Effects of mixed feeder cells on the expansion of CD34 cells. *Journal of Bioscience and Bioengineering* 113(3):389-394 (2012).
29. Tiwari, A., et al., Ex vivo expansion of haematopoietic stem/progenitor cells from human umbilical cord blood on acellular scaffolds prepared from MS-5 stromal cell line. *Journal of Tissue Engineering and Regenerative Medicine* (2012).
30. Mortera-Blanco, T., et al., Long-term cytokine-free expansion of cord blood mononuclear cells in three-dimensional scaffolds. *Biomaterials* 32(35):9263-9270 (2011).
31. Macdonald, J., et al., Ex vivo Maintenance of cells from the liver lineage, in Methods of Tissue Engineering (W. Lanza, et al., eds. 2002, Academic Press: San Diego): 151-201.
32. Almeida-Porada, M. G., et al., Tissue of Origin Influences In vivo Differentiative Potential of Mesenchymal Stem Cells. *Blood.* 102(11): abstract #1304 (2003).
33. Chamberlain, J., et al., Neural Generation in vivo differs with route of administration and source of mesenchymal stem cells, *Experimental Hematology* 33(7):49 (2005).
34. Chamberlain, J., et al., Stro-1 identifies a putative mesenchymal stem cell population in human brain. *Experimental Hematology* 31:168 (2003).
35. Porada, C., et al., Adult Mesenchymal Stem Cells: A Pluripotent Population with Multiple Applications. *Current Stem Cell Research and Therapy* 1:231-238 (2006).
36. Porada, C. D. and Almeida-Porada, G., Mesenchymal stem cells as therapeutics and vehicles for gene and drug delivery. *Adv. Drug Deliv. Rev.* 62(12):1156-1166 (2010).
37. da Silva, C. L., et al., Dynamic cell-cell interactions between cord blood haematopoietic progenitors and the cellular niche are essential for the expansion of CD34+, CD34+CD38− and early lymphoid CD7+ cells. *Journal of Tissue Engineering and Regenerative Medicine* 4(2):149-158 (2010).
38. Qiu, L., et al., Ex vivo expansion of CD34+ umbilical cord blood cells in a defined serum-free medium (QBSF-60) with early effect cytokines. *J. Hematother. Stem Cell Res.* 8(6):609-618 (1999).
39. Csaszar, E., et al., Rapid expansion of human hematopoietic stem cells by automated control of inhibitory feedback signaling. *Cell Stem Cell* 10(2):218-229 (2012).
40. Porada, C. D., et al., Development and validation of a novel, high throughput colony-forming assay that allows simultaneous detection and quantitation of seven primitive sheep hematopoietic populations. *Blood* 110(11): 370a (2007).
41. Verfaillie, C. M., et al., Kinetics of engraftment of CD34(−) and CD34(+) cells from mobilized blood differs from that of CD34(−) and CD34(+) cells from bone marrow. *Experimental Hematology* 28(9):1071-1079 (2000).
42. Li, N., et al., Human umbilical vein endothelial cells increase ex vivo expansion of human CD34(+) PBPC through IL-6 secretion. *Cytotherapy* 8(4):335-342 (2006).
43. Magin, A. S., et al., Primary cells as feeder cells for coculture expansion of human hematopoietic stem cells from umbilical cord blood—a comparative study. *Stem Cells Dev.* 18(1):173-186 (2009).
44. da Silva, C. L., et al., Modelling of ex vivo expansion/maintenance of hematopoietic stem cells. *Bioprocess and Biosystems Engineering* 25(6):365-369 (2003).
45. Gonçalves, R., et al., Kinetic analysis of the ex vivo expansion of human hematopoietic stem/progenitor cells. *Biotechnology Letters* 28(5):335-340 (2006).
46. Denning-Kendall, P., et al., Cobblestone area-forming cells in human cord blood are heterogeneous and differ from long-term culture-initiating cells. *Stem Cells* 21(6): 694-701 (2003).
47. Schmeichel, K. L., et al., Structural cues from the tissue microenvironment are essential determinants of the human mammary epithelial cell phenotype. *J. Mammary Gland Biol. Neoplasia* 3(2):201-213 (1998).
48. Zschenker, O., et al., Genome-Wide Gene Expression Analysis in Cancer Cells Reveals 3D Growth to Affect ECM and Processes Associated with Cell Adhesion but Not DNA Repair. *PLoS One* 7(4):e34279 (2012).
49. Carson, D. D., Extracellular matrix: forum introduction. *Reprod. Biol. Endocrinol.* 2:1 (2004).

50. Giebel, B. and J. Beckmann, Asymmetric cell divisions of human hematopoietic stem and progenitor cells meet endosomes. *Cell Cycle* 6(18):2201-2204 (2007).
51. Giebel, B., Cell polarity and asymmetric cell division within human hematopoietic stem and progenitor cells. *Cells Tissues Organs* 188(1-2):116-126 (2008).
52. Gorgens, A., et al., Lipid raft redistribution and morphological cell polarization are separable processes providing a basis for hematopoietic stem and progenitor cell migration. *Int. J. Biochem. Cell Biol.* (2012).
53. Giebel, B., et al., Segregation of lipid raft markers including CD133 in polarized human hematopoietic stem and progenitor cells. *Blood* 104(8):2332-2338 (2004).
54. Lathia, J. D., et al., Distribution of CD133 reveals glioma stem cells self-renew through symmetric and asymmetric cell divisions. *Cell Death Dis.* 2:e200 (2011).
55. de Wynter, E. A., et al., CD34+AC133+ cells isolated from cord blood are highly enriched in long-term culture-initiating cells, NOD/SCID-repopulating cells and dendritic cell progenitors. *Stem Cells* 16(6):387-96 (1998).
56. Matsumoto, K., et al., In vitro proliferation potential of AC133 positive cells in peripheral blood. *Stem Cells* 18(3):196-203 (2000).
57. Boxall, S. A., et al., Haematopoietic repopulating activity in human cord blood CD133+ quiescent cells. *Bone Marrow Transplant* 43(8):627-635 (2009).
58. Yin, A. H., et al., AC133, a novel marker for human hematopoietic stem and progenitor cells. *Blood* 90:5002-5012 (1997).
59. Giebel, B., et al., Primitive human hematopoietic cells give rise to differentially specified daughter cells upon their initial cell division. *Blood* 107(5):2146-2152 (2006).
60. Wu, M., et al., Imaging hematopoietic precursor division in real time. *Cell Stem Cell* 1(5):541-554 (2007).
61. Hofmann, M. C., et al., A Fiber-Optic-Based Imaging System for Non-Destructive Assessment of Cell-Seeded Tissue-Engineered Scaffolds. *Tissue Eng Part C Methods* 18(9):677-687 (2012).
62. Schuster, J. A. et al., Expansion of hematopoietic stem cells for transplantation: current perspectives. *Exper. Hematology & Oncol.* 1:12 (2012).
63. Walasek, M. A. et al., Hematopoietic Stem Cell Expansion: Challenges and Opportunities. *Ann. N.Y. Acad. Sci.* 1266:138-150 (2012).
64. Duchez, P., et al., Definitive Setup of Clinical Scale Procedure for Ex vivo Expansion of Cord Blood Hematopoietic Cells for Transplantation. *Cell Transplantation* 21:2517-2521 (2012).
65. Szabo, E., et al., Direct conversion of human fibroblasts to multilineage blood progenitors. *Nature* 468:521-526 (2010).
66. Ciriza, J., et al., The Migration of Hematopoietic Progenitors from the Fetal Liver to the Fetal Bone Marrow: Lessons Learned and Possible Clinical Applications. *Experimental Hematology* 41(5):411-423 (2013)
67. Kubota, H. and Reid, L., Clonogenic hepatoblasts, common precursors for hepatocytic and biliary lineages, are lacking classical major histocompatibility complex class I antigen. *Proc. Nat. Acad. Sci. USA* 97(22):12132-12137 (2000).
68. Norkin, M. et al., Umbilical cord blood graft enhancement strategies: has the time come to move these into the clinic? *Bone Marrow Transplantation* 1-6 (2012).
69. Punzel, M. et al., The symmetry of initial divisions of human hematopoietic progenitors is altered only by the cellular microenvironment. *Experimental Hematology* 31:339-347 (2003).
70. Tateno, C. et al., Near completely humanized liver in mice shows human-type metabolic responses to drugs. *Amer. J. Pathol.* 165:901-912 (2004).
71. Azuma, H. et al., Robust expansion of human hepatocytes in Fah-/-/Rag2-/-/Il2rg-/- mice. *Nat. Biotechnol.* 25:903-910 (2007).
72. Chen, A. A. et al., Humanized mice with ectopic artificial liver tissues. *Proc. Natl. Acad. Sci. USA* 108:11842-11847 (2011).
73. Seok, J. et al., Genomic responses in mouse models poorly mimic human inflammatory diseases. *Proc. Natl. Acad. Sci. USA* 110(9):3507-3512 (2013).
74. Khetani, S. R. & Bhatia, S. N. Microscale culture of human liver cells for drug development. *Nat. Biotechnol.* 26:120-126 (2008).
75. Drewitz, M. et al., Towards automated production and drug sensitivity testing using scaffold-free spherical tumor microtissues. *Biotechnology Journal* 6:1488-1496 (2011).
76. Katsuda, T. et al., Biliary Epithelial Cells Play an Essential Role in the Reconstruction of Hepatic Tissue with a Functional Bile Ductular Network. *Tissue Eng. Part A* 19(21-22):2402-2411 (2013).
77. Takebe, T. et al. Vascularized and functional human liver from an iPSC-derived organ bud transplant. *Nature* 499:481-484 (2013).
78. Baptista, P. M. et al., Human liver bioengineering using a whole liver decellularized bioscaffold. *Methods Mol. Biol.* 1001:289-298 (2013).
79. Gunn, C. K. Hereditary Acholuric Jaundice in the Rat. *Canadian Medical Association journal* 50:230-237 (1944).
80. Mazziotti, M. V. et al. Anomalous development of the hepatobiliary system in the Inv mouse. *Hepatology* 30:372-378 (1999).

All printed patents and publications referred to in this application are hereby incorporated herein in their entirety by this reference.

The foregoing is illustrative of the present invention, and is not to be construed as limiting thereof. It will be appreciated that various changes can be made therein without departing from the spirit and scope of the invention. The invention is defined by the following claims, with equivalents of the claims to be included therein.

We claim:

1. An in vitro liver organoid for culturing hematopoietic stem cell (HSC), comprising:
    (a) a bioscaffold excised from a portion of decellularized liver tissue from a non-fetal donor, the bioscaffold comprising native extracellular matrix (ECM) and native vascular channels; and
    (b) at least one of isolated fetal hepatoblasts from a fetal donor and isolated fetal stromal cells expressing at least one of CD105 or alpha-SMA from a fetal donor, wherein the at least one of isolated fetal liver hepatoblasts and isolated fetal stromal cells form a microenvironment niche that supports hematopoietic stem cell (HSC) expansion and/or differentiation within the bioscaffold.

2. The liver organoid of claim 1, wherein the organoid also comprises isolated cholangiocytes.

3. The liver organoid of claim 1, wherein the organoid also comprises at least one of liver endothelial cells, liver sinusodial cells, vascular smooth muscle cells, or pericytes.

4. The liver organoid of claim 1, wherein the isolated fetal hepatoblasts comprise at least one of fetal liver hepatoblasts, hepatoblasts derived from adult-derived liver stem cells, hepatoblasts derived from induced pluripotent stem cells, or hepatoblasts derived from embryonic stem cells.

5. The liver organoid of claim 1, wherein the micro-environment niches support expansion or differentiation of at least one of HSC obtained from cord blood, HSC obtained from bone marrow, HSC derived from induced pluripotent stem cells, HSC derived from embryonic stem cells, or HSC derived from direct reprogramming of adult somatic cells.

6. A method of producing hematopoietic cells (HSC) comprising the steps of:
   (a) providing the liver organoid of claim 1;
   (b) seeding the liver organoid with HSC;
   (c) culturing the HSC on the liver organoid in culture media; and
   (d) collecting at least one of expanded HSC or differentiated hematopoietic cells from the culture media.

7. The method of claim 6, wherein the culture media in step (c) excludes exogenous growth factors, and wherein expanded HSC or expanded HSC and immature hematopoietic stem cells are collected in step (d).

8. The method of claim 4, wherein the culture media in step (c) comprises at least one of stem cell factor (SCF), fibroblast growth factor (FGF), interleukin-6 (IL-6), Fms-like tyrosine kinase 3 (FLT3), or leukemia inhibitory factor (LIF).

9. The method of claim 6, wherein the liver organoid is seeded with at least one of HSC obtained from cord blood, HSC obtained from bone marrow, HSC derived from induced pluripotent stem cells, HSC derived from embryonic stem cells, or HSC derived from direct reprogramming of adult somatic cells.

10. The method of claim 6, wherein the differentiated hematopoietic cells comprise hematopoietic progenitor cells (HPC), myeloid progenitor cells (MPC), lymphoid progenitor cells (LPC), lymphocytes, granulocytes, macrophages, erythrocytes, or platelets.

11. The method of claim 6, wherein the differentiated hematopoietic cells comprise an enriched population of differentiated erythrocytes.

12. The method of claim 6, wherein the culture media in step (c) comprises erythropoietin (EPO).

13. The liver organoid of claim 1, wherein the micro-environment niche supports expansion of at least one of HSC obtained from cord blood, HSC obtained from bone marrow, HSC derived from induced pluripotent stem cells, HSC derived from embryonic stem cells, or HSC derived from direct reprogramming of adult somatic cells.

14. A three-dimensional cell culture system for expanding or differentiating HSC, comprising:
   (a) the liver organoid of claim 1, and (b) a medium for culturing HSCs, wherein the medium comprises at least one of stem cell factor (SCF), interleukin-6 (IL-6), leukemia inhibitory factor (LIF), fibroblast growth factor (FGF), erythropoietin (EPO), or human growth hormone (HGH).

15. The three-dimensional system of claim 14, wherein three dimensional system further comprises HSCs.

16. The method of claim 7, wherein the culture media further comprises erythropoietin (EPO).

17. A method of generating the in vitro liver organoid of claim 1, comprising the steps of:
   (a) providing the bioscaffold;
   (b) seeding the bioscaffold with the at least one of isolated fetal hepatoblasts from a fetal donor and isolated fetal stromal cells expressing at least one of CD105 or alpha-MSA from a fetal donor; and
   (c) culturing the at least one of isolated fetal hepatoblasts and isolated fetal stromal cells within the bioscaffold in the presences of culture media for sufficient time to form in the bioscaffold the micro-environment niche that supports HSC expansion and/or differentiation, thereby forming the in vitro liver organoid.

18. The method of claim 17, wherein the culture media comprises at least one of epidermal growth factor (EGF), hepatocyte growth factor (HGF), insulin-like growth factor (IGF-1), glycogen synthase kinase-3beta inhibitor (GSK3βi), or thiazovivin.

19. The method of claim 17, wherein the culturing of step (c) occurs for about 5 days.

20. The method of claim 17, wherein in culture medium is changed every 24 hours in the culturing of step (c).

* * * * *